(12) United States Patent
Lynn et al.

(10) Patent No.: US 10,354,429 B2
(45) Date of Patent: *Jul. 16, 2019

(54) PATIENT STORM TRACKER AND VISUALIZATION PROCESSOR

(71) Applicant: Lawrence A. Lynn, Columbus, OH (US)

(72) Inventors: Lawrence A. Lynn, Columbus, OH (US); Michael Hunt, Yardley, PA (US); Cihan Karasinir, St. Louis, MO (US); Eric N. Lynn, Villa Ridge, MO (US); Andrey Podorozhansky, Chesterfield, MO (US)

(73) Assignee: Lawrence A. Lynn, Columbus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/193,829

(22) Filed: Feb. 28, 2014

(65) Prior Publication Data
US 2014/0176558 A1 Jun. 26, 2014

Related U.S. Application Data

(63) Continuation-in-part of application No. 13/677,295, filed on Nov. 14, 2012.
(Continued)

(51) Int. Cl.
G06Q 10/06 (2012.01)
G06T 13/60 (2011.01)
(Continued)

(52) U.S. Cl.
CPC ........ G06T 13/60 (2013.01); G06Q 10/06311 (2013.01); G06Q 50/24 (2013.01);
(Continued)

(58) Field of Classification Search
CPC .............................. G06Q 50/22; G06Q 50/24
(Continued)

(56) References Cited

U.S. PATENT DOCUMENTS 4,630,614 A 12/1986 Atlas
5,520,176 A 5/1996 Cohen
(Continued)

FOREIGN PATENT DOCUMENTS

EP 1529487 A1 7/2003
JP 05-266002 10/1993
(Continued)

OTHER PUBLICATIONS

Campbell, Beverly, Arterial Waveforms: Monitoring Changes in Configuration, Hemodynamics, Heart & Lung, May/Jun. 1997, vol. 26, No. 3, pp. 204-214.
(Continued)

Primary Examiner — Jonathan Ng
(74) Attorney, Agent, or Firm — Vorys, Sater, Seymour and Pease LLP; Rex W. Miller, II

(57) ABSTRACT

A patient monitoring system is described herein. In one example, the patient monitoring system comprises at least one processor programmed to generate an image which displays a patient condition as color weather radar on a map. In some examples, at least one monitored condition is positioned on the map so that the weather image expands, develops or moves over the condition.

20 Claims, 23 Drawing Sheets

Related U.S. Application Data

(60) Provisional application No. 61/770,919, filed on Feb. 28, 2013, provisional application No. 61/770,971, filed on Feb. 28, 2013.

(51) Int. Cl.
  *G06Q 50/24* (2012.01)
  *G16H 40/63* (2018.01)
  *G16H 10/60* (2018.01)
  *G16H 50/70* (2018.01)
  *G16H 50/20* (2018.01)
  *G16H 15/00* (2018.01)

(52) U.S. Cl.
  CPC ............ *G16H 10/60* (2018.01); *G16H 15/00* (2018.01); *G16H 40/63* (2018.01); *G16H 50/20* (2018.01); *G16H 50/70* (2018.01)

(58) Field of Classification Search
  USPC ........................................................ 705/2, 3
  See application file for complete search history.

(56) References Cited

U.S. PATENT DOCUMENTS

| | | |
|---|---|---|
| 5,639,617 A | 6/1997 | Bohuon |
| 5,769,082 A | 6/1998 | Perel |
| 5,804,370 A | 9/1998 | Romaschin et al. |
| 5,840,019 A | 11/1998 | Wirebaugh |
| 5,942,986 A | 8/1999 | Shabot et al. |
| 6,120,441 A | 9/2000 | Griebel |
| 6,148,814 A | 11/2000 | Clemmer et al. |
| 6,159,683 A | 12/2000 | Romaschin et al. |
| 6,342,039 B1 | 1/2002 | Lynn et al. |
| 6,583,794 B1 | 6/2003 | Wattenberg |
| 6,609,016 B1 | 8/2003 | Lynn |
| 6,748,252 B2 | 6/2004 | Lynn et al. |
| 6,752,150 B1 | 6/2004 | Remmers et al. |
| 6,760,608 B2 | 7/2004 | Lynn |
| 6,804,656 B1 | 10/2004 | Rosenfield et al. |
| 6,816,266 B2 | 11/2004 | Varshneya et al. |
| 7,081,095 B2 | 7/2006 | Lynn et al. |
| 7,252,637 B2 | 8/2007 | Ebner et al. |
| 7,398,115 B2 | 7/2008 | Lynn |
| 7,428,520 B2 | 9/2008 | Armstrong et al. |
| 7,465,555 B2 | 12/2008 | Anderson et al. |
| 7,632,685 B2 | 12/2009 | Ivey et al. |
| 7,645,573 B2 | 1/2010 | Ivey et al. |
| 7,645,613 B2 | 1/2010 | Ivey et al. |
| 7,659,075 B2 | 2/2010 | Bergmann |
| 7,668,579 B2 | 2/2010 | Lynn |
| 7,706,852 B2 | 4/2010 | Baker, Jr. |
| 7,723,492 B2 | 5/2010 | Bergmann et al. |
| 7,758,503 B2 | 7/2010 | Lynn et al. |
| 7,767,395 B2 | 8/2010 | Garrett et al. |
| 7,792,642 B1* | 9/2010 | Neilley et al. .................. 702/3 |
| 7,970,725 B2 | 6/2011 | Armstrong et al. |
| 8,152,732 B2 | 4/2012 | Lynn et al. |
| 8,187,201 B2 | 5/2012 | Lynn |
| 8,241,213 B2 | 8/2012 | Lynn et al. |
| 8,274,360 B2 | 9/2012 | Sampath et al. |
| 8,275,553 B2 | 9/2012 | Ochs et al. |
| 8,365,730 B2 | 2/2013 | Baker, Jr. et al. |
| 8,398,555 B2 | 3/2013 | Ochs et al. |
| 8,414,488 B2 | 4/2013 | Colman et al. |
| 8,428,966 B2 | 5/2013 | Green, III et al. |
| 8,438,041 B2 | 5/2013 | Green, III et al. |
| 8,439,835 B1 | 9/2013 | McKinley et al. |
| 8,527,449 B2 | 9/2013 | Gajic et al. |
| 8,663,107 B2 | 3/2014 | Kiani |
| 8,666,467 B2 | 5/2014 | Lynn et al. |
| 8,728,001 B2 | 7/2014 | Lynn |
| 8,781,753 B2 | 7/2014 | Ochs et al. |
| 9,361,430 B2* | 6/2016 | Seward .................. G06N 5/022 |
| 2001/0018557 A1 | 8/2001 | Lynn et al. |
| 2002/0026941 A1 | 3/2002 | Biondi et al. |
| 2002/0030682 A1* | 3/2002 | Eberlein ............ A61B 5/0002 345/440 |
| 2002/0099273 A1 | 7/2002 | Bocionek et al. |
| 2002/0165462 A1 | 11/2002 | Westbrook et al. |
| 2002/0173707 A1 | 11/2002 | Lynn et al. |
| 2002/0190863 A1 | 12/2002 | Lynn |
| 2003/0101076 A1 | 5/2003 | Zaleski |
| 2003/0158466 A1* | 8/2003 | Lynn et al. .................. 600/300 |
| 2003/0181815 A1 | 9/2003 | Ebner et al. |
| 2003/0194752 A1 | 10/2003 | Anderson et al. |
| 2003/0228625 A1 | 12/2003 | Toh et al. |
| 2004/0039295 A1 | 2/2004 | Olbrich et al. |
| 2004/0048264 A1 | 3/2004 | Stoughton et al. |
| 2004/0078219 A1 | 4/2004 | Kaylor et al. |
| 2004/0078228 A1 | 4/2004 | Fitzgerald et al. |
| 2004/0096917 A1 | 5/2004 | Ivey et al. |
| 2004/0097460 A1 | 5/2004 | Ivey et al. |
| 2004/0106142 A1 | 6/2004 | Ivey et al. |
| 2004/0111014 A1 | 6/2004 | Hickle |
| 2004/0128163 A1 | 7/2004 | Goodman et al. |
| 2004/0157242 A1 | 8/2004 | Ivey et al. |
| 2004/0183683 A1 | 9/2004 | Funahashi |
| 2004/0249299 A1 | 12/2004 | Cobb |
| 2005/0001728 A1 | 1/2005 | Appelt et al. |
| 2005/0062609 A9 | 3/2005 | Lynn |
| 2005/0065556 A1 | 3/2005 | Reghabi et al. |
| 2005/0098178 A1 | 5/2005 | Banner et al. |
| 2005/0109340 A1 | 5/2005 | Tehrani |
| 2005/0125256 A1 | 6/2005 | Schoenberg et al. |
| 2005/0164238 A1 | 7/2005 | Valkirs et al. |
| 2005/0181354 A1 | 8/2005 | Estep, III |
| 2005/0240091 A1 | 10/2005 | Lynn |
| 2006/0149144 A1 | 7/2006 | Lynn et al. |
| 2006/0155176 A1 | 7/2006 | Ebner et al. |
| 2006/0155206 A1 | 7/2006 | Lynn |
| 2006/0155207 A1 | 7/2006 | Lynn et al. |
| 2006/0157647 A1 | 7/2006 | Siuzdak et al. |
| 2006/0161071 A1 | 7/2006 | Lynn et al. |
| 2006/0189880 A1 | 8/2006 | Lynn et al. |
| 2006/0195041 A1 | 8/2006 | Lynn et al. |
| 2006/0195149 A1 | 8/2006 | Hopper et al. |
| 2006/0200012 A1 | 9/2006 | Mansour et al. |
| 2006/0235324 A1 | 10/2006 | Lynn |
| 2006/0235726 A1 | 10/2006 | Paraison et al. |
| 2006/0253300 A1* | 11/2006 | Somberg ................ G06Q 50/22 705/2 |
| 2006/0271408 A1 | 11/2006 | Rosenfeld et al. |
| 2006/0276695 A9 | 12/2006 | Lynn et al. |
| 2007/0093701 A1 | 4/2007 | Myers et al. |
| 2007/0093721 A1 | 4/2007 | Lynn et al. |
| 2007/0129647 A1 | 6/2007 | Lynn |
| 2007/0149860 A1 | 6/2007 | Lynn et al. |
| 2007/0184512 A1 | 8/2007 | Ivey et al. |
| 2007/0191688 A1 | 8/2007 | Lynn |
| 2007/0191697 A1 | 8/2007 | Lynn et al. |
| 2007/0255322 A1 | 11/2007 | Gerber et al. |
| 2007/0282212 A1 | 12/2007 | Sierra et al. |
| 2008/0050829 A1 | 2/2008 | Ivey et al. |
| 2008/0051764 A1 | 2/2008 | Dent et al. |
| 2008/0091088 A1 | 4/2008 | Kiani |
| 2008/0114576 A1 | 5/2008 | Jackson et al. |
| 2008/0138832 A1 | 6/2008 | Ivey et al. |
| 2008/0195322 A1 | 8/2008 | Altschuler et al. |
| 2008/0200775 A1 | 8/2008 | Lynn |
| 2008/0200819 A1 | 8/2008 | Lynn et al. |
| 2008/0208012 A1 | 8/2008 | Ali |
| 2008/0208618 A1 | 8/2008 | Schoenberg et al. |
| 2008/0235049 A1 | 9/2008 | Morita et al. |
| 2008/0235057 A1 | 9/2008 | Weidenhaupt et al. |
| 2008/0275349 A1 | 11/2008 | Halperin et al. |
| 2008/0286763 A1 | 11/2008 | Russwurm et al. |
| 2008/0287756 A1 | 11/2008 | Lynn |
| 2008/0305464 A1 | 12/2008 | Lynn |
| 2009/0069704 A1 | 3/2009 | MacAdam et al. |
| 2009/0082641 A1 | 3/2009 | Giftakis et al. |
| 2009/0083072 A1 | 3/2009 | Osawa et al. |
| 2009/0143694 A1 | 6/2009 | Krauss et al. |
| 2009/0171169 A1* | 7/2009 | Nagata .......................... 600/301 |

(56) References Cited

U.S. PATENT DOCUMENTS

| | | | |
|---|---|---|---|
| 2009/0186774 | A1 | 7/2009 | Turner et al. |
| 2009/0187082 | A1 | 7/2009 | Cuddihy et al. |
| 2009/0281838 | A1 | 11/2009 | Lynn et al. |
| 2009/0281839 | A1 | 11/2009 | Lynn et al. |
| 2009/0299154 | A1 | 12/2009 | Segman |
| 2009/0318775 | A1 | 12/2009 | Michelson et al. |
| 2010/0066540 | A1 | 3/2010 | Theobald et al. |
| 2010/0070888 | A1 | 3/2010 | Watabe et al. |
| 2010/0079292 | A1 | 4/2010 | Lynn |
| 2010/0094648 | A1 | 4/2010 | Seward |
| 2010/0160171 | A1 | 6/2010 | Freishtat |
| 2010/0174161 | A1 | 7/2010 | Lynn |
| 2010/0234705 | A1 | 9/2010 | Lynn |
| 2010/0261977 | A1 | 10/2010 | Seely |
| 2011/0009722 | A1 | 1/2011 | Amundson et al. |
| 2011/0009760 | A1 | 1/2011 | Zhang et al. |
| 2011/0015501 | A1 | 1/2011 | Lynn et al. |
| 2011/0130671 | A1 | 1/2011 | MacQuarrie et al. |
| 2011/0105350 | A1 | 5/2011 | Garrett et al. |
| 2011/0118569 | A1 | 5/2011 | Shi et al. |
| 2011/0208018 | A1 | 8/2011 | Kiani |
| 2011/0208539 | A1 | 8/2011 | Lynn |
| 2012/0053425 | A1 | 3/2012 | Michelson et al. |
| 2012/0145152 | A1 | 6/2012 | Lain et al. |
| 2012/0165623 | A1 | 6/2012 | Lynn et al. |
| 2012/0172247 | A1 | 7/2012 | Narimatsu et al. |
| 2012/0197094 | A1 | 8/2012 | Zhang et al. |
| 2012/0220845 | A1 | 8/2012 | Campbell |
| 2012/0232359 | A1 | 9/2012 | Al-Ali et al. |
| 2012/0302845 | A1 | 11/2012 | Lynn et al. |
| 2012/0328594 | A1 | 12/2012 | McKenna et al. |
| 2012/0330118 | A1 | 12/2012 | Lynn et al. |
| 2013/0052671 | A1 | 2/2013 | Grueb et al. |
| 2013/0060110 | A1 | 3/2013 | Lynn et al. |
| 2013/0073311 | A1 | 3/2013 | Lynn et al. |
| 2013/0124221 | A1 | 5/2013 | Lynn |
| 2013/0131993 | A1 | 5/2013 | Lynn et al. |
| 2013/0158375 | A1 | 6/2013 | Lynn |
| 2013/0209068 | A1 | 8/2013 | Lynn |
| 2013/0218600 | A1 | 8/2013 | Lynn et al. |
| 2013/0268291 | A1 | 10/2013 | Lynn et al. |
| 2013/0290011 | A1 | 10/2013 | Lynn et al. |
| 2013/0338459 | A1 | 12/2013 | Lynn |
| 2014/0152673 | A1 | 6/2014 | Lynn et al. |
| 2014/0163897 | A1 | 6/2014 | Lynn et al. |
| 2014/0176538 | A1 | 6/2014 | Lynn et al. |
| 2014/0176558 | A1 | 6/2014 | Lynn et al. |
| 2014/0180722 | A1 | 6/2014 | Lynn et al. |

FOREIGN PATENT DOCUMENTS

| | | | |
|---|---|---|---|
| JP | 2002336207 | A | 11/2002 |
| JP | 2007058565 | A | 3/2007 |
| JP | 4435681 | | 3/2010 |
| JP | 4435681 | B2 | 3/2010 |
| KR | 1020020064206 | | 8/2002 |
| WO | WO 2004/056301 | A2 | 7/2004 |
| WO | WO 2005/056087 | A1 | 6/2005 |
| WO | 2010/065262 | A1 | 6/2010 |
| WO | WO 2010/108018 | A3 | 9/2010 |
| WO | 2013/074708 | A1 | 5/2013 |

OTHER PUBLICATIONS

Abelson, Harold et al., Structure and Interpretation of Computer Programs, MIT Press, 2nd Edition, 1996, p. 99-107, 113-126.

Abraham, E., et al., Sequential Cardiorespiratory Patterns in Septic Shock, Crit Care Med., Oct. 1983, pp. 799-803, vol. 11, No. 10.

Agronsky, Dominik, et al., Diagnosing Community-Acquired Pneumonia with a Bayesian Network, AMIA, Inc., 1998, pp. 632-636.

Alattar, M. A.et al., Opiod-associated central sleep apnea: a case series, 2009, pp. 201-206.

Apostolopoulou, Eleni et al, Infection Probability Score, APACHE II and KARNOFSKY scoring systems as predictors of bloodstream infection onset in hematology-oncology patients, BMC Infectious Diseases, 2010, vol. 10, No. 135, 8 pages.

Augusto, Juan Carlos, Temporal Reasoning for Decision Support in Medicine, Artificial Intelligence in Medicine, 2005, vol. 33, pp. 1-24.

Bland, RD et al., Probability of Survival as a Prognostic and Severity of Illness Score in Critically Ill Surgical Patients, Crit Care Med., Feb. 1985, pp. 91-95, vol. 13, No. 2 (Abstract).

Bossink, Alko et al., Prediction of Mortality in Febrile Medical Patients, CHEST, Jun. 1998, vol. 113, No. 6, pp. 1533-1541.

Brabrand, Mikkel et al., Risk scoring systems for adults admitted to the emergency department: a systematic review, Scandinavian Journal of Trauma, Resuscitation & Emergency Medicine, Retrieved from <http://www.sjtrem.com/content/18/1/8>, 2010, pp. 1-8.

Burykin, Anton et al., Toward optimal display of physiologic status in critical care: I. Recreating bedside displays from archived physiologic data, Journal of Critical Care, 2010 (Article in Press), 9 pages.

Cavallazzi, MD, Rodrigo, Is the Band Count Useful in the Diagnosis of Infection? An Accuracy Study in Critically Ill Patients, Journal of Intensive Care Medicine, 2010, 5 pages.

Charbonnier et al., "A trend-based alarm system to improve patient monitoring in intensive care units." Control Engineering Practice, Pergamon Press, Oxford, GB, May 12, 2007, pp. 1039-1050, vol. 15, No. 9.

Crowe, Colleen A.et al., Comparison of severity of illness scoring systems in the prediction of hospital mortality in severe sepsis and septic shock, Journal of Emergencies, Trauma, and Shock, Oct.-Dec. 2010, pp. 342-347, Oak Lawn, IL, USA.

Diep, Binh Anet al., Polymorphonuclear leukocytes mediate *Staphylococcus aureus* Panton-Valentine leukocidin-induced lung inflammation and injury, PNAS, Mar. 2010, pp. 5587-5592, vol. 107 No. 12.

Dojat, Michel et al., Scenario recognition for temporal reasoning in medical domains, Artificial Intelligence in Medicine, 1998, pp. 139-155, Elsevier Science B.V., Cedex, France.

Finlay, Heather et al., Designing and Testing a Computer-Based Screening System for Transfusion-Related Acute Lung Injury, Am J Clin Pathol, 2005, vol. 124, pp. 601-609.

Fry, Donald et al., The Changing Face of *Staphylococcus aureus*: A Continuing Surgical Challenge, Surgical Infections, 2011, vol. 12, No. 3, pp. 191-203.

Ghanem-Zoubi, Nesrin O. et al., Assessment of disease-severity scoring systems for patients with sepsis in general internal medicine departments, Critical Care, Retrieved from <http://ccforum.com/content/15/2/R95>, 2011, pp. 1-7.

Herasevich, Vitaly et al., Designing and testing computer based screening engine for severe sepsis/septic shock, AMIA Annu Symp Proc. Nov. 2008 (Abstract).

Herasevich, Vitaly et al., Enrollment into a time sensitive clinical study in the critical care setting: results from computerized septic shock sniffer implementation, J Am Med Inform Assoc, 2011, vol. 18, pp. 639-644.

Herasevich, Vitaly et al., Limiting ventilator-induced lung injury through individual electronic medical record surveillance, Crit Care Med, 2011, vol. 39, No. 1, pp. 34-39.

Herasevich, Vitaly et al., Validation of an electronic surveillance system for acute lung injury, Intensive Care Med., Jun. 2009, vol. 35, No. 6, pp. 118-1023.

International Preliminary Report on Patentability Including Written Opinion for International (PCT) Patent Application No. PCT/US2009/043150, dated Nov. 9, 2010 9 pages.

International Preliminary Report on Patentability including Written Opinion for International (PCT) Patent Application No. PCT/US2009/064312, dated May 31, 2011 10 pages.

International Search Report for International (PCT) Patent Application No. PCT/US2009/043150, dated Aug. 4, 2009 3 pages.

International Search Report for International (PCT) Patent Application No. PCT/US2009/064312, dated Feb. 26, 2010 4 pages.

International Search Report for International (PCT) Patent Application No. PCT/US2009/065124, dated Mar. 25, 2013, 10 pages.

(56) References Cited

OTHER PUBLICATIONS

International Search Report for International (PCT) Patent Application No. PCT/US2012/065129, dated Mar. 20, 2013, 12 pages.
International Search Report for International (PCT) Patent Application No. PCT/US2014/019577, dated May 28, 2014 (English) 11 pages.
International Search Report for International (PCT) Patent Application No. PCT/US2014/019587, dated Jun. 17, 2014 (English) 10 pages.
International Search Report for International (PCT) Patent Application No. PCT/US2014/019625, dated Jun. 17, 2014 (English) 18 pages.
International Search Report for International (PCT) Patent Application No. PCT/US2014/019637, dated Jun. 18, 2014 (English) 11 pages.
International Search Report for International (PCT) Patent Application No. PCT/US2014/019572, dated Jun. 26, 2014 (English) 9 pages.
International Search Report for International (PCT) Patent Application No. PCT/US2014/019556, dated Jun. 27, 2014 (English) 14 pages.
International Search Report for International (PCT) Patent Application No. PCT/US2014/019530, dated Jun. 27, 2014 (English) 11 pages.
International Search Report for International (PCT) Patent Application No. PCT/US2014/019442, dated Jul. 7, 2014 (English) 11 pages.
International Search Report for International (PCT) Patent Application No. PCT/US2014/019582, dated Aug. 28, 2014 (English) 12 pages.
Kellett, J. et al., The Simple Clinical Score predicts mortality for 30 day admission to an acute medical unit, QJ Med, 2006, vol. 99, pp. 771-781.
Kreisel, Kristen et al., USA300 Methicillin-resistant *Staphylococcus aureus* bacteremia and the risk of severe sepsis: is USA300 Methicillin-resistant *Staphylococcus aureus* associated with more severe infections?, Diagnostic Microbiology and Infectious Disease, 2011, vol. 70, pp. 285-290.
Lappin, Emma et al., Gram-Positive Toxic Shock Syndromes, The Lancet, May 2009, vol. 9, pp. 281-290.
Levy, Mitchell M. et al., 2001 SCCM/ESICM/ACCP/ATS/SIS International Sepsis Definitions Conference, Critical Care Medicine, 2003, pp. 1250-1256, vol. 31 No. 4.
Lu, K, et al., A Mathematical Program to Predict Survival and to Support Initial Therapeutic Decisions for Trauma Patients With Long-Bone and Pelvic Fractures, Injury, Mar. 2007, pp. 318-328.
Lynn, Lawrence A. et al., Patterns of unexpected in-hospital deaths: a root cause analysis, Retrieved from <http://www.passjournal.com/content/5/1/3>, Patient Safety in Surgery, Feb. 11, 2011, pp. 1-24, vol. 5, No. 3, BioMed Central.
MacKenzie, I.M.J., The Haemodynamics of Human Septic Shock, Anaesthesia, 2001, vol. 56, pp. 130-144.
MacLean, Lloyd et al., Patterns of Septic Shock in Man—A Detailed Study of 56 Patients, Annals of Surgery, Oct. 1967, vol. 166, No. 4, pp. 543-558.
Marik, Paul et al., The definition of septic shock: implications for treatment, Critical Care and Resuscitation, Mar. 2007, vol. 9, No. 1, Mar. 2007, pp. 101-103.
Marik, Paul, Surviving sepsis: going beyond the guidelines, Annals of Intensive Care, Jun. 7, 2011, 1:17, 6 pages.
Members of the American College of Chest Physicians/Society of Critical Care Medicine Consensus Conference Committee, Definitions for sepsis and organ failure and guidelines for the use of innovative therapies in sepsis, Critical Care Medicine, 1992, pp. 864-874, vol. 20 No. 6.
Nguyen, H. Bryant et al., Severe Sepsis and Septic Shock: Review of Literature and Emergency Department Management Guidelines, Annals of Emergency Medicine, Jul. 2006, pp. 28-54, vol. 48 No. 1.
Opal, Steven, The Uncertain Value of the Definition for SIRS, Editorial downloaded from www.journal.publications.chestnet.org/ on Nov. 19, 2013, pp. 1442-1443.
Patel, M.S.et al., Does the use of a "track and trigger" warning system reduce mortality in trauma patients?, Injury, May 25, 2011, doi:10.1016/j.injury.2011.05.030, pp. 1-5, Elsevier Ltd., United Kingdom.
Peres Bota, Daliana et al., Infection Probability Score (IPS): A method to help asses the probability of infection in critically ill patients, Crit Care Med, 2003, vol. 31, No. 11, pp. 2579-2584.
Rangel-Frausto MD, M. Sigfrido, The Natural History of the Systemic Inflammatory Response Syndrome (SIRS), JAMA, Jan. 11, 1995, vol. 273, No. 2, pp. 117-123.
Rivers, Emanuel et al., Early Goal-Directed Therapy in the Treatment of Severe Sepsis and Septic Shock, The New England Journal of Medicine, Nov. 8, 2001, vol. 345, No. 19, pp. 1368-1377.
Sawyer, Amber M. et al., Implementation of a real-time computerized sepsis alert in nonintensive care unit patients, Critical Care Medicine, 2011, pp. 469-473, vol. 39, No. 3.
Seigel, Todd et al., Inadequacy of Temperature and White Blood Cell Count in Predicting Bacteremia in Patients with Suspected Infection, The Journal of Emergency Medicine, 2010, pp. 1-6.
Shoemaker, WC et al., Hemodynamic and Oxygen Transport Monitoring to Titrate Therapy in Septic Shock, New Horiz., Feb. 1993, pp. 145-159, vol. 1, No. 1 (Abstract).
Shoemaker, WC et al., Invasive and Noninvasive Haemodynamic Monitoring of Acutely Ill Sepsis and Septic Shock Patients in the Emergency Department, Eur J Emerg Med, Sep. 2000, pp. 169-175, vol. 7, No. 3.
Shoemaker, WC et al., Pathophysiology of Adult Respiratory Distress Syndrome After Sepsis and Surgical Operations, Crit Care Med., Mar. 1985, pp. 166-172, vol. 13, No. 3 (Abstract).
Shoemaker, WC et al., Role of Oxygen Debt in the Development of Organ Failure Sepsis, and Death in High-Risk Surgical Patients, CHEST, Jul. 1992, pp. 208-215, vol. 102, No. 1.
Shoemaker, WC et al., Sequence of Physiologic Patterns in Surgical Septic Shock, Crit Care Med, Dec. 1993, pp. 1876-1889, vol. 21, No. 12.
Shoemaker, WC et al., Use of Sequential Physiologic Measurements for Evaluation and Therapy of Uncomplicated Septic Shock, Surgery, Gynecology & Obstetrics, Aug. 1970, pp. 245-254.
Shoemaker, WC, Cardiorespiratory Patterns in Complicated and Uncomplicated Septic Shock: Physiologic Alterations and Their Therapeutic Implications, Ann. Surg., Jul. 1971, pp. 119-125, vol. 174, No. 1.
Shoemaker, WC, Circulatory Mechanisms of Shock and Their Mediators, Crit Care Med., Aug. 1987, pp. 787-794, vol. 15, No. 8 (Abstract).
Shoemaker, WC, Temporal Hemodynamic and Oxygen Transport Patterns in Medical Patients, CHEST, Nov. 1993, pp. 1529-1536, vol. 104, No. 5.
Shoemaker, WC, Temporal Physiologic Patterns of Shock and Circulatory Dysfunction Based on Early Descriptions by Invasive and Noninvasive Monitoring, New Horiz., May 1996, pp. 300-318, vol. 4, No. 2 (Abstract).
Shoemaker, William et al., Role of Physiologic Monitoring in the Intensive Care Unit, Surgery Annual, 1970, pp. 61-81.
Shoemaker, William, Pathophysiologic Basis of Therapy for Shock and Trauma Syndromes: Use of Sequential Cardiorespiratory Measurements to Describe Natural Histories and Evaluate Possible Mechanisms, Seminars in Drug Treatment, Winter 1973, vol. 3, No. 3, pp. 211-229.
Shoemaker, William, Physiologic Mechanisms in Clinical Shock, Adv Exp Med Biol, Oct. 23, 1971, pp. 57-75.
Shoemaker, William, Sequential Hemodynamic Patterns in Various Causes of Shock, Surgery, Gynecology & Obstetrics, Mar. 1971, pp. 411-423.
Simmons, Daniel et al., Hyperventilation and Respiratory Alkalosis as Signs of Gram-Negative Bacteremia, JAMA, Dec. 31, 1960, vol. 174, No. 18, pp. 2196-2199.
Simmons, Richard, The Role of Central Nervous System in Septic Shock, Annals of Surgery, Feb. 1968, vol. 167, No. 2, pp. 158-167.

(56) References Cited

OTHER PUBLICATIONS

Stacey et al., Temporal abstraction in intelligent data analysis: A survey, Artificial intelligence in medicine, Jan. 31, 2007, vol. 39, pp. 1-24.
Subbe, C. P. et al., Validation of a modified Early Warning Score in medical admissions, Original Papers, Q J Med, May 17, 2001 and in revised form Jul. 9, 2001, pp. 521-526, vol. 94, Association of Physicians.
Sun, Dong et al., The Natural History of the Systemic Inflammatory Response Syndrome and the Evaluation of SIRS Criteria as a Predictor of Severity in Patients Hospitalized through Emergency Services, 1999, vol. 48, No. 1; pp. 28-37.
Tufte, Edward R., The Visual Display of Quantitative Information (Graphics Press, 1983), pp. 17, 21, 153.
U.S. Appl. No. 11/431,686, Amendment and Response to NF Office Action, Filed Jun. 21, 2011.
U.S. Appl. No. 11/431,686, Final Office Action, dated Oct. 12, 2011.
U.S. Appl. No. 11/431,686, Office Action (Restriction Requirement), dated Sep. 30, 2010.
U.S. Appl. No. 11/431,686, Response to Restriction Requirement, filed Oct. 29, 2010.
U.S. Appl. No. 12/437,385, Request for Continued Examination and Preliminary Amendment, Filed Feb. 7, 2012.
U.S. Appl. No. 12/437,417, Amendment and Response to NF Office Action, dated Nov. 5, 2012.
U.S. Appl. No. 12/437,417, Amendment and Response to NF Office Action, dated Sep. 6, 2011, 13 pages.
U.S. Appl. No. 11/431,686, U.S. Appl. No. 11/431,686, NF Office Action, dated Jan. 21, 2011.
U.S. Appl. No. 12/437,385, Amendment and Response to NF Office Action, dated Jan. 15, 2013.
U.S. Appl. No. 12/437,385, Amendment and Response to NF Office Action, dated Sep. 6, 2011.
U.S. Appl. No. 12/437,385, Final Office Action, dated Nov. 25, 2011.
U.S. Appl. No. 12/437,385, NF Office Action, dated Apr. 5, 2011.
U.S. Appl. No. 12/437,385, NF Office Action, dated Aug. 17, 2012.
U.S. Appl. No. 12/437,417, Final Office Action, dated Feb. 14, 2013.
U.S. Appl. No. 12/437,417, NF Office Action, dated Aug. 3, 2012.
U.S. Appl. No. 12/437,417, NF Office Action, dated Mar. 4, 2011.
U.S. Appl. No. 12/437,417, NF Office Action, dated Nov. 29, 2011.
U.S. Appl. No. 12/437,417, Request for Continued Examination and Preliminary Amendment, Filed Feb. 29, 2012.
U.S. Appl. No. 12/629,407, Amendment and Response to NF Office Action dated Sep. 25, 2012, filed Feb. 21, 2013.
U.S. Appl. No. 12/629,407, NF Office Action, dated Aug. 16, 2012.
U.S. Appl. No. 12/629,407, NF Office Action, dated Sep. 25, 2012.
U.S. Appl. No. 12/629,407, Response to Requirement for Restriction, filed Sep. 14, 2012.
Velmahos, George et al., Endpoints of Resuscitation of Critically Injured Patients: Normal or Supranormal?, Annals of Surgery, 2000, pp. 409-418, vol. 232, No. 3.
Wile, Michael J. et al., Manual Differential Cell Counts Help Predict Bacterial Infection, A Multivariate Analysis, Hematopathology, 2001, pp. 644-649, vol. 115, Am J Clin Pathol.
Herasevich et al., Designing and testing computer based screening engine for severe sepsis/septic shock, AMIA 2008 Symposium Proceedings, p. 864.
Herasevich et al., Enrollment into a time sensitive clinical study in the critical care setting: results from computerized septic shock sniffer implementation, J Am Med Inform Assoc. 2011, vol. 18, pp. 639-644.
Simon et al., Heat maps as a tool for large, in hospital database visualization for rapid hypothesis generation, Multidisciplinary Epidemiology and Translational Research in Intensive Care, Mayo Clinic, p. 1961.
Author Unknown, Wheel figure retrieved from the following website: http://www.getatomiq.com/content/images/faq/wheel.png, 1 page, viewed on Aug. 3, 2012.

Non-Final Office Action for U.S. Appl. No. 13/677,295, dated Apr. 8, 2015, 15 pages.
Non-Final Office Action for U.S. Appl. No. 13/844,381, dated Apr. 9, 2015, 21 pages.
Non-Final Office Action for U.S. Appl. No. 13/844,212, dated Apr. 9, 2015, 21 pages.
Non-Final Office Action for U.S. Appl. No. 13/844,404, dated Apr. 9, 2015, 18 pages.
Non-Final Office Action for U.S. Appl. No. 13/843,481, dated Apr. 9, 2015, 19 pages.
Final Office Action for U.S. Appl. No. 12/437,385, dated May 14, 2015, 31 pages.
Non-Final Office Action for U.S. Appl. No. 12/777,171, dated Mar. 5, 2015, 12 pages.
Non-Final Office Action for U.S. Appl. No. 14/193,757, dated May 8, 2015, 15 pages.
Non-Final Office Action for U.S. Appl. No. 14/193,376, dated May 29, 2015, 24 pages.
Fawcett, Tom, ROC Graphs: Notes and Practical Considerations for Data Mining Researchers, Hewlett-Packard Company, 2003, 28 pages.
Guven et al., Diagnostic Value of Procalcitonin Levels as an Early Indicator of Sepsis, Am JEmerg Med, 2002m pp. 202-206, vol. 20.
Haumptman et al., Evaluation of the Sensitivity and Specificity of Diagnostic Criteria for Sepsis in Dogs, Veterinary Surgery, 1997, pp. 393-379, vol. 26.
International Search Report for International (PCT) Patent Application No. PCT/US2012/065124, dated Jul. 23, 2015, 6 pages.
Rao, Singiresu, Engineering Optimization Theory: Advantages of Random Search Methods, 2009, pp. 314-317.
Sue Sendelbach & Marjorie Funk, Alarm Fatigue-A Patient Safety Concern, AACN Advanced Critical Care, vol. 24, No. 4, at 378-86 (2013).
Kelly Creighton Graham & Maria Cvach, Monitor Alarm Fatigue: Standardizing Use of Physiological Monitors and Decreasing Nuisance Alarms, American Journal of Critical Care, Jan. 2010, vol. 19, No. 1, at 28-34.
Brian Claise, Critical Response Systems, Inc. Alarm Fatigue and its Management Have Become Serious Healthcare Safety Issues. Copyright 2011-2014.
Richard J. Allen and Timothy C. Elston; "From Physics to Pharmacology?"; Department of Pharmacology, University of North Carolina at Chapel Hill, Chapel Hill, NC, US; Reports on Progress on Physics; Institute of Physics Publishing; vol. 74, No. 1; Dec. 3, 2010; pp. 1-19; stacks.iop.org/RoPP/74/016601.
Sergey M. Zuev, et al.; "Sepsis Progression and Outcome: A Dynamical Model"; Theoretical Biology and Medical Modelling, Biomed Central, Ltd.; London, GB; vol. 3, No. 1; Feb. 15, 2006; pp. 1-15; http://tbiomed.com/content/3/1/8.
PCT—International Preliminary Report on Patentability, for PCT application No. PCT/US2014/019530; dated Sep. 1, 2015; 8 Pages.
PCT—International Preliminary Report on Patentability, for PCT application No. PCT/US2014/019556; dated Sep. 1, 2015; 9 Pages.
PCT—International Preliminary Report on Patentability, for PCT application No. PCT/US2014/019572; dated Sep. 1, 2015; 6 Pages.
PCT—International Preliminary Report on Patentability, for PCT application No. PCT/US2014/019577; dated Sep. 1, 2015; 8 Pages.
PCT—International Preliminary Report on Patentability, for PCT application No. PCT/US2014/019637; dated Sep. 1, 2015; 8 Pages.
PCT—International Preliminary Report on Patentability, for PCT application No. PCT/US2014/019442; dated Sep. 1, 2015; 6 Pages.
PCT—International Preliminary Report on Patentability, for PCT application No. PCT/US2014/019582; dated Sep. 1, 2015; 7 Pages.
PCT—International Preliminary Report on Patentability, for PCT application No. PCT/US2014/019587; dated Sep. 1, 2015; 6 Pages.
PCT—International Preliminary Report on Patentability, for PCT application No. PCT/US2014/019625; dated Sep. 1, 2015; 15 Pages.
Non-Final Office Action issued in U.S. Appl. No. 12/629,407, dated Oct. 2, 2015, 19 Pages.

\* cited by examiner

RiseInWBC Script

Identify RiseInWBC as rise in WBC where ( candidate.PercentChange > 20 and candidate.magnitude > 4 )

Script-Level Severity Formula

WBC Rise slope .1/hour increasing by .1 for each severe range — 1920

WBC Rise magnitude 2 increasing by .5 for each severity range

WBC Rise min. 4 increase by .1 for each severity range

WBC Rise max 12 increases by .8 for each severity range

WBC Rise percent change 20% increase by 5% for each severity range

WBC Rise duration does not contribute to severity

FIG. 19

PATIENT STORM TRACKER AND VISUALIZATION PROCESSOR

This application claims the benefit of U.S. Provisional Application Ser. No. 61/770,919 filed Feb. 28, 2013, the contents of which are hereby incorporated by reference, and U.S. Provisional Application Ser. No. 61/770,971 filed Feb. 28, 2013, the contents of which are hereby incorporated by reference. This application is a continuation-in-part of U.S. patent application Ser. No. 13/677,295 filed Nov. 14, 2012, the contents of which are hereby incorporated by reference. This application is also related to U.S. patent application Ser. No. 14/193,700, filed Feb. 28, 2014, titled "Parallel Human Time Matrix Image of Causation," the entire contents of which are hereby incorporated by reference.

Human pathophysiology is highly complex and it is very difficult for physicians and nurses to timely detect sepsis in the many settings. U.S. Pat. Nos. 8,241,213, 8,152,732, 7,758,503, 7,398,115 and 7,081,095, as well as U.S. patent application Ser. Nos. 12/437,417, 12/437,385, 12/629,407, 13/677,291, and 13/677,288 (the entire contents of each of these applications are incorporated by reference as if completely disclosed herein) disclose processor methods, processing systems, and patient monitors for timely detection, identification, quantification, tracking, and generation of dynamic displays of sepsis and other conditions. These patents and applications provide additional background for the present subject matter.

U.S. patent application Ser. No. 13/677,295, entitled "Pathophysiologic Storm Tracker", filed Nov. 14, 2012 discloses processor based methods and processor systems in which displays of sepsis are presented metaphorically as dynamic images similar to color weather radar. The use of the color weather radar metaphor connects the user's knowledge about weather patterns which, like sepsis, may over time; grow, spread, worsen, move, morph into another condition, evolve, aggregate, disperse, improve, recover, recur and recover again across clinical and/or compartmental regions or spaces. These disclosed displays identify for example; onset, dynamic severity, dynamic progression, dynamic relationships to other events (such as medications) and/or procedures in a format which virtually all adults can readily understand. The use of the color weather radar metaphor takes advantage of the user's knowledge about dynamic processes to flatten the learning curve of sepsis dynamics. The color weather radar metaphoric images of sepsis and other conditions of the aforementioned techniques as well as the present techniques renders the complexity of sepsis more readily interpretable by those with limited training to empower a larger group of individuals (including the patient or the patients family) to enhance surveillance and mitigate the effects of a less than optimally attentive or trained healthcare worker.

BACKGROUND

SUMMARY

Embodiments of the present disclosure provide improved and alternative sepsis motion image visualizations.

BRIEF DESCRIPTION OF THE DRAWINGS

Various embodiments will be described hereinafter with reference to the accompanying drawings. These embodiments are illustrated and described by example only, and are not intended to limit the scope of the disclosure. In the drawings, similar elements may have similar reference numerals.

FIG. 19 depicts severity formulas used for deriving severity profiles.

DETAILED DESCRIPTION SPECIFIC EMBODIMENTS

Figure 1:
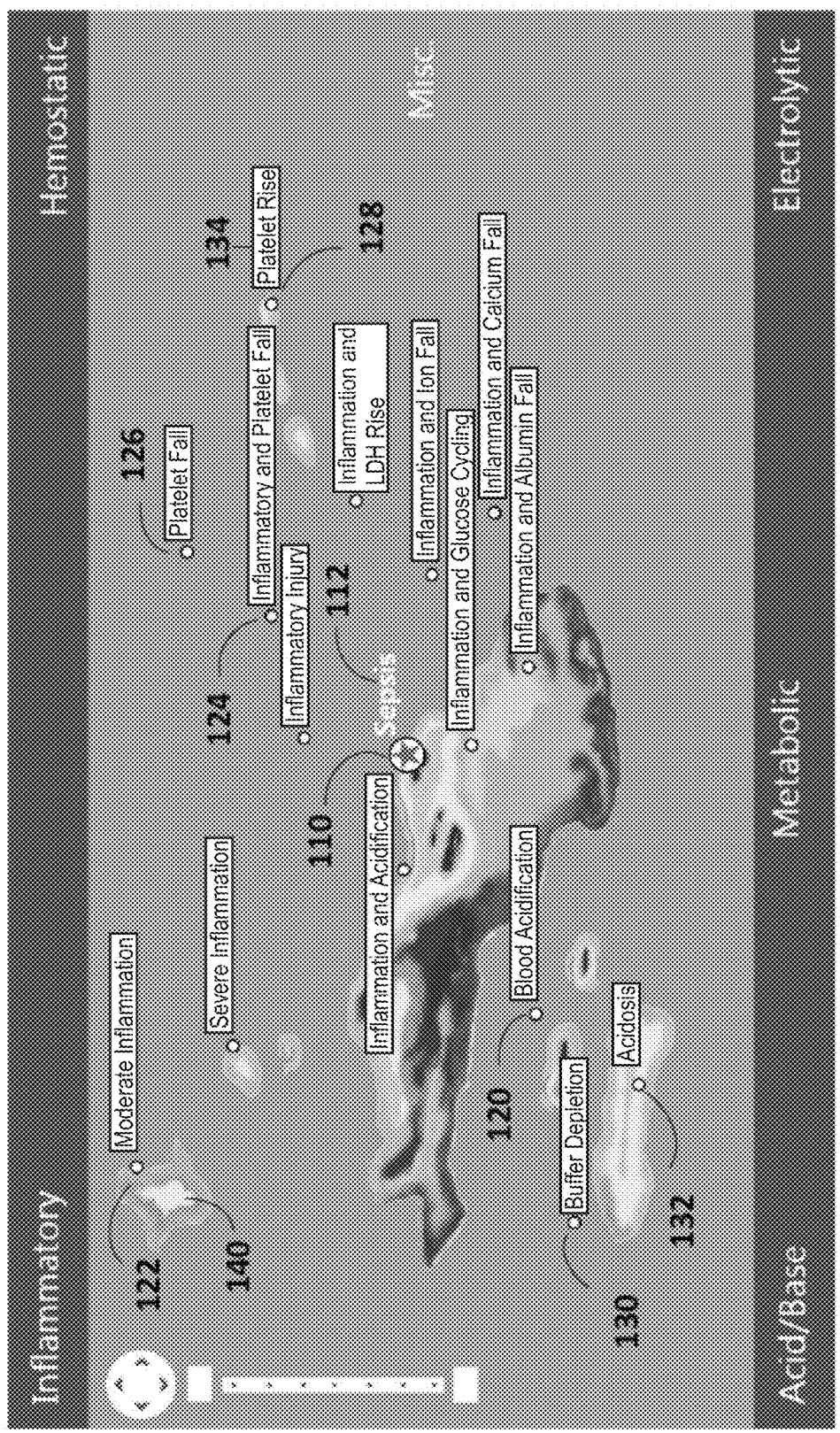
FIG. 1 depicts a condition-centric storm tracking map for sepsis for a single patient shown at a specific point in time.

In one embodiment, the processor is programmed to provide processing systems and methods which generate visualizations of dynamic pathophysiologic cascades of perturbation of the densities of biologic particles and recoveries of the densities of biologic particles (and particularly cascades of perturbations and recoveries of densities of biologic particles induced by sepsis), along with associated individual, relational and cascades of the forces inducing the perturbation and the forces inducing the recoveries of the densities, and for presenting the cascades of the perturbations and recoveries as well as the perturbation forces and recovery forces in a motion picture responsive to or indicative of cascades of perturbation, which may be linked to cascades of perturbation inducing forces, which may be linked to cascades of recoveries, and which may be linked to cascades of recovery inducing forces.

The processing of binaries, the temporal and spatial relationships of the components of the binaries, the temporal and spatial relationships of the binaries themselves, and the temporal and spatial relationships of reciprocations, images, and cascades derived of linked binaries is discussed in detail in the aforementioned patent application and in the co-filed patent application filed Feb. 28, 2013, entitled "Programmatic Human Matrix" (the entire contents of each of these applications are incorporated by reference as if completely disclosed herein).

As described in application Ser. No. 13/677,295, one visualization format is similar to a color radar weather map of the type commonly viewed by most Americans on the evening news during common rain, snow, or thunderstorms, as well as during hurricanes and tornadoes. This provides a dynamic visualization of a complex sepsis cascade, for example, as a "patient storm" with the visualized patient storm dynamically spreading across the geographic space which represents the various systems of the human body. The term patient storm refers to a patient pathophysiologic condition, failure, or complication, such as sepsis which characteristically progresses in a progressive and expansive manner potentially involving a progressive number of systems. The storm metaphor provides the cues that can greatly shorten the learning curve for the healthcare professional to allow them to readily see and perceive the characteristics of the dynamic nature of an expanding cascade of sepsis which has proven otherwise very difficult for them to learn and understand. In one embodiment these workers see the dynamic and relational patterns of complexity of sepsis in evolution as they would for a major storm spreading across North America. In one embodiment, the metaphorically presented patient storms, like weather storms, have patient storm components like patient storm cells, patient storm fronts, patient storm origins, patient storm expansions, patient storm movement, and patient storm contraction and/or recovery. Multiple patient storms of one or more types may also be visually presented in relation to each other. According to one embodiment, computational transparency is provided either automatically or upon a healthcare worker gesture (as with auditory, textual, touch, natural interface actions or mouse over to name a few) so that the healthcare worker can look inside a patient storm front or a patient storm cell for example to see which relational pathophysiologic perturbations which were identified or detected by the processor to generate patient storm components.

According to one embodiment patient storm cells may be derived from the alpha events and the beta events of the image binaries, or the image binaries themselves. In the alternative, or in addition, the patient storm cell may be derived from the beta events, alpha events, sigma events and tau events of the perturbation and recovery force binaries or of the force binaries, coupled binaries, quaternaries, and/or cascades themselves. In this way the display may generate dynamic motion images of the relational patient storm cell as well as dynamic motion images of the relational forces which induced the patient storm cells.

Figure 2:
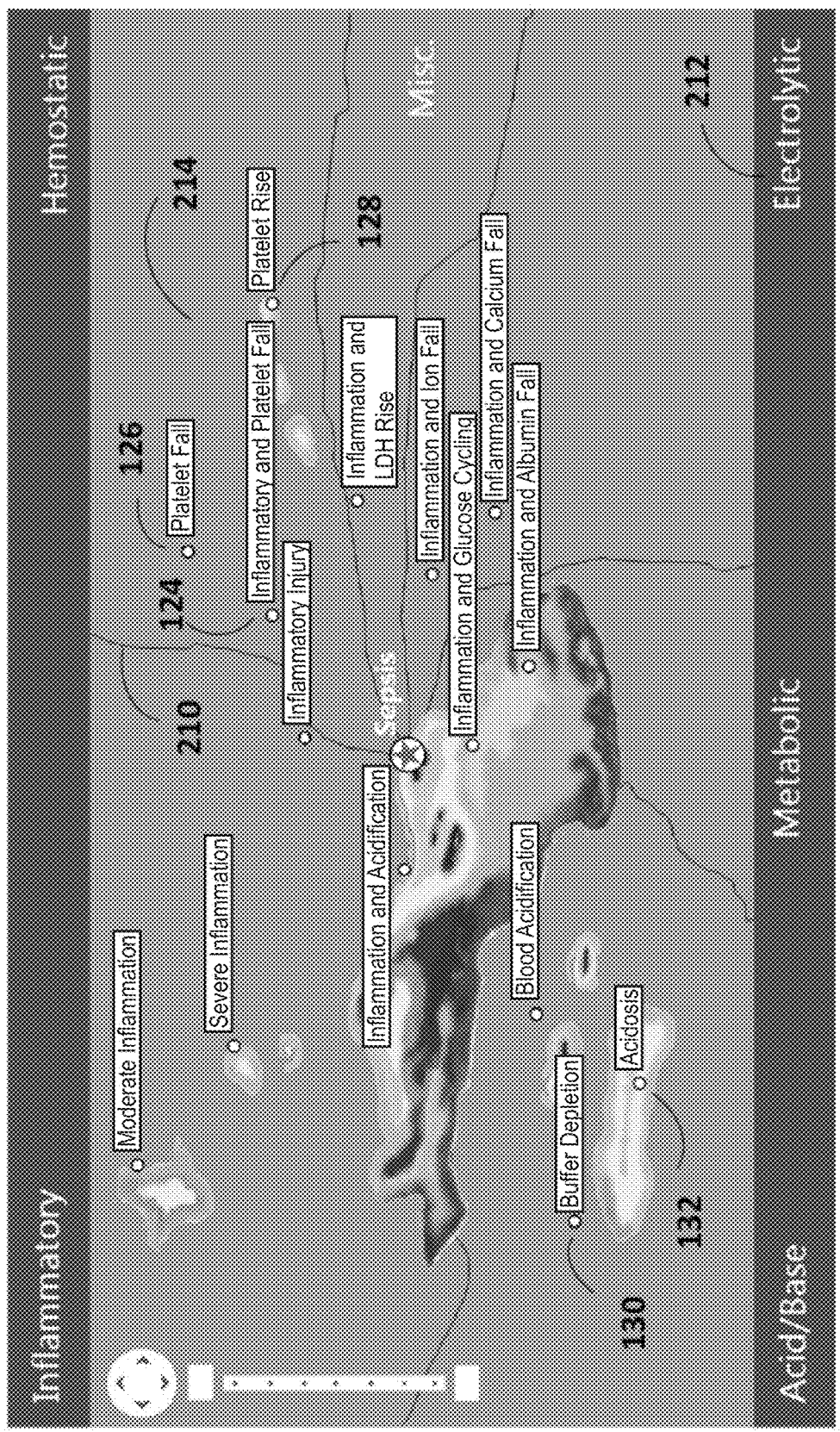
FIG. 2 depicts a condition-centric patient storm tracking map for sepsis including the borders of clinical space for clarification.
Figure 3:
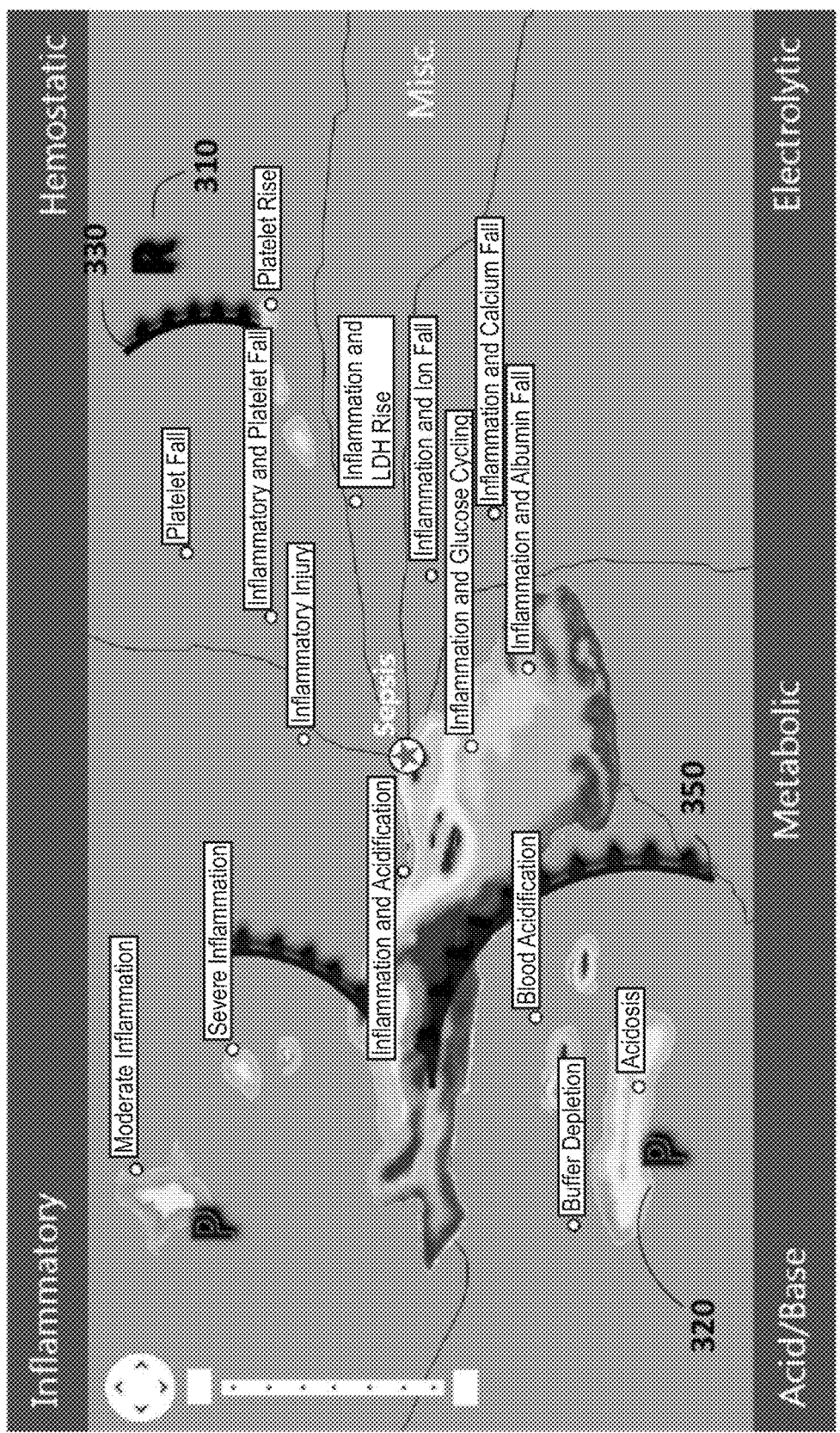
FIG. 3 depicts a condition-centric patient storm tracking map for sepsis including both clinical space borders and patient storm overlays depicting areas of increasing perturbation and areas of recovery.

In the present embodiment, FIG. 1 shows an example of a Patient storm Tracker and Visualization Processor (PSTVP) visualization which utilizes the weather metaphor to present the state of a patient specifically associated with a patient condition—in this case sepsis. FIG. 1 is a condition-centric map for sepsis. FIG. 2 and FIG. 3 provide additional examples showing features which may or may not be shown on the map or may be visible according to user preference.

The condition-centric map is made up of three layers—the background, the weather and overlays. The background is static across patients and provides a common "geography" over which perturbation flows. The second and third layers (weather and overlays) are both patient and time specific. Animation shows the change in the top two layers over time showing perturbation data emerging, moving, growing, changing color and being labeled with iconic overlays creating a moving picture of the dynamic evolution of the condition in time.

The background of the condition-centric map is condition-specific. In the present embodiment a map is created for each condition for which the PSTVP system is monitoring. In an alternative embodiment, a single map is used with multiple conditions. In the present embodiment, the central element, a circle with a star 110, is labeled with the condition 112 and represents the specific condition for which this map has been constructed. This iconic representation taps into the common metaphor of a capital city 110. Optionally, as in FIG. 2, lines 210 radiate from the central element to the edge of the visualization to create triangular or roughly triangular shapes that represent the clinical spaces. These spaces are labeled 212 at the edge (e.g. Inflammatory, Acid/Base). Alternatively, a roughly circular area surrounds the central element and the lines delineating clinical space proceed from this line rather than from the central element itself. In the present embodiment, the radiating lines 210 are not straight but have an irregular shape tapping into the metaphor of borders (e.g. country, state or county borders) within a weather map. In an alternative embodiment, the radiating lines are straight or smoothly curved. In FIG. 2 the irregular lines are shown and the clinical spaces are labeled 212 around the perimeter of the visualization. In an alternative embodiment, the capital city is in the right-most position with the map extending out in a conical fashion from left to right. The central element 110 may be responsive to the detection of the patterns. For example the central element 110 may be initially missing or almost invisible, and then become visible or more visible or otherwise highlighted when sufficient pattern components have been identified to warrant display of the central element 110.

In one embodiment, the background is further made up of individual circles 120 representing sub-conditions within the central condition 110. For example, as shown in FIG. 1, Blood Acidification 120 is shown as a sub-condition within the Acid/Base clinical space. These circles tap into the metaphor of cities within a weather map. Sub-conditions may, for example, be occurrences, relational occurrences, trends, relational trends, threshold violations, relational threshold violations, and a wide range of combinations of these as for example described in the aforementioned patent applications. In an example during a sepsis patient storm moderate inflammation 122 may be combined with a fall in bicarbonate to form one sub-condition and with a fall in platelets to form another sub-condition 124 (each which may be designated on the map as a circle or city). Cities, representing sub-conditions, are placed with respect to the clinical space areas. For example, in FIG. 2, the Hemostatic space 214 contains three cities—"Platelet Fall" 126, "Platelet Rise" 128 and "Inflammatory and Platelet Fall" 124. Further, placement within the clinical space area may also be chosen with respect to the relationship to other clinical spaces and/or sub-conditions.

Figure 4:
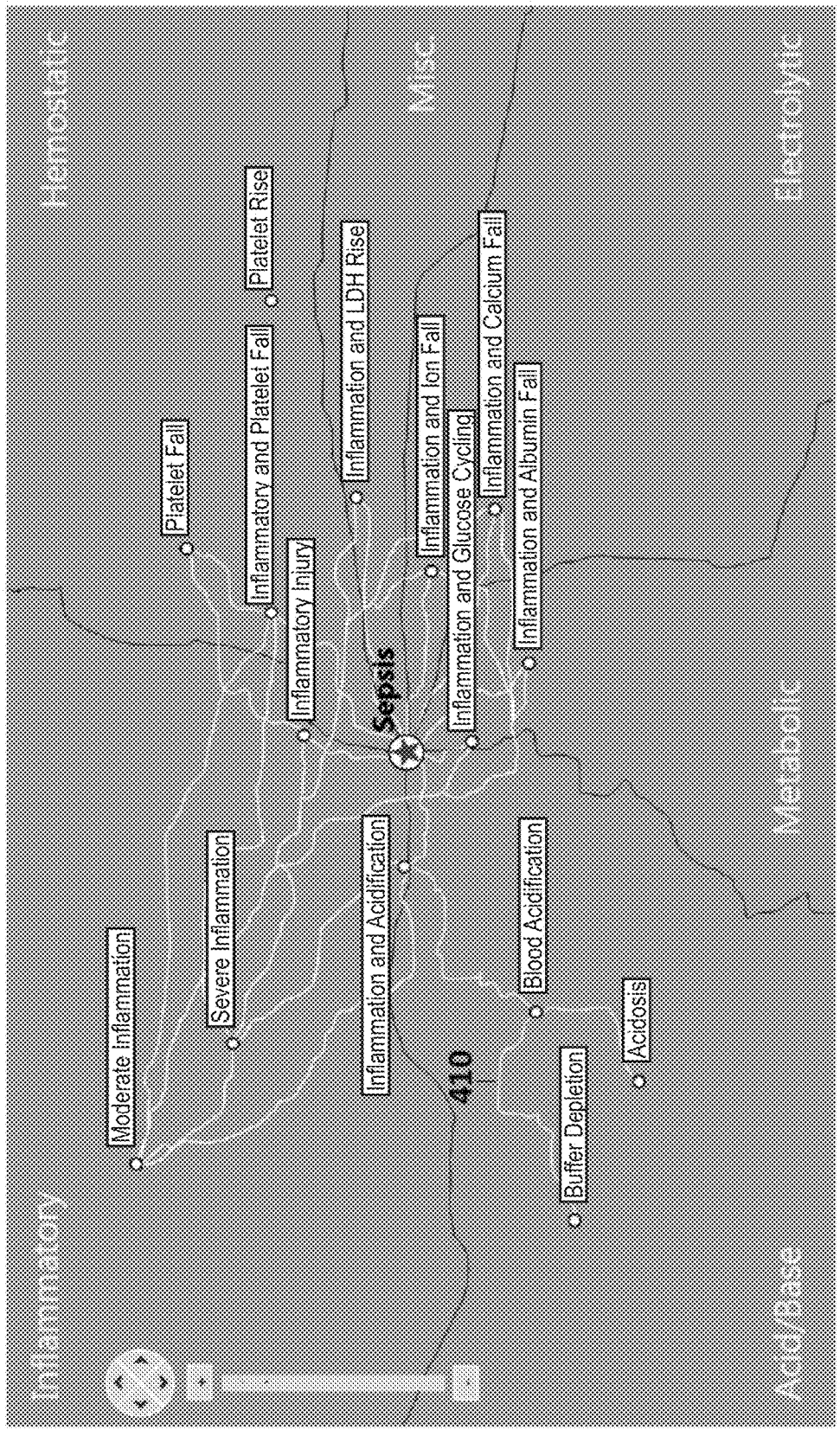
FIG. 4 is a condition-centric patient storm tracking map background for sepsis showing pattern relationships.
Figure 5:
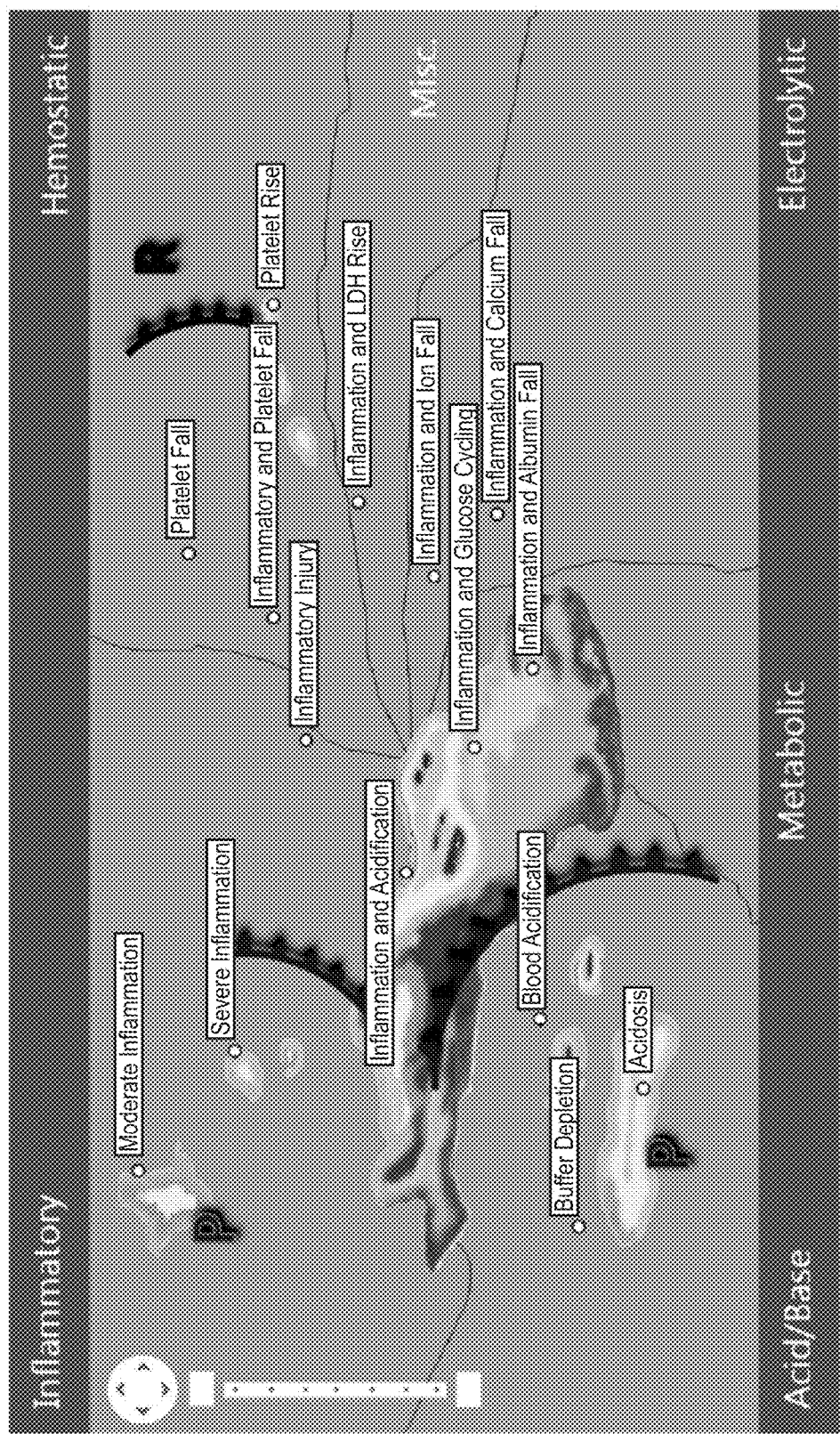
FIG. 5 depicts a general patient condition map without reference to a specified condition.

In one embodiment, sub-conditions are represented by pattern scripts written in PDL as for example described in the aforementioned patient applications. A sub-condition may be a single pattern (e.g. Platelet Fall) or a pattern made up of several other patterns (e.g. Blood Acidification). A city may be related to another city within the map. For example, Blood Acidification 120 is a classification that can be either Buffer Depletion 130 or Acidosis 132. This opportunity for relating cities creates an integrated relational network of patterns. In one embodiment, the relationship between cities is shown on the background. In FIG. 4 the relationships between cities 410 are shown. In one embodiment, the visibility of these relationships is toggled in response to a user gesture.

Cities, representing sub-conditions, are labeled 134 (as seen in FIG. 1) and are part of the background of the map and therefore are fixed in position during presentation to the healthcare worker. The initial placement of the cities can be determined by several factors including statistical correlation to the condition, disease stage, disease progression, disease severity, and by relationship to region and/or other cities to name a few. However the value may be any of a number of correlativity metrics relating to probability assessment. In at least one discussion specificity is shown to provide an example of one correlativity metric.

The PSTVP provides a visual map editor with which an expert can construct a map.

The background as a whole—the central element 110, the clinical space borders 210 and areas 214, the cities 126 and optionally the relationship between cities 410 are displayed along with their labels to provide a fixed geography over which perturbation flows. Familiarity with these positions on the map helps to provide a context which can be assimilated as a whole providing rapid cognition.

The next layer for the condition-centric map is the weather layer. This layer displays perturbation flowing over the background to tap into the metaphor of weather flowing over a familiar geography. In the present embodiment, each city has a script associated with it. Within that script are one or more sub-scripts or statements representing possible occurrences within the sub-condition. From these scripts, both the scripts for the city, and all of the associated sub-scripts an associated patient storm cell is derived. For example, the city "Moderate Inflammation" 122 (shown in FIG. 1) is defined with the following PDL: identify ModInflammatoryIndicator as RiseInWBC or RiseInNeutrophils or LowWBC or FallInNeutrophils or HighWBC or HighNeutrophils or LowNeutrophils. The city "Moderate Inflammation" 122 is associated with this classification "ModInflammatoryIndicator." This means that ModInflammatoryIndicator has seven sub-scripts each containing a different pattern which the PSP system is monitoring in real time. If any occurrences are identified within those sub-scripts then perturbation will be presented on the map as a patient storm cell 140.

The dynamic transition of infection to inflammatory augmentation to sepsis is very a complex dynamic process. To engage complexity one embodiment provides a multidimensional severity and progression indicator, called a patient storm cell 140, one embodiment of which is shown 850 in detail in FIG. 8. The patient storm cell 850 is a collection of colored hexagons placed within the weather layer of the weather map, in this case a condition-centric map. In an alternative embodiment, other visual elements are used including grey-scale hexagons, textured hexagons, pixels, other fixed or variable geographic shapes, fractals, and/or circles to name a few. In one embodiment, a series of transformations are executed including geometric, texture and finishing transformations to name a few. The collection of hexagons 850 is determined from a metric profile of the associated city. In the current embodiment, severity is used as the metric from which the profile is created. In an alternative embodiment, other metrics are used including occurrence count, statistical measures, and relational metrics to name a few. This may be used to generate an alternative weather map wherein the relative probability of a condition is substituted for severity (as described herein) to generate the weather movement expansion and severity. Similarly expense may be used to generate the weather with the relative expense associated with each cascade portion and cell is substituted for severity (as described herein) to generate the weather movement expansion and severity. The user may toggle between the severity map and the probability map and the expense map, or the maps be overlaid, for example as transparencies, or otherwise integrated with different colors, shapes, or icons, and shown together.

In the present embodiment severity is defined in terms of severity modes. The severity modes comprise the severity of each of the different properties of each occurrence or relational occurrence as well as relational modes in which properties and/or occurrences are considered in context of other properties and/or occurrences. For example an occurrence may be a Rise in White Blood Cells (WBC rise), properties of the WBC rise may, for example, comprise a WBC rise slope, WBC rise magnitude, WBC rise percent change, and WBC rise duration, WBC rise minimum value, WBC rise maximum value, WBC rise in relation to the normal range, to name a few. Each of these properties may comprise a severity mode for the occurrence WBC rise.

Figure 20:
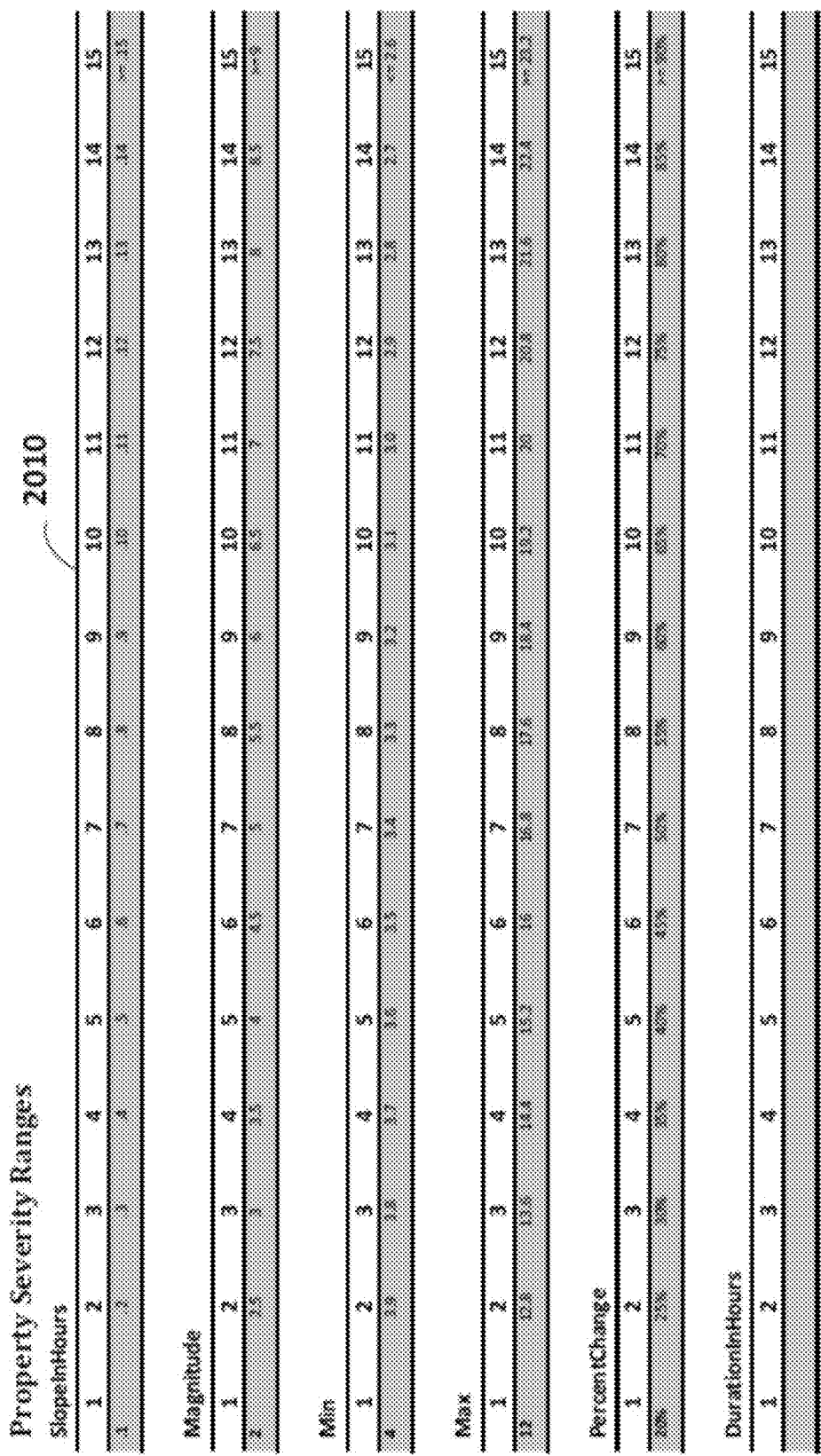
FIG. 20 depicts range-based entry tables used for deriving severity profiles.
Figure 21:
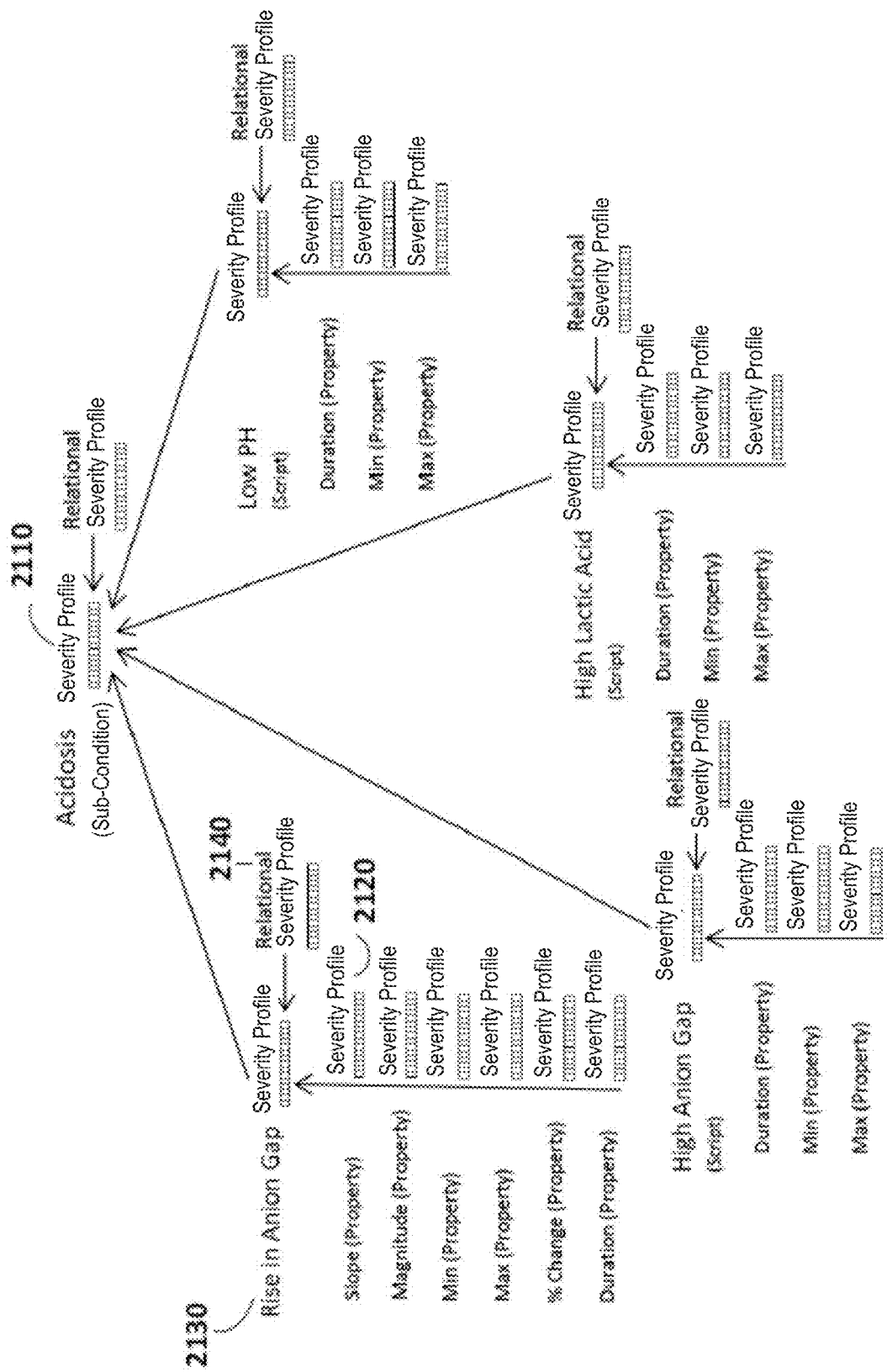
FIG. 21 is an aggregation diagram showing how the severity profile for a patient storm cell is aggregated from all of the elements, sub-elements and their relationships.

An occurrence may have a high severity by one mode (one occurrence property) and a low severity by another severity mode (one occurrence property). This embodiment provides the ability to define severity variation with a high level of relational granularity across many severity modes applicable to each occurrence and therefore provides an output which more closely matches the true pathophysiologic complexity. This provides the ability to detect the subtle, insidious, and highly variable relational foci of progression and/or relational foci of progression which characterize the transition from simple infection to early sepsis, and then from early sepsis to more severe states. In an example a single severity mode, such as a WBC rise maximum value of 11 may be of low severity but if the rise was rapid so that the WBC slope was high (for example 0.8/hr), or if it was of high magnitude (for example 6.4), then each of these severity modes will trigger a higher severity in their pixels of the visualization to warn that, while the WBC is still normal, dynamic changes are in progress. Furthermore the use of a wide range of severity modes allows more robust protocolization. In the above example, the processor may not be programmed to take any action in response to a WBC of 11 but based on the combination of a high slope and high magnitude severity may be programmed to order a repeat WBC in 4 hours to determine if the WBC rise is continuing. As noted previously this is one aspect of the present embodiment provided to solve the problem of oversimplification of the complexity which is causing so many late detections and deaths. In one example a first gradation of severity used for each severity mode is defined as an integer between 0 and 15. The profile is an array of cells 860 made up of fifteen slots representing the count of severity values matching the integer values. For example, a profile {0,3,0,6,0,0,0,0,0,0,0,0,0,0,0} indicates 3 instances of severity value 2 and 6 instances of severity value 4 and no other severity instances. In the present embodiment, for each patient each city has a severity profile for a given point in time within the patient stay. All of the scripts associated with a city feed into the severity profile, as shown in FIG. 21. For example, for the Moderate Inflammation city 122 described above there are 7 patterns being monitored and each of those patterns may identify one or more instances of an occurrence of that pattern. For example, a patient may exhibit two instances of FallInWBC, an instance of LowWBC, and an instance of LowNeutrophils. In this case there are 3 patterns identified and 4 instances. For each of the instances the severity of the instance can be derived. For example, the two instances of FallInWBC may be a severity 2 instance followed by a severity 6 instance while the LowWBC may be a severity 4 and the LowNeutrophils may be a severity 6. In this case, given only the severity of the instances of the sub-scripts we would derive the profile {0,1,0,1,0,2,0,0,0,0, 0,0,0,0,0}. Further, individual properties of the instances can further contribute to the severity profile. For example, the slope of the fall of the instances of the FallInWBC may be considered severity 7 and 3 respectively whereas the duration of the LowWBC may be considered severity 3 and the duration of the LowNeutrophils may be considered severity 4. In this case the severity profile would now be {0,1,2,2, 0,2,1,0,0,0,0,0,0,0,0}. The derivation of severities from properties is illustrated in FIGS. 19 through 21. FIG. 19 depicts a formulaic approach in which severities for individual properties can be derived from a formula 1920, expression or script of a Domain Specific Language (DSL) to name a few. FIG. 20 depicts another method that can be used independently or in concert by specifying ranges per severity cell 2010. FIG. 21 depicts how severities are "rolled-up" into a single patient storm cell 2110. Other attributes of the scripts, the instances, the aggregation of instances, relationships of the instances, preexisting conditions of the patient, the properties of the instances, aspects of the aggregation (e.g. average) to name a few may contribute to the severity profile of the city 2110 and therefore can contribute to the size, shape, color distribution and other aspects of the associated patient storm cell.

As shown in FIG. 21, each severity mode translates into a severity profile. For example, as shown in FIG. 21, the slope property of the Rise In Anion Gap has a severity profile 2120. In the present embodiment, a single property of a single occurrence of Rise In Anion Gap such as the slope property would be given a single value of severity (in one embodiment, derived from a table of ranges as shown in FIG. 20). Therefore, each property of each occurrence of a pattern type (e.g. Rise in Anion Gap) would have a severity mode and would provide a single profile value (e.g. a count of 1 in one of the 15 cells within a severity profile). Severity profiles can be aggregated together. In the present embodiment, severity profiles are aggregated by adding the values in the respective cells. For example, a profile {0,1,0,1,0,0, 0,0,0,0,0,0,0,0,0} aggregated to a profile {0,1,0,0,0,0,0,0,0, 0,0,0,0,0,0} would yield {0,2,0,1,0,0,0,0,0,0,0,0,0,0,0}. All severity modes are added together to generate a high-level severity profile 2110 from which a patient storm visualization can be derived. As shown in FIG. 21, each occurrence type (e.g. Rise In Anion Gap 2130) can have several properties. Each property is analyzed for severity using, in one embodiment, tables as shown in FIG. 20 or expressions as shown in FIG. 19. For each property of each instance (occurrence) of each occurrence type the severity is calculated and a single-entry profile is created. All of these single-entry profiles are rolled up into the occurrence type profile. Further, for each occurrence (an instance of an occurrence type) a relational severity profile 2140 is also derived (as shown in FIG. 21). The relational severity profile is calculated by evaluating one or more severity expressions attached to the script which defines the occurrence type (e.g. Rise In Anion Gap). Expressions created within the occurrence script allow for the properties of a single instance to be evaluated in context for relational severity. Within the micro-domain of the identified pattern relational severity can be evaluated. Within the context of a simple event (e.g. Rise In Anion Gap) this consists primarily of an evaluation of relationships between the properties of the event, but within the context of more complex patterns (binaries, images, etc.) the evaluation can include the comparison of properties of two or more occurrences which make up the overall pattern.

Occurrence types, then, as shown in FIG. 21, provide context-specific opportunities to identify relational severity. These opportunities, in the present embodiment, are exploited by the use of severity expressions within the script which result in individual severity values (e.g. between 1 and 15) that are wrapped up and aggregated into severity profiles that can participate in the general roll-up of severity as shown in FIG. 21.

In the present embodiment, the aggregation of severity profiles (as shown in FIG. 21) are additive in the sense that all severity modes are rolled up into the patient storm. Individual instances of severity are not averaged, filtered or otherwise processed in a way in which individual pixels are lost.

Severity profiles provide a flexible and powerful mechanism for capturing a complex set of severity results. The severity profile and the patient storm visualization correspond in their ability to contain and communicate pathophysiological complexity. Within a patient storm, there may be local intensity which may not dominate the overall patient storm. An observer, using high-level weather maps can identify the local phenomenon and recognize that they may represent nascent intensity which may be a precursor to overall patient storm intensity or may rather be transitory and therefore anomalous. Algorithms which roll up information into a single value or "score" fail to accomplish this. For example, if a "maximum" strategy is imposed then a local phenomenon will be blown up to be global and represent the present condition in a way that is misleading. If threshold mechanisms are employed then the local phenomenon is hidden until a critical mass is attained creating the situation in which researchers have the hopeless goal of finding "just the right threshold" which can provide early detection without generating alarm fatigue. The severity profile has the ability to contain a massive amount of information in a simple data structure. The weather map as well has the ability to contain a massive amount of information while simultaneously providing the ability, through the link to a common metaphor, to provide information rapidly and even pre-attentively about the size, direction and intensity of a complex cascade.

In the present embodiment, the severity profile data structure further contains the referential information to quickly identify the source of each pixel of severity to facilitate mechanisms of computational transparency.

In one embodiment of the PSTVP the severity profile is a data structure which contains a set of cells corresponding to severity levels 860. Additionally, the profile itself provides properties such as maximum severity, minimum severity, perturbation volume, perturbation distribution, perturbation spread to name a few. Maximum severity indicates the highest cell with a non-zero entry. Minimum severity indicates the lowest cell with a non-zero entry. Perturbation volume is an aggregation of all the counts in all cells. The perturbation distribution is an expression of how counts are distributed across the set of severity levels while the perturbation spread is the number of cells between the minimum and the maximum inclusive. These metrics further support the analysis and comparison of patient storms and patient storm elements and can be accessed both instantaneously and as a time series. For example, the time series of perturbation volume provides an indication of the gross level of evidence of perturbation while the change in distribution provides a powerful characterization of a patient storm.

Figure 8:
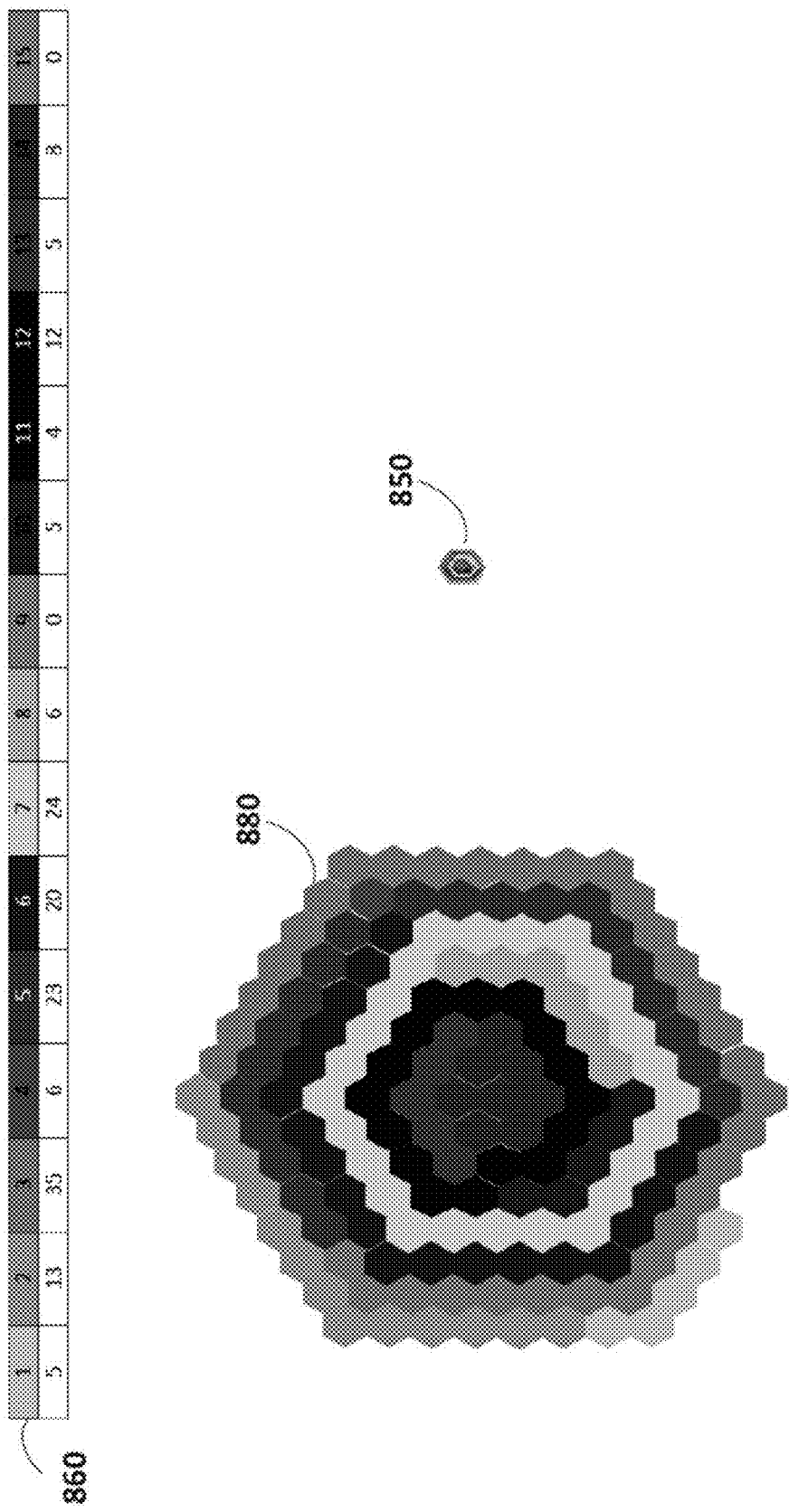
FIG. 8 depicts a hexagon-based patient storm cell derived from a severity profile.
Figure 9:
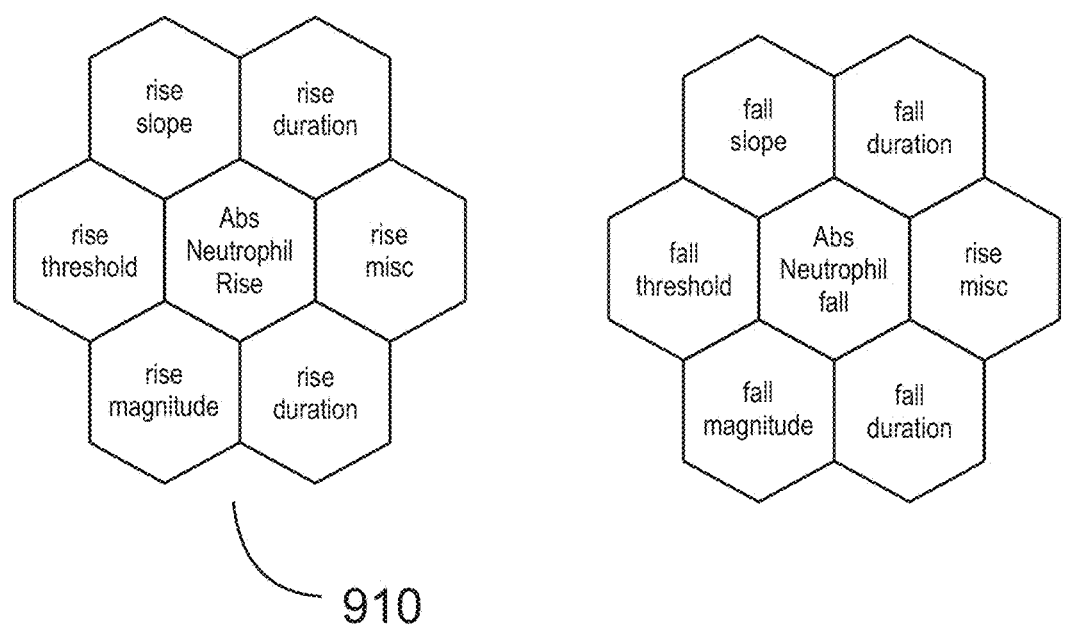
FIG. 9 depicts a property-level hexagon sub-visualization.

In the present embodiment, the PSTVP translates the derived severity profile of a city into an initial patient storm cell visualization. FIG. 8 shows an example of this translation. The hexagon figure on the left 880 is enlarged to show the detail. Each cell within the severity profile is assigned a color. The count within the cell translates to the number of hexagons used. The cell severity value determines the color of those hexagons. In one embodiment a multiplier is used such that the number of hexagons is increased in a proportional manner from the initial counts. In one embodiment the hexagons are placed starting with the most severe in the center and then moving in a spiral fashion outward 880. The severity-centric display emphasizes the metaphor of a patient storm cell. In one embodiment the cells in the severity profile represent rings in a circle and the count within the cell determines or roughly determines the width of the ring. In one embodiment, groups of hexagons 910, as depicted in FIG. 9 are used. In the present embodiment the patient storm cell directly derived from the severity profile does not represent the final visual representation on the weather layer of the condition-centric map. The patient storm cell visual is the initial representation that will be altered by other conditions within the map before being rendered within the weather layer.

In the present embodiment, once the initial representation of the patient storm cell has been completed several other steps are taken before the cell is rendered on the weather layer. Those steps include move, distort, merge and finish. In an alternative embodiment other means to modify the patient storm cells to improve visualization may be used.

Figure 10:
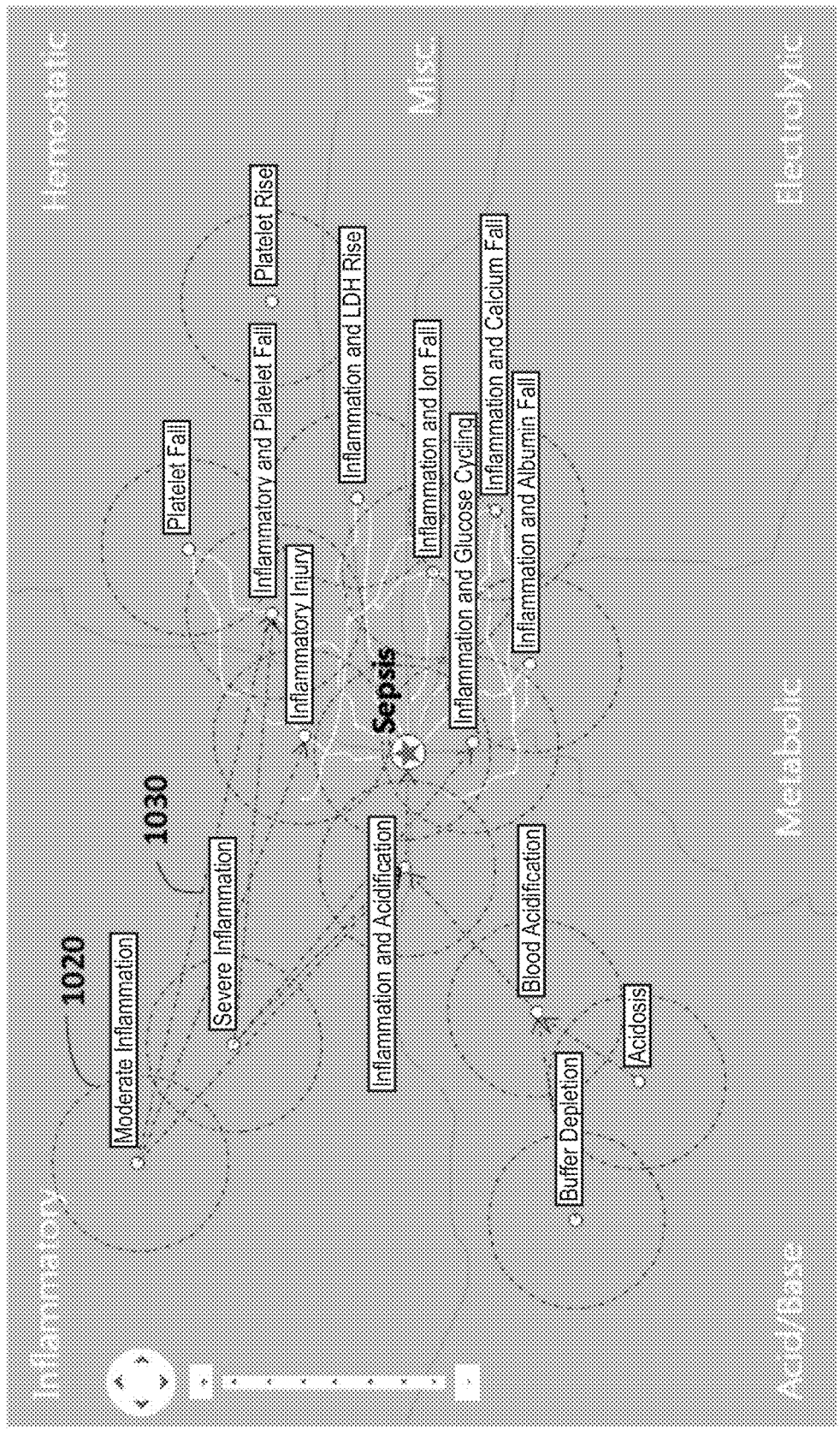
FIG. 10 is a force and limit diagram for a condition-centric patient storm tracking map for sepsis.

Patient storm cells represent a level of perturbation within a clinical space. The region associated with the clinical space can have many patient storm cells presented. If a city has any perturbation (as represented by a number>0 in a cell of a severity profile) an associated patient storm cell will be placed on the map. The location of a patient storm cell is the result of multiple factors. A patient storm cell location is first determined on the basis of the city itself but then is altered by the "pull" of related cities on the map. In the present embodiment, the initial placement on the map is determined by the location of the city, a vector between the city and the central element 110 (e.g. Sepsis) and a circle around each city 1020 called the limit perimeter. Each city has a limit perimeter which is defined as a circle around the city with a specified radius. These limit perimeters are shown in FIG. 10. In one embodiment the limit radii are equal for all cities. In alternate embodiments, the radii are different for some of the cities, or for each city. The initial location of the patient storm cell is selected as the point of intersection between a vector drawn from the center of the central element through the center of the city and bisecting the limit perimeter at the farthest point of the perimeter away from the central element. This point identifies the initial point of the patient storm cell. If no other alterations were applied, then the patient storm cell would be placed by putting the center point of the patient storm cell visualization on this initial point.

In the present embodiment, once the initial point is established, forces are applied to reposition the patient storm cell according to related cities on the map. In the present embodiment, the PSTVP includes a physics engine which models forces on the map. In this way, cities pull patient storm cells of the cities to which they are related with a force proportional 1030 to the severity profile derived of the associated city. For example, for a given city once an initial patient storm cell location point is determined then the PSTVP identifies all of the cities that are related to the city are identified. For each related city a pull force 1030 is determined by the "weight" of the associated severity profile. The direction of this pull force is determined as the direction of a line starting at the current city drawn to the related city (as shown on FIG. 10). The potential location of the patient storm cell is then calculated by aggregating the forces applied (and setting a specified constant simulated value for time). Finally the perimeter limit is applied to limit the location of the center. In other words, if the potential location is located outside of the limit perimeter then the final location is determined as the point where a line between the initial point and the potential point bisects the limit perimeter. This point then becomes the central point of the patient storm cell. In one alternative embodiment there is no limit perimeter. In one alternative embodiment the combination of the severity profiles between the current city and the related city is used to determine the force. In one alternative embodiment the central element 110 applies a minimum force regardless of whether the script associated with the central element has a non-zero severity profile. In one embodiment, the physics engine is tuned per condition to alter the way that elements are moved, distorted and/or merged specifically for the target condition (e.g. Sepsis or CHF).

Once the final location is determined for the patient storm cell then further alterations are applied. These alterations may include residual visualization, force distortion and patient storm cell merge to name a few. Residual visualization is the process of providing a visual "residue" of the patient storm path as determined by the forces which apply. In the present embodiment, a residue area is determined by calculating the location of the patient storm cell from the initial location to the final location with a given time granularity of the transition. For example if the granularity were determined to be 10 then the patient storm cell would be set at the initial location and then 8 locations between the initial location and the final location and then finally the final location. A perimeter can then be determined around all of these patient storm cells to create the residue area. Within the residue area a visualization of severity is placed by using the minimum severity and a coverage value determining how completely to fill in the residual area. In an alternative embodiment other severities are included. In an alternative embodiment the residual is created by combining the patient storm cell visualizations along their path from the initial to the final location. The residual visualization streams behind the patient storm cell visualization to form a single visualization.

In the present embodiment, force distortion is also applied to the patient storm cell visualization. The forces, as described above, are applied to the initial patient storm cell shape to generate a distortion. In one embodiment the distortion is created by aggregating the forces and "pulling" the patient storm cell shape as if it were an elastic enclosure around fluid. In one embodiment this "pulling" is done at each of the angles at which the relational force is applied. In the present embodiment the distorted shape is then used to generate the patient storm cell. In an alternative embodiment, the forces pull individual hexagons away from the patient storm cell creating a separation from the patient storm cell. Each individual hexagon is pulled in relation to its distance to the related city. In this way edge hexagons are pulled farther (given that the physics engine may model one or more aspects of gravity and so the hexagons may be affected by distance as well as mass) than the interior hexagons causing a scattering toward the related cities. In one embodiment the city (i.e. the location of the city) is given a "gravity" force to instigate further distortion. In one embodiment, the initial location of the patient storm is given a "gravity" force to instigate further distortion. Distortion determines a skeleton of the overall shape of the patient storm cell (or combined cells) into which color elements are placed to create the patient storm cell visualization.

In one embodiment an area of the map (or the entire map) is used to determine the placement of color in association with a patient storm cell using probability of placement. In this model each location can receive a pixel, hexagon, colored shape or icon to name a few and each location is assigned a probability based on a number of factors including the distance from the associated city, pathways of influence based on related cities, variability of the severity profile to name a few. Once probabilities are assigned then individual visual elements (e.g. pixels) generated by the associated severity profile are scattered into the probabilistic matrix to determine their location.

In the present embodiment, a proximity threshold between patient storm cells can be breeched to instigate a patient storm cell merge. In an alternative embodiment, the triggering of a merge may be based solely on a comparison of the severity profiles of related cities rather than proximity on the map or may be based on at least a combination of severity and proximity. Several different forms of merge can occur. The complete merge can be triggered in which the profiles of the merging patient storm cells are simply added together to create a single patient storm cell. Alternatively, patient storm cell merging allows the centers of the patient storms (e.g. the high-severity areas) to remain distinct while the rings of lower severity merge into a single element. These rings around multiple patient storm centers then form a shape similar to merged circles. In one embodiment the outside rings maintain the shape of a single patient storm cell while only the interior area displays multiple centers creating a multi-centered patient storm cell. Any number of patient storm centers may be included into a single patient storm system.

In one embodiment, the move, residual, distortion and merging are done in a way to restrict any of the patient storm cell visualizations to be on top of cities for which there are no severities found.

In one embodiment, the shape skeleton created by residual, distortion and merging become the basis for the general outline of the patient storm cell and additional transforms are applied to remove certain elements of geometric precision and symmetry such that a more weather-like appearance is generate while maintaining the overall shape and proportion of severity.

In the present embodiment, a finish stage is executed to smooth, texture, visually enhance to name a few.

Figure 11:
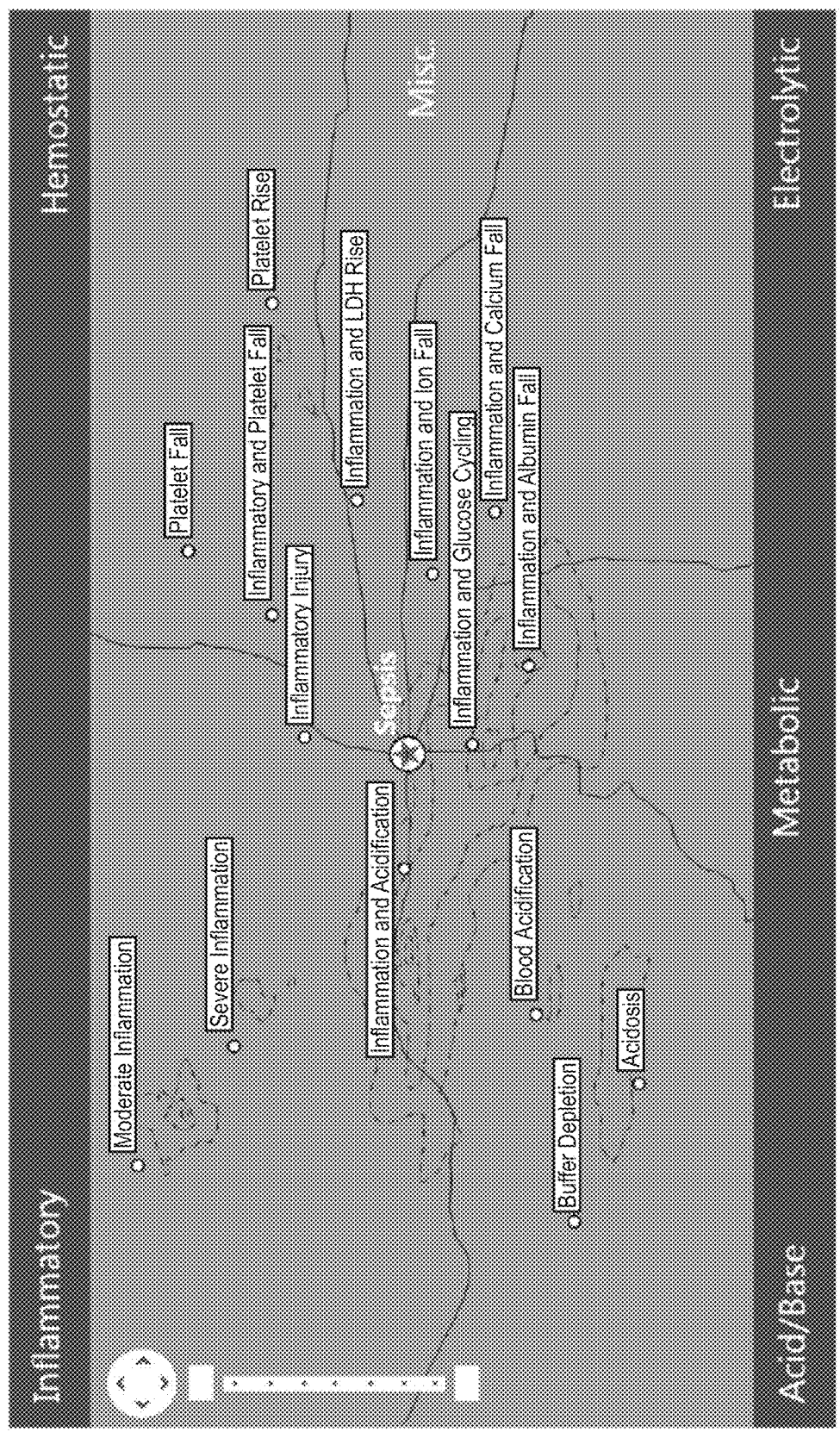
FIG. 11 is a wireframe display of the weather layer on the condition-centric patient storm tracking map for sepsis.

In one embodiment, the stages of transformation are shown to a user or for the purpose of facilitating map creating and/or modification. FIG. 11 depicts a wireframe display used to show the stage after move, distort and merge but before the colorization and finishing process has been completed. Cycling through the stages of transformation provides an informative visualization of the way the data is translated from raw input into the weather display. Further, healthcare workers can use the various stages to review the data. For example, reviewing the data without the application of the physics engine would allow the user to see the exact profiles associated with each sub-condition on the map without respect to relationships to other sub-conditions or merging generated by proximity. Monitors could be set to show a particular stage of the transformation or a trellis display showing multiple stages simultaneously can be employed allowing the full impact of the weather metaphor to be employed alongside less transformed visualizations.

The PSTVP applies the above techniques for all cities on the condition-centric map to generate the weather layer of the visualization. In the present embodiment the weather layer only uses data for a specified time window.

In one embodiment shapes (such as hexagons, squares, rectangles, to name a few) which completely cover the background of the map make up the weather layer. In this embodiment, one or more severity modes are associated with a single cell on the map and determine the color of that cell. In this embodiment, no movement, distortion, merging or finishing is done, but the patient storm visualization emerges from cells becoming active and changing in color over time. The cells may be positioned in relation to each other so that specific conditions such as sepsis will appear similar to weather. In particular cells responsive to single perturbations and milder perturbations may be positioned to the left and or above cells responsive to relational perturbations or more sever perturbations so that the patient storm expands and/or moves to the right or downward as the sepsis progresses even though the actual cells may not move.

In one embodiment the display is comprised of density cells which are graphical encapsulations of a perturbation. Each density cell contains mathematical or other information related to the density perturbation it embodies. A density cell may reside in predetermined locations in each clinical region of the geographic space. Density cells are also designated (and positioned on the graphical space) by the biologic compartment in which they reside, and the particle itself. Density cells may also be designated and positioned on the graphical space by their polarity since perturbations of different polarity of the same density particle generally occurs by different forces and therefore often represent completely different biologic events.

An example of a positive density cell may be a square comprised of 10 or more density cell compartments called "density organelles" or simply "organelles." Each organelle contains a single mathematical or other density value related to the perturbation which defines the cell. The density value can include for example an; absolute magnitude, absolute value, duration, slope, area under the curve (or over the curve in the event of negative polarity), acceleration, the product of the absolute magnitude and the square of the slope, the personal threshold specified relative to the personal range, the population threshold relative to the population range, a testing trigger threshold, a treatment trigger threshold, a preferred threshold and/or other value.

A mathematical number for each of the above values may be provided in each organelle wherein the value is known or can be calculated. This produces a matrix of mathematical values which relate to the perturbations of densities over specific time intervals. The values can be designated with colors which relate to the severity of the perturbation so that the organelles have both a color and a mathematical value. Although density cells are a common cell type, other cell types, which, for example, relate to particle size or other features, may be provided.

Density cells may contain mathematical information related to a density perturbation of a single particle or they may be "relational density cells" which relate to a relational perturbation of a plurality of particles. Additional organelles may be added to accommodate the many potential values related to organelles defining. Each time a new data point is added to the time series matrix at least one new density cell is generated and positioned on the display in the specified location for that cell. As with the earlier discussed weather maps, time may be shown along an x axis (or other axis) with the cells being in fixed positions along the Y axis but moving with time to the left as new cells are generated at that site. Alternatively, each cell is replaced as time proceeds (with the cells fixed in place in 2 dimensional space). A 3 dimensional representation with fixed cells and time along the third axis may be shown which can then be sectioned perpendicular to the time axis to view the pattern at any specific time or parallel to the time axis to view density relationships over a time period. The image may be provided in transparency so the user can look into the image, for example in a perspective view, and see the relationships of the past or future (which may be projected) perturbations inside, beyond the time defining the surface of the image. In this way a 3 dimensional (for example) rectangular matrix of mathematical values and severity colors is generated which comprises the global mathematical image and colored image of the densities and perturbations of an individual over time. Portions of these images may be converted to more typical weather radar looking images when clinical failures are identified.

The top layer for the condition-centric map is the overlay layer. The overlay layer provides iconic annotation and an indication of relevant events, trends or other elements to be highlighted. As an example, the overlay layer will display patterns of perturbation 320 and recovery 310, rapid increases or decreases in severity, condition identification, areas of missing data, areas of data coming in with an entry delay outside of prescribed protocol, treatment/intervention events, expected recovery indicators, patient storm path, and or patient storm trajectory indicators to name a few.

In the present embodiment, the overlay layer uses icons that tap into the weather metaphor. For example, as shown in FIG. 3, trends in perturbation 320 and recovery 310 are displayed in a similar way that high and low pressure fronts are displayed on a weather map. An iconic representation within the clinical space—P for perturbation, R for recovery is displayed. Further bands 330 are shown to provide the direction and size and relative location of the trend. For example, as shown in FIG. 3 the Hemostatic space is recovering or has recently recovered and therefore displays an R 310 and an iconic band 330 showing the space moving away from perturbation. On the other hand, the Acid/Base space is displaying a great increase in the amount and severity of perturbation and therefore is shown with a P 320 and a large band 350 close in to the center and with arrows showing a continued trend toward additional perturbation. In this way the overall state and trend of the clinical spaces can be rapidly assimilated. In one embodiment, lightning icons are used to delineate rapid increases in severity. In one embodiment, grey shapes are used to indicate missing data. In one embodiment, arrows are used to indicate patient storm direction. In one embodiment, a band of color is used to indicate a probabilistically derived patient storm path. In one embodiment, lines are used to connect treatment events with related (or possibly related) severity elements. In one embodiment, the background of a clinical space is colored to indicate perturbation or other states and/or trends.

In one embodiment, several overlay layers are possible with a specific focus and can be toggled on and off independently. For example, one overlay layer may be specific to the relationship between treatment and perturbation while another layer may be specific to highlighting missing, sparse or delayed data and another layer may be specific to perturbation and/or recovery forces. These layers could be turned on or off and could be used in conjunction depending on the needs and focus of the user.

In the present embodiment, time is used to animate the condition-centric weather map to produce a moving picture of systemic weather over the universe of clinical spaces, sub-conditions and the target condition. The PSTVP receives a set of severity profiles for a given point in time to produce visualizations on the weather layer and analyzes the current set along with the past sets to generate the overlays on the overlay layer. As the data changes in time those changes are reflected within the weather and overlay layers. Moving through time in succession provides an animation showing the evolution of perturbation. Time can be shown forwards and backwards at various speeds. A time loop is provided to show recent evolution or evolution within a specified area of time.

In the present embodiment, the PSTVP provides several different types of interaction with the condition-centric weather map. Gestures with a mouse or a touch environment or a natural interface can be employed to navigate, drill down, zoom and scroll to name a few. In the present embodiment, the user may annotate visually or with audio-visual notes.

In one embodiment the condition-centric weather map may be manipulated by the healthcare worker and/or researcher to consider hypothetical scenarios or scenarios based on the rejection of certain test results or events which may be considered in error, anomalous or otherwise inaccurate. Alternate visualizations (along with their updated, added or annotated data) may be stored in whole and may be compared against the working set to understand the results of the altered data.

The PSTVP presents maps, such as the map in FIG. 1, both individually and in combination in a trellis display. For example, a single patient can be shown with a 4×4 trellis display of sixteen maps each displaying the state with regard to a different condition such as sepsis, congestive heart failure, hepatic failure, renal failure, drug or transfusion reaction to name a few. This display is typically sorted with the most severe first providing a rapid review of the state of the patient with reference to the conditions monitored.

Alternatively, the PSTVP presents a set of patients for a single condition (e.g. Sepsis) in a trellis display. Sorts are provided to highlight patients with the greatest severity and or correlativity towards the selected condition. Filters can be provided by weather elements including minimum severity within clinical spaces, patient storm types, initiating clinical space, dominant clinical space, overall perturbation coverage (i.e. global perturbation volume), perturbation and/or recovery trends, recent changes, recent events associated with changes, incomplete force binaries to name a few.

In one embodiment, the condition-centric weather map is presented alongside other visualizations including time-series display, lab records, physician notes, ROC charts, patient event logs to name a few. Further, interaction with the weather map can be used to highlight, select, sort, filter or otherwise manipulate related visualizations. For example, the selection of a weather cell within a map can select all of the points within a time series display which contributed severity into the selected patient storm cell and can induce a display of the time series, tabular or sequential values, and or time series relationships to provide computational transparency. Alternatively, selections of points within a time series display can zoom, scroll and/or highlight the weather map as well as move the weather map, or a set of weather maps, to a specific time.

A health worker may want to see the evolution of a patient condition within the clinical spaces in a glance along with a detailed visualization of the state at a particular point in time. In one embodiment, the condition-centric weather map is placed alongside a historical weather map in which time the element on the x-axis as described in U.S. patent application Ser. No. 13/677,295 filed Nov. 14, 2012. Animation within the condition-centric weather map can be associated with a single vertical line within the historical weather map and arrows, highlights, iconic elements or other visual cues can be used to tie these two together such that the evolution in time is presented within the historical weather map and an animation of the state over time is presented in the condition-centric weather map.

Figure 6:
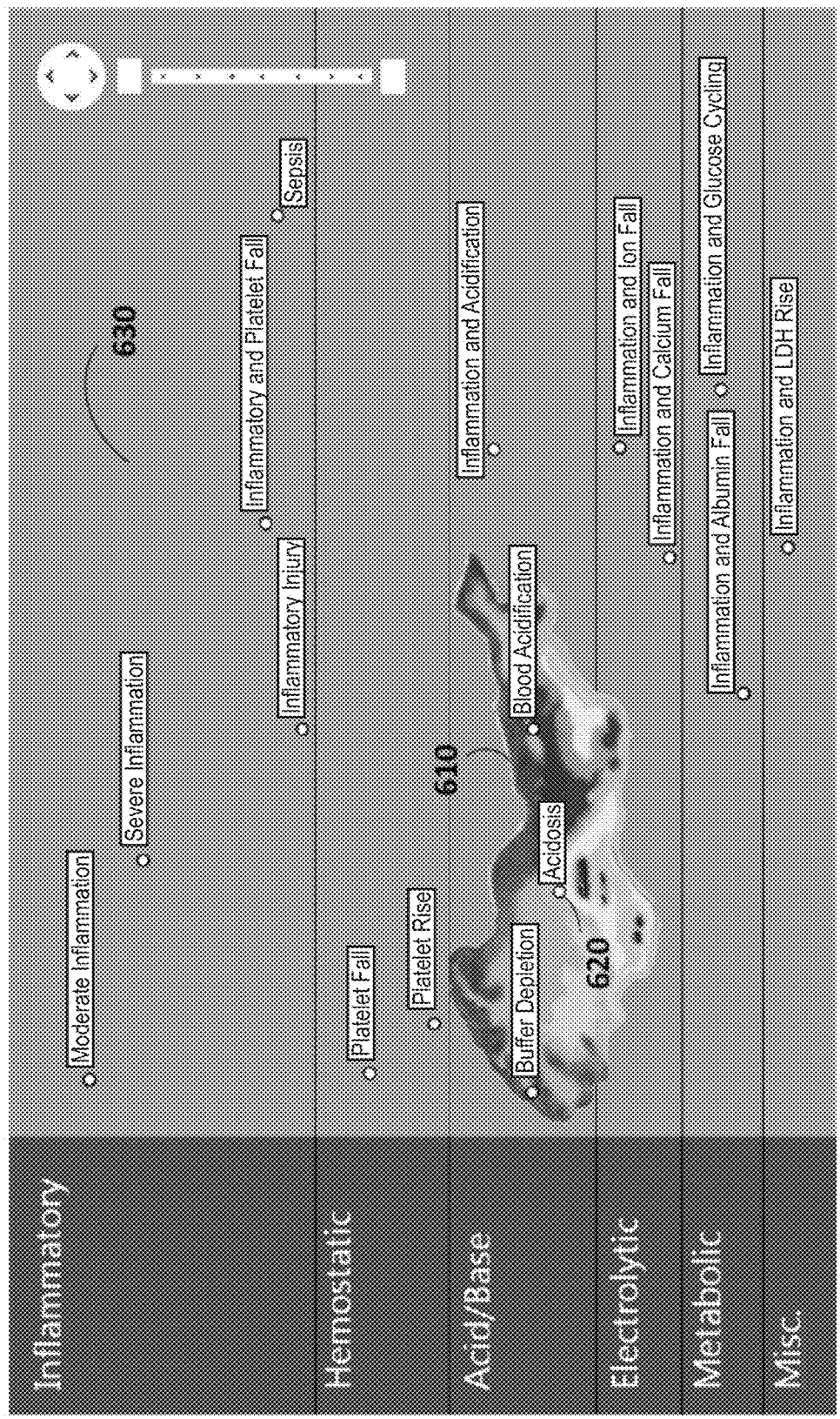
FIG. 6 depicts a patient storm tracking map in which weather moves from left-to-right within vertically stacked areas of clinical space—in this case showing a patient exhibiting the symptoms of hemodynamic shock.
Figure 7:
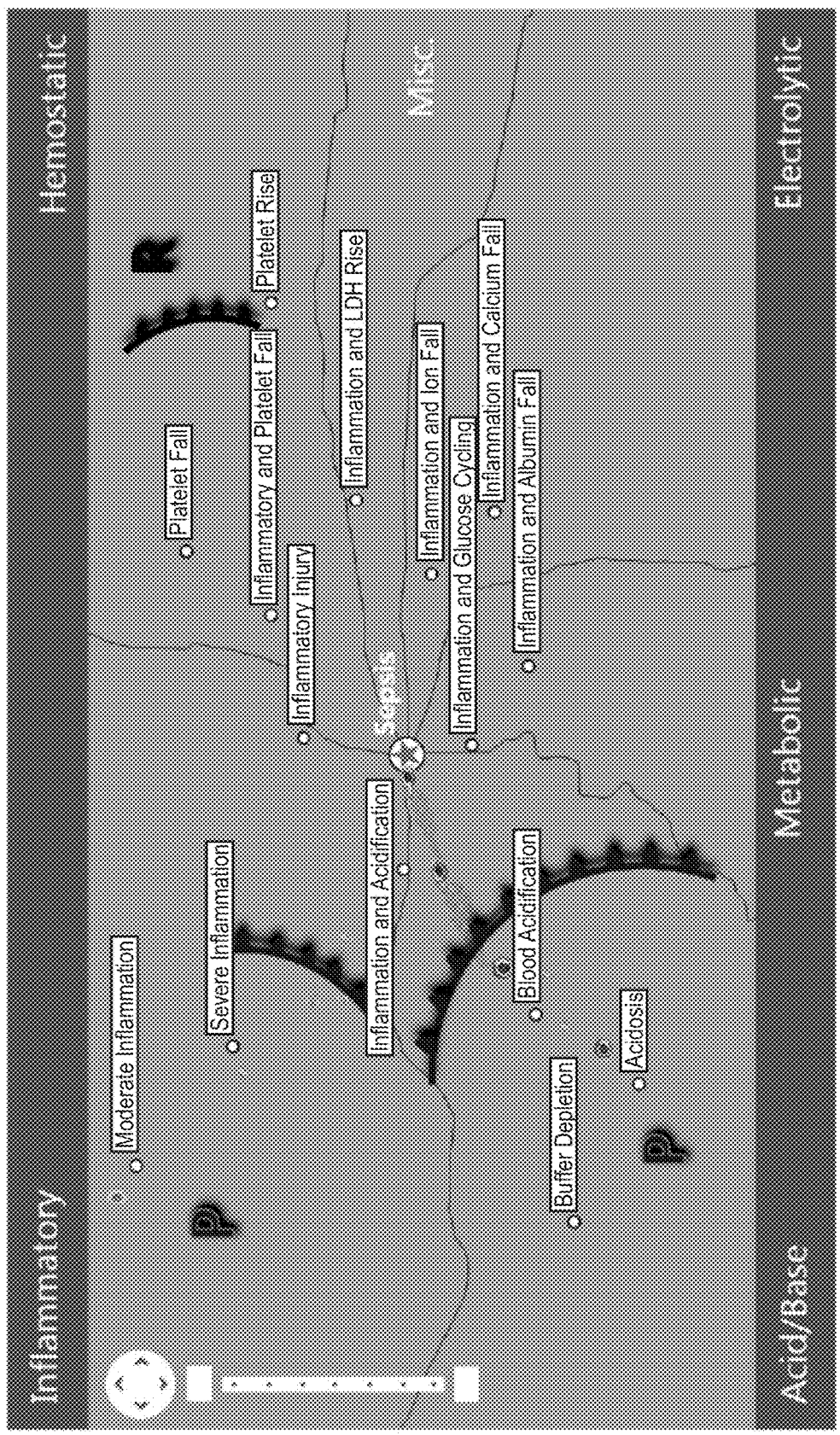
FIG. 7 depicts a condition-centric patient storm tracking map for sepsis using a hexagon-based weather layer.

In one embodiment in place of or in conjunction with the condition-centric patient storm tracker visualization the visualization in FIG. 6 is shown. In this patient storm tracker map clinical spaces span from left to right and are stacked within the visualization. Cities are placed in a similar fashion as described above and may be always visible or may appear if the patient storm warrants their appearance (as by generation the storm cells which relate to the city). In this visualization, patient storm patterns 610 may grow or move from left-to-right as, for example, severity, correlativity to a condition and/or relational complexity. FIG. 6 depicts a patient exhibiting a pattern and/or symptoms of new onset acidosis 620 which can indicate occult or overt hemodynamic insufficiency. The lack of active moderate or severe patient storm cells in the regions of inflammation 630 suggests that it is not likely that this is a sepsis patient storm.

Figure 12:
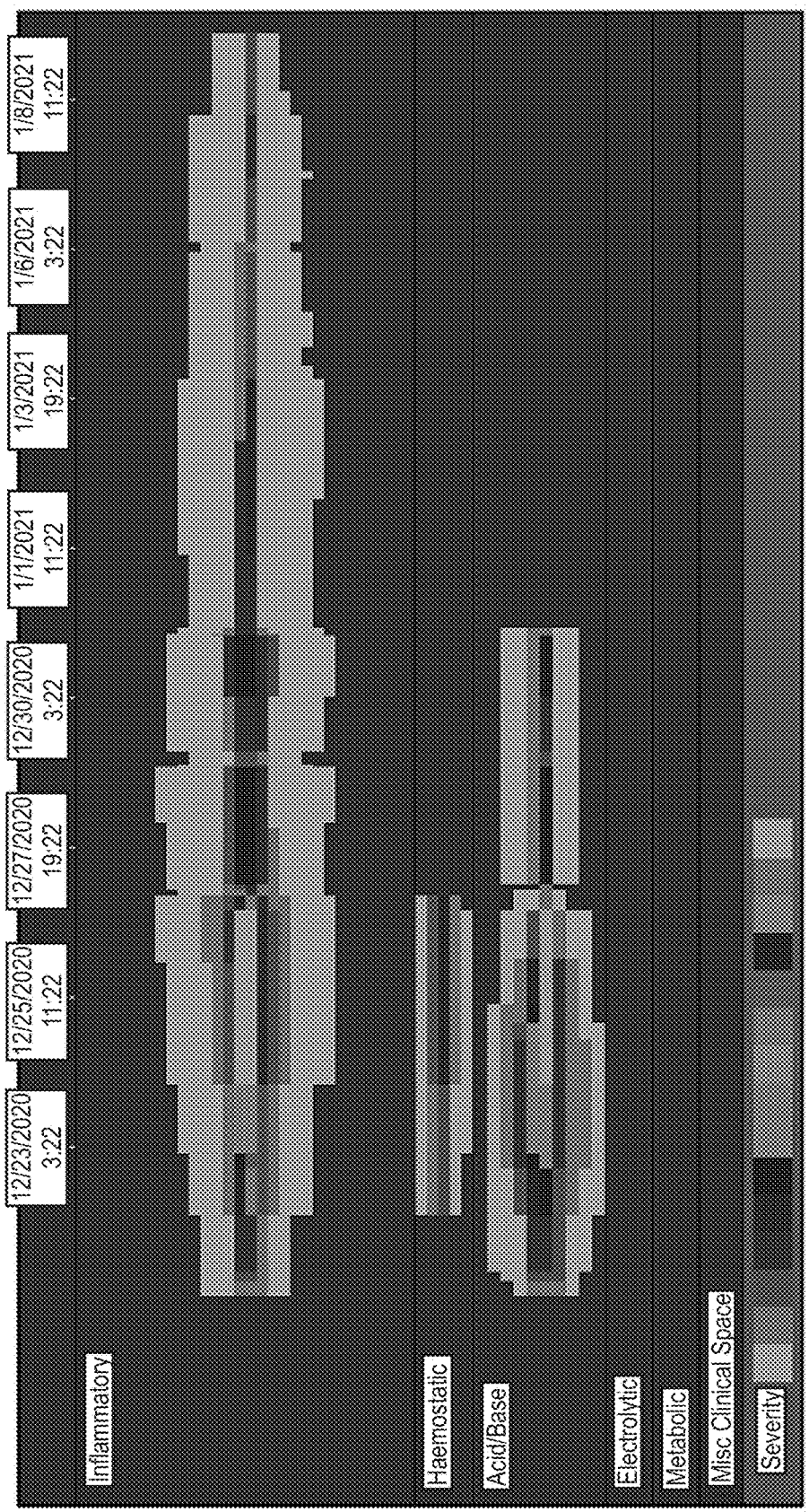
FIG. 12 depicts a historical patient storm tracking map for sepsis for a patient diagnosed with sepsis.
Figure 13:
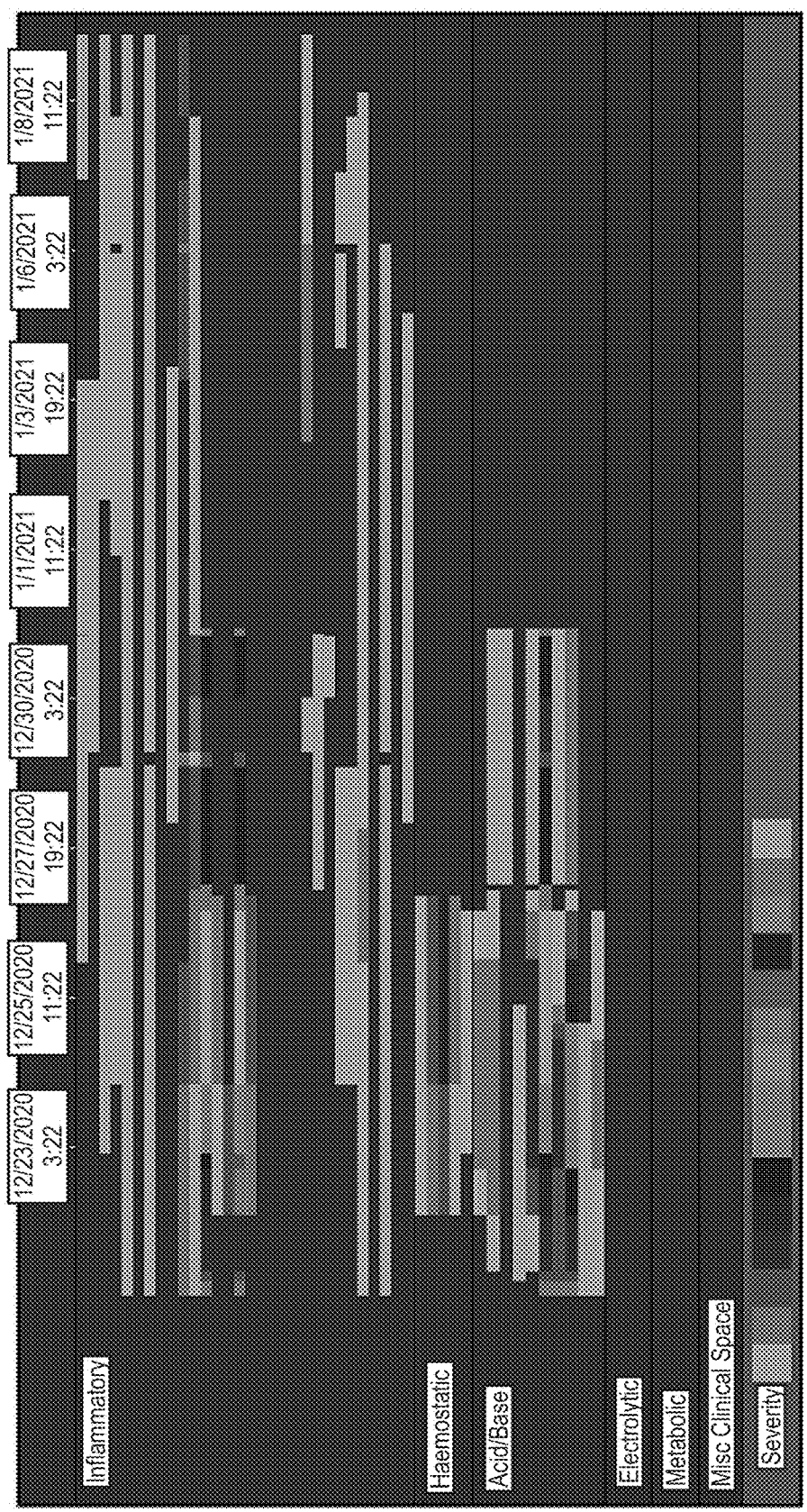
FIG. 13 depicts a historical patient storm tracking strip map for sepsis for a patient diagnosed with sepsis.
Figure 14:
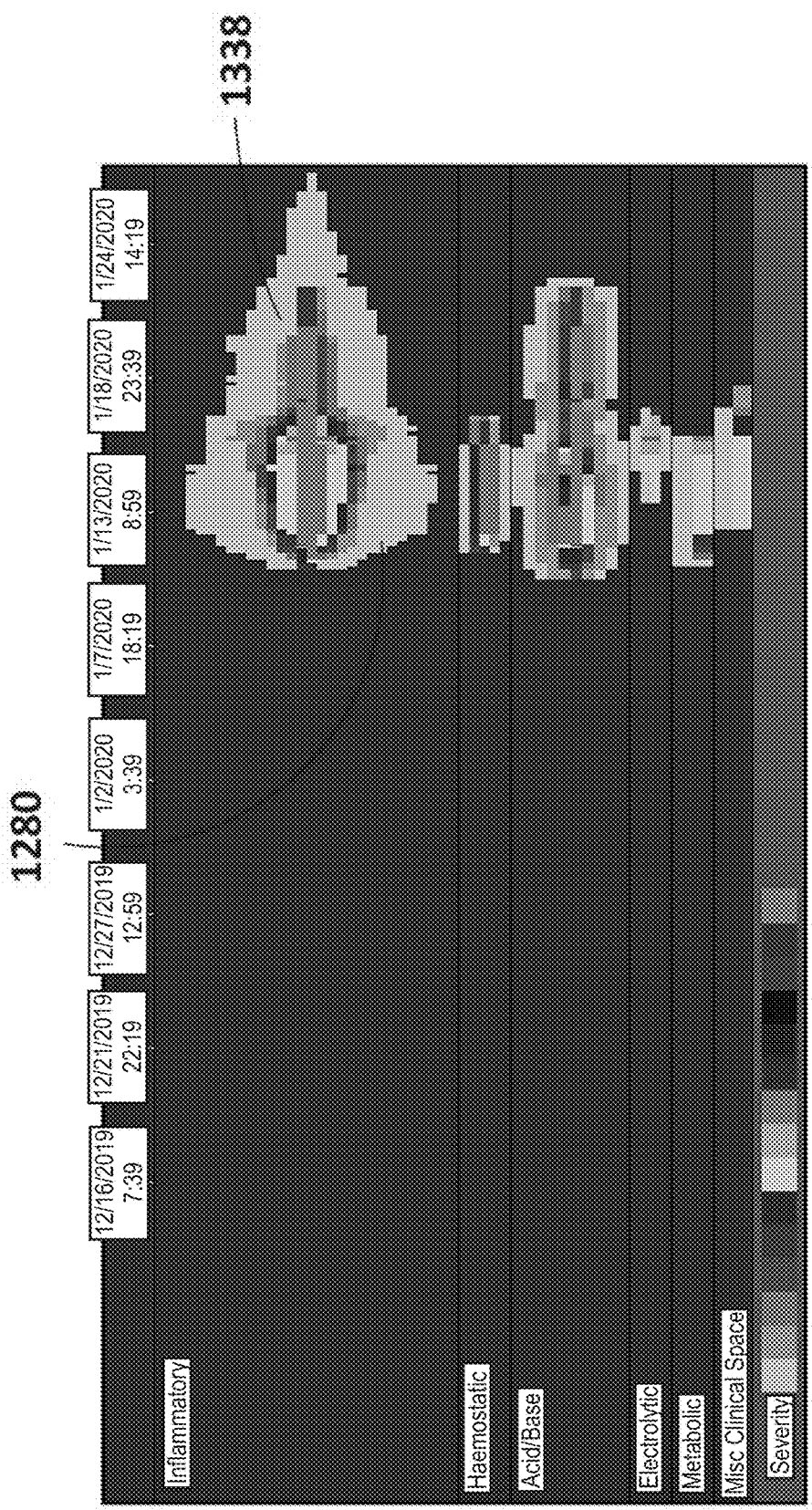
FIG. 14 depicts a historical patient storm tracking map for sepsis for a sepsis patient with rapid acceleration followed by recovery.
Figure 15:
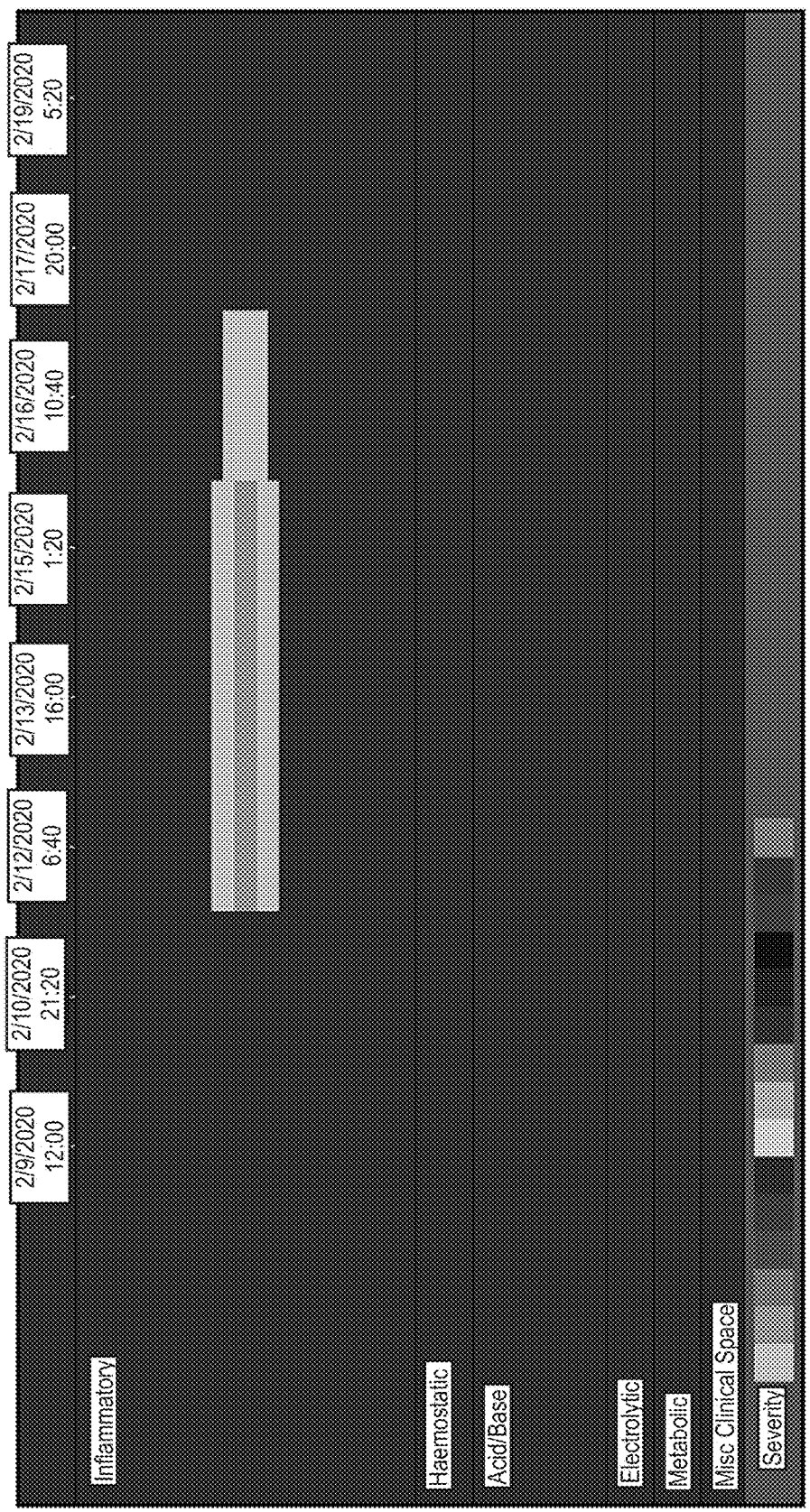
FIG. 15 depicts a historical patient storm tracking map for sepsis for a patient which exhibits CHF.
Figure 16:
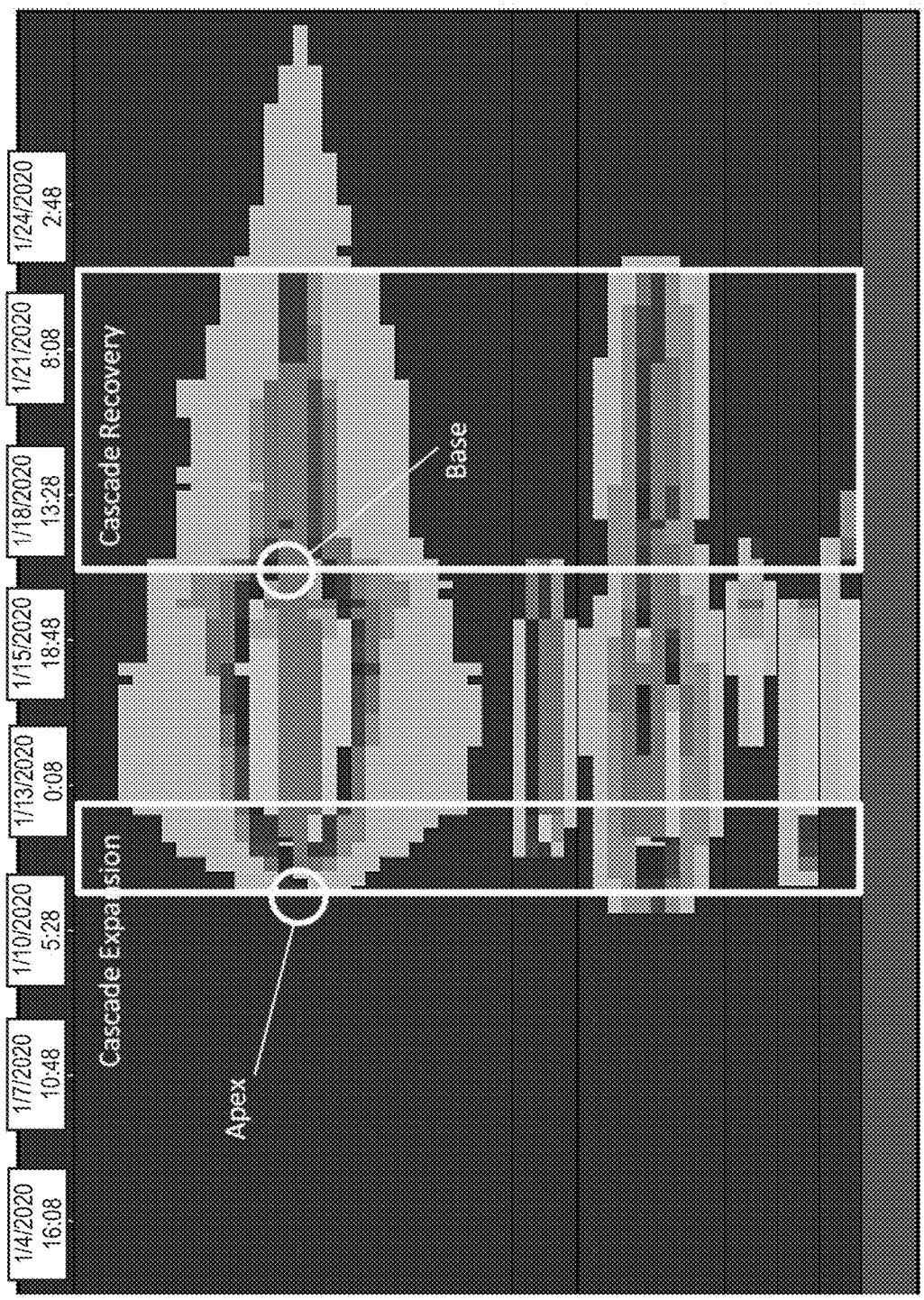
FIG. 16 depicts a historical patient storm tracking map for sepsis with overlays highlighting cascade expansion and recovery and other patient storm elements.

In one embodiment in place of or in conjunction with the condition-centric patient storm tracker visualization the visualization in FIG. 12 is shown. FIG. 12 depicts a historical patient storm tracker map. In this visualization, time is shown on the x-axis and in this way the evolution of a condition can be accessed at a glance. The historical patient storm tracker map is described in the aforementioned patient applications. FIG. 14 depicts the severity-centric version of this map with a patient which displays a rapid expansion of perturbation 1280 followed by a period of recovery 1338. FIG. 16 shows how overlays within this map can be used on top of the historical patient storm tracker map. The historical patient storm tracker map can be used as a navigation mechanism for the condition-centric patient storm tracker and other time-animated maps for example providing a histogram-style navigation slider.

Figure 17:
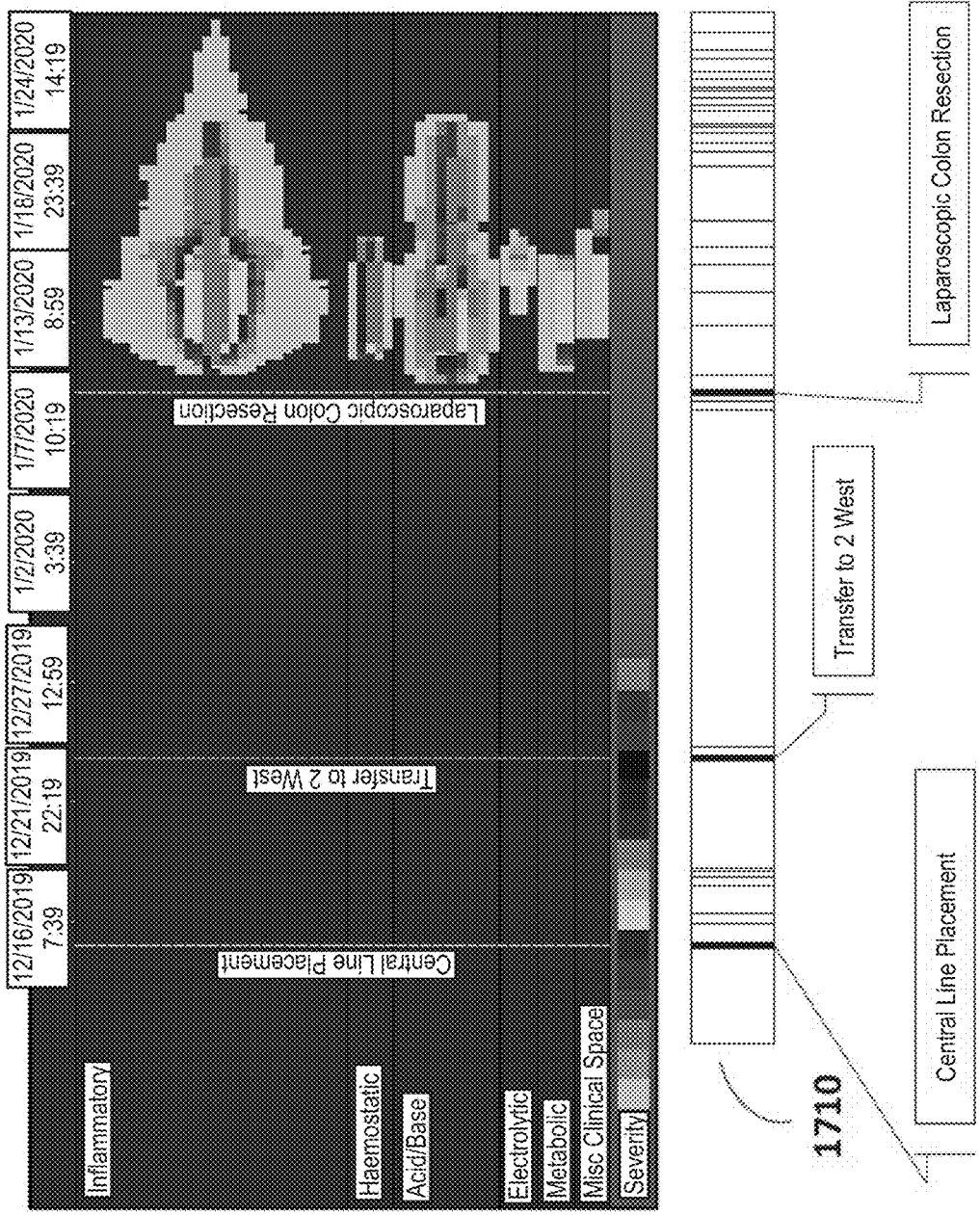
FIG. 17 depicts historical patient storm tracking map for sepsis with an associated event line to allow for visualization and interaction of a patient storm in the context of the event stream.

FIG. 17 depicts one embodiment in which an event bar 1710 accompanies the historical patient storm tracker. These both can provide a useful navigation tool for the condition-centric patient storm tracker and other time-animated maps. In this way the location of patient events—surgery, drug therapy, diagnosis to name a few—can be analyzed in the context of perturbation within clinical space in time (as per the historical patient storm tracker) as well as an animated point-in-time display of the condition-centric and/or related maps. Gestures within each visualization—the condition-centric map, the historical map and the event bar 1710 can be captured to indicate user intent with regard to zoom, time-navigation, filtering, drill-down, sorting to name a few.

Figure 18:
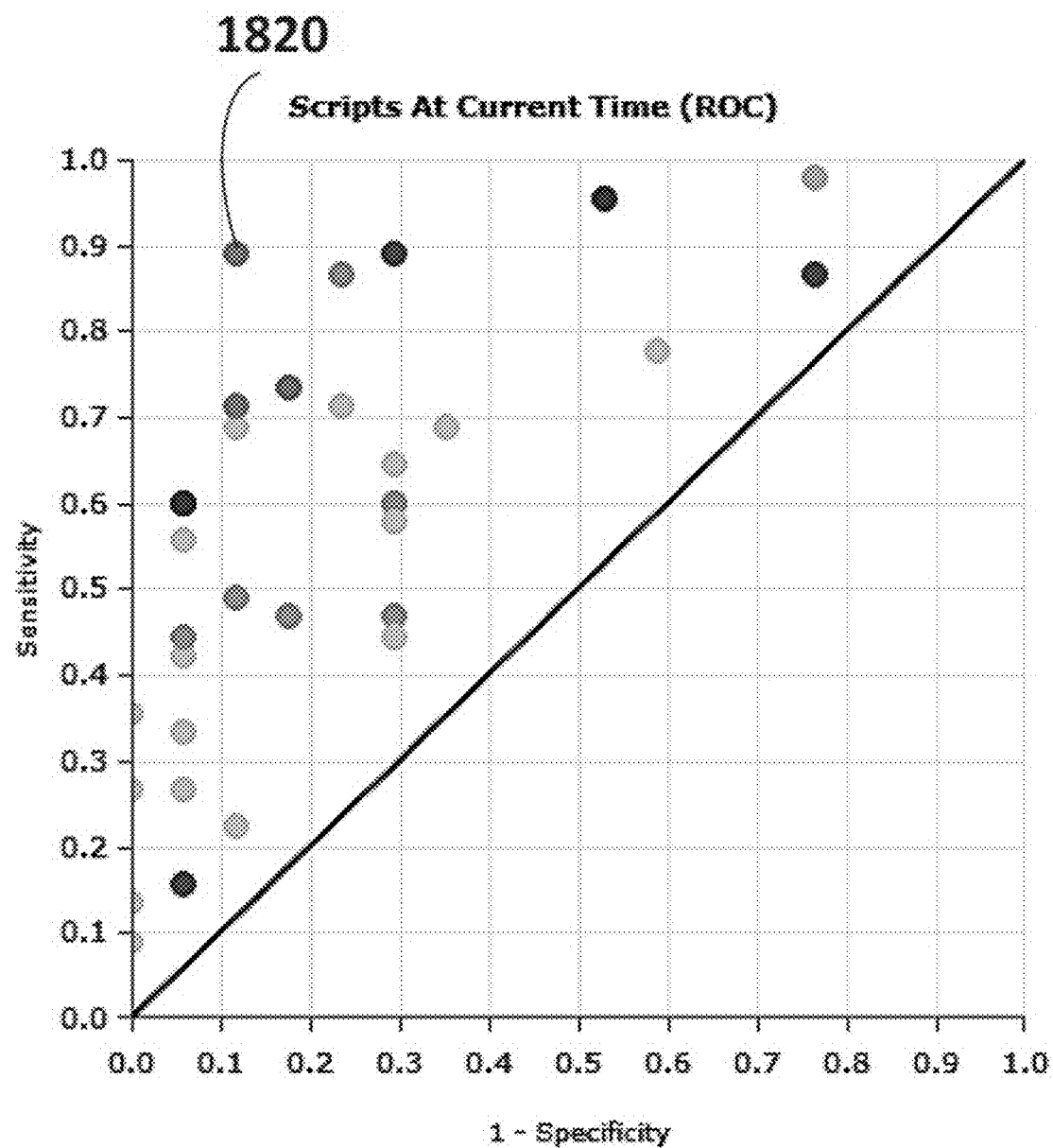
FIG. 18 depicts an ROC pattern map for a specific point in time used in association with a patient storm tracking visualization.

In one embodiment in place of or in conjunction with the condition-centric patient storm tracker visualization the visualization in FIG. 18 is shown. FIG. 18 shows an ROC pattern chart depicting the currently identified patterns in ROC space for a given point in time or time span. The ROC pattern chart provides rapid access to sensitivity/specificity towards a condition (e.g. sepsis) in substantially all patterns being monitored. Each pattern for which occurrences are identified will be displayed in the location 1820 which indicates sensitivity and specificity derived from a training set of retrospective patients or supplied by a third party or derived from real-time patients to name a few. In one embodiment, as shown in FIG. 18, the pattern dots 1820 are colored using the maximum severity within the severity profile for the given pattern. In one embodiment relationships are depicted using arrows. In one embodiment, the selection of individual or sets of patterns are used to affect other visualizations such as filter, sort and/or highlight to name a few.

In one embodiment potential future trajectories and paths of the patient storm are projected on the visualizer. One method for projecting a path may be to project the slope of the expansion of the cascade image and project that slope outwardly. Another method of projecting the trajectory comprises identifying the pattern (such as a sepsis pattern) and then projecting the values of a plurality of parameters which comprise the pattern to points at future time intervals which are consistent with progression of the condition over the time intervals. For example the slope of the platelet fall, the bicarbonate fall, and/or the band rise may be determined then each projected forward (for example the slopes may be projected for 2-24 hours or more) and the relational patterns of these values may be determined to predict a potential trajectory (which may for example be a "worse case" trajectory) sub conditions. In an alternative, slopes (which may be "worst or near worst case" slopes) which occur in certain conditions (such as sepsis) known by experience, determined by review for retrospective data sets or in prospective trials may be used to enhance the accuracy of the projections. For example, through experience with many advanced sepsis cases one of the present inventors has noted that until the septic state is controlled, the bicarbonate may fall with a slope of about 1 meq/hour. This will induce an attendant increase in respiratory drive which can be projected as it will be rise as a direct function of the fall in bicarbonate. Heart rate can also be expected to rise in response to the rise in respiratory rate and fall in bicarbonate. It is not necessary to precisely predict these values and the relational sub-conditions but rather to simply project a path which is consistent with one possible path if the pattern progresses without intervention. From the perspective of the visualizer the bicarbonate may exert a gravitational effect on the respiratory rate and heart rate increasing the severity of any specific value of these parameters. The projected path (which can be defined by the processor, and then presented to the healthcare worker for example by query or automatically) provides a warning to healthcare workers that time is of the essence and rapid intervention or at least frequent follow-up is required to determine if the patient will follow such a path.

Alternatively, a trellis display of possible "futures" may be presented to the healthcare worker each with an indication of the conditions that would cause the proposed future.

In one embodiment probabilities are attached to the futures and/or path displays.

One approach for projecting a path and for determine a patient specific frequency of automatically ordered lab testing is to calculate a potential worst case path or value of a parameter and then identify the retesting time based on the minimum change of the parameter which would have clinical relevance given the potential condition or conditions identified by the processor. For example, if the processor has identified severe sepsis as a potential condition, then a projected bicarbonate (or other lab values) can be calculated by Equation 1:

$$V_p = V_s + T_D(dV/t) + T_i(dV/t) \qquad \text{Eq(1)}$$

Where:
$V_p$ is the projected value of the parameter at the projected time;
$T_i$ is the time interval between the last sampling time and the projected time;
$T_D$ is the delay between the sampling time and the display time;
$V_s$ is the value of the parameter at the sampling time (this may not be known until later if there is a transport and/or testing delay); and
$_dV/t$ is the worst case or near worst case slope of the parameter given the condition(s) identified as potentially present by the processor (such as sepsis).

An efficient timing of retesting which would enhances the ability to early detect significant change may be made by setting the next sampling time to an interval calculated from specifying the minimum or maximum (depending on the polarity of the trajectory) of the projected value which would (if known) affect diagnostic or therapeutic action given the condition(s) identified as potentially present by the processor. For example, suppose the bicarbonate value at the sampling time (Vs) was 20 and is identified by the processor as falling at a rate of 0.5 meq/hour and the processor further identified the image as representing a high probability that sepsis is present, yet the processor identifies the next test for bicarbonate has been ordered by the physician at 8 hours and the average, worst 10 percentile (or other measure), of delay from sampling time to display time (TD) is known or calculated to be 1 hour for this particular hospital ward. Then in one embodiment, the processor can be programmed to identify an improved sampling interval based on a projected "worst case" bicarbonate fall of 1 meq/hour for the condition of sepsis, and adjust the repeat bicarbonate testing to 2 hours since a fall in bicarbonate to 17 (the value which could reasonably be present in 3 hours (sampling interval plus delay interval) would (if known) affect diagnostic or therapeutic action given the condition(s) identified as potentially present by the processor (in this case sepsis). In the alternative, when managing this patient without the processor intervention of the present embodiment the bicarbonate could have fallen to 11 (before outputted as 12 on the display) and this value in this range can result in death (perhaps before the sample is even taken). As demonstrated in this example, the condition or pattern specific projection of individual parameter values provides both warning and a means to improve sampling time and therefore the diagnostic utility of the motion image and improved protocolization of treatment. Furthermore the projection of multiple parameters can be used to render one or more possible paths which the patient storm may take if, for example, intervention in not provided.

In an embodiment, a display is provided indicative of a time matrix comprised of solved perturbation image binaries, recovery image binaries, perturbation force binaries, and recovery force binaries, as well as unsolved binaries as described in co-filed application U.S. Provisional Patent Application Ser. No. 61/770,971, filed Feb. 28, 2013, entitled "Programmatic Human Matrix" (the entire contents of which is incorporated by reference herein for all purposes). Binaries and/or the graphical representations derived from them (such as weather map type images) may have a different colors, or other markings to differentiate different binaries and between solved and unsolved binaries or the storm cells associated with different binaries.

In one embodiment, the healthcare worker may choose to visualize a patient's weather map as derived from solved and/or unsolved perturbation image binaries, recovery image binaries, perturbation force binaries, and/or recovery force. Drill downs requesting the binary information relating to the patient storm cells may reveal the spatial and temporal pattern relationships of both density modifying forces and density changes. Drill downs requesting the image binary information relating to the patient storm cells may reveal the spatial and temporal pattern relationships of events, patterns and cascades comprising the image of a patient's condition and care.

Other weather metaphors which may be generated to visualize sepsis or other conditions include, for example tornadoes and hurricanes. Other non-weather metaphors include forest fires, floods, battles/battlefields, ocean currents, population growth or movement, traffic movement, to name a few.

In one embodiment, used independently or in concert with the condition-centric weather map, a 3-dimensional globe is portrayed within the visualization indicating sections which are displayed by individual condition-centric maps. In this way, an array of conditions is monitored and portrayed in three dimensions as sections on the surface of a "globe". The health-care worker can interact with the 3-dimensional patient globe such that it can be spun, "pushed back", "brought forward" to name a few associated with gestures indicated through a mouse, touch surface, natural interface to name a few. In one embodiment, sections on the globe represent individual conditional-centric maps. The user may then spin the globe seeing, at a glance, storms represented for each condition being monitored on the surface of the globe. In one embodiment, the location of the sections on the globe is fixed to represent a global geography such that a user can remember the location of individual maps. The user may then select one or more sections to show side-by-side with the patient condition globe. The side-by-side display may be a single map or a trellis display with selected maps indicated by color, letter, number or some other symbolic and/or iconic mnemonic to associate with a highlighted section on the patient globe. In one embodiment the trellis associated with the patient globe is automatically (or be default) filled with the most severe storms identified for the conditions monitored. The individual storm maps are sorted by maximum severity, perturbation volume or other storm classification.

In one embodiment, used independently or in concert with the condition-centric weather map, a 3-dimensional translucent globe is portrayed. In this way, an array of conditions is monitored and portrayed in three dimensions as planes that pass through the center of the transparent or translucent globe. Each clinical system is a circular plane passing through the center globe. In this way, all clinical systems intersect in the center so that relational patterns between systems may expand across the center into any other system. Storm cells may be 3-dimensional objects which have height, width and depth. The health-care worker can interact with the 3-dimensional translucent patient globe such that it can be spun, "pushed back", "brought forward" as well as entered into in 3-dimensional space to name a few associated with gestures indicated through a mouse, touch surface, natural interface to name a few. The severity of the affected densities and parameters in a system may determine its shape, size and position in the circle relating to that system with more severe perturbation being more centrally located and very severe being at the center itself. Since very severe perturbations generally affect multiple densities from multiple systems severe cascading conditions such as sepsis will demonstrate a large central mass of color storm cells with severe colors such as purple or red, in the center and the milder colors such as green in the outer portions of the mass. In one example, the time lapsed animation the storm cells move and/or expand, grow, and emerge centripetally with early outer green and then later centrally located purple and red inside a 3D storm mass at the center of the sphere. The planes may be rotated to show the intersection and the storm expanding across the center (at times in both directions) into other adjoining plane. In one embodiment the planes within the translucent globe interact with each other. In one embodiment the interaction is through a global physics engine that pulls storm cells in 3 dimensions both from related storm cells within the same plane and by related storm cells on other planes within the translucent globe. In one embodiment, the 3-dimensional location of the planes within the globe is fixed to represent a global topography such that a user can remember the location of individual maps. In one embodiment the user can select individual planes within the globe to see them side-by-side with the translucent globe. In this way a 3-dimensional weather-map is shown in which storm cells are not simply represented as 2-dimensional but as 3-dimensional shapes projected using rendering that provides the visualization of 3-dimensional objects on a 2-dimensional display system. The user may select one or more planes to show side-by-side with the globe. The side-by-side display may be a single plane or a trellis display with selected planes indicated by color, letter, number or some other symbolic and/or iconic mnemonic to associate with a highlighted plane within the patient globe. In one embodiment the trellis associated with the translucent patient globe is automatically (or be default) filled with the most severe storms identified for the conditions monitored. The individual storm planes are sorted by maximum severity, perturbation volume or other storm classification.

In one embodiment, used independently or in concert with the condition-centric weather map, the map is made up of a circular line along with cities, as described above, are placed. The background is, therefore, a fixed circle with cities arranged along the line. The weather layer is then layered on top of this set of cities with perturbation, as described above, shown as expanding color, shapes of color (e.g. hexagons), sets of icons to name a few. In one embodiment movement of storm cells associated with a city toward the center of the map is proportional to perturbation volume increases. In one embodiment the movement and/or expansion is proportional to the sum of the perturbation volume between related cities and the direction of the expansion is determined by a vector drawn between the cities to each other across the map.

In one embodiment the map is circular which regions radiating from the center or a center circle or other shape. A region for mild storm cells and or single events indicators is positioned around the perimeter. As the condition becomes more sever the regions move closer to center generate color indications, as severity worsens further this enters these color indications reach the center and may extend into the regions which are relationally affected.

One embodiment comprises a patient monitoring system having at least one processor programmed to generate an image which displays a patient condition as color weather radar on a map. The map can be a 3D map or 2D map with or without a time axis. The map may be rectangular, circular, or spherical. The map may be divided into sections that represent clinically differentiated subsystems. The sections may intersect and the sections and/or the intersections may be movable or fixed. The position of the sections in relation to each other may be responsive to the pattern detected by the processor or other factors such as recent procedures or medication. The map may have different configurations, different cities, and or different spatial relationships of the sections responsive to the dynamic clinical pattern or image detected by the processor.

The positions of the sections and/or cites may be dynamic responsive to the pattern or image detected by the processor so that for example sections most affected are moved or displayed in relation to each other to better display the pattern relationships. The map may have multiple planes projecting through a center intersection. At least one monitored condition may be positioned one the map so that the weather image expands, develops or moves over the condition the monitored condition may be represented as at least one capital city which may be fixed. In one embodiment monitored sub-conditions are represented as cities on a map which may be fixed. The borders may be shown between the clinically differentiated subsystems as straight lines, curved lines, or another pattern of lines or border indications. The borders may be configured to look similar to borders as between states or counties. The map may be divided into roughly triangular sections which all intersect the center or intersect a center space such as a central circle. A state or subset of the state of the patient or a condition for a single point in time may be shown. The pattern of perturbation inducing forces, perturbations, recovery inducing forces, and recoveries, and or recoveries associated with a condition monitored may be show as a storm cell over, adjacent or proximate to the location associated with that condition. The perturbation associated with a sub-condition may be shown as a storm cell over, adjacent or proximate to a location associated with that sub condition. The objects, data, time series, and data patterns which relate to a cell may be displayed at the same time as the cell or in relation to the cell as by touching, or otherwise selecting a cell.

One embodiment comprises a patient monitoring system for generating dynamic visualizations of clinical conditions comprising a processor programmed to, generate images responsive to a clinical condition on an display having clinical regions which intersect, generate at least one diagnostic region positioned on the display adjacent the intersection of the clinical regions for identifying a clinical condition, and incrementally migrate or expand the image toward the diagnostic region, in response to detection of values or trends suggestive of the presence of the clinical condition, and generate images responsive to a clinical condition on an display having clinical regions which intersect. The processor may generate cells of images responsive to a clinical condition on the display map and migrate, expand, or add new cells in a direction toward the diagnostic region, in response to detection of values or trends suggestive of the presence of the clinical condition. The possessor may generate cells of images comprising or responsive to perturbations of biologic particle densities wherein the cell is comprised of a plurality of organelles responsive to features of the perturbation. The cell may be comprised of a plurality of organelles wherein different organelles are responsive to different features of the perturbation, the features comprising at least a plurality of peak value, slope, magnitude, or percent change.

One embodiment comprises a processor programmed to generate cells of images responsive to a clinical condition on an display map having clinical regions which intersect, generate at least one diagnostic region positioned on the display map adjacent the intersection of the clinical regions for identifying a clinical condition, incrementally migrate, expand, or add new cells in a direction toward the diagnostic region, in response to detection of values or trends suggestive of the presence of the clinical condition. The cells may be responsive to perturbations of biologic particle densities wherein different cells are responsive to different features of the perturbation, the features comprising at least a plurality of peak value, slope, magnitude, or percent change, the processor may aggregate the cells on the map within the specific areas of clinical regions to which the perturbations of the cells corresponds, and may migrate, expand and/or emerge new the cells within the regions overtime in response to changes in the perturbations, the cells providing a unifying motion image on the display map responsive to the aggregate dynamic variations of the perturbations. The processor may generate a display map having clinical regions with specific areas for specific perturbations so that the dynamic image is directly indicative of the actual dynamic patterns of perturbations and may itself be imaged by the processor or another processor for analysis.

One embodiment comprises a patient monitoring system for generating dynamic visualizations of clinical conditions comprising a processor programmed to detect perturbations, generate a display map having clinical regions and markers relating to perturbations, combinations of perturbations, or clinical conditions within the regions, generate dynamic images responsive to the perturbations wherein the dynamic images appear and move in response to variations in the perturbations and in response to new perturbations, in a manner similar to color weather radar over the display map and the markers. The processor may further detect clinical conditions by analyzing the perturbations, project the potential direction of the movement based on the pattern of perturbations, and output an indication on the display of the expected direction of movement of the clinical conditions in spatial relation to the dynamic images.

The Appendix includes one embodiment of a domain specific language script relating to detection and imaging of inflammation, acidosis, a parenteral antibiotic indicating disorder (PAID), pathophysiologic decoherence or divergence (PD), physiologic coherence (or convergence) CONV, systemic inflammatory response syndrome (SIRS) (which is more advanced than the conventional SIRS definition) and varying degrees of sepsis severity, and other conditions.

Figure 22:
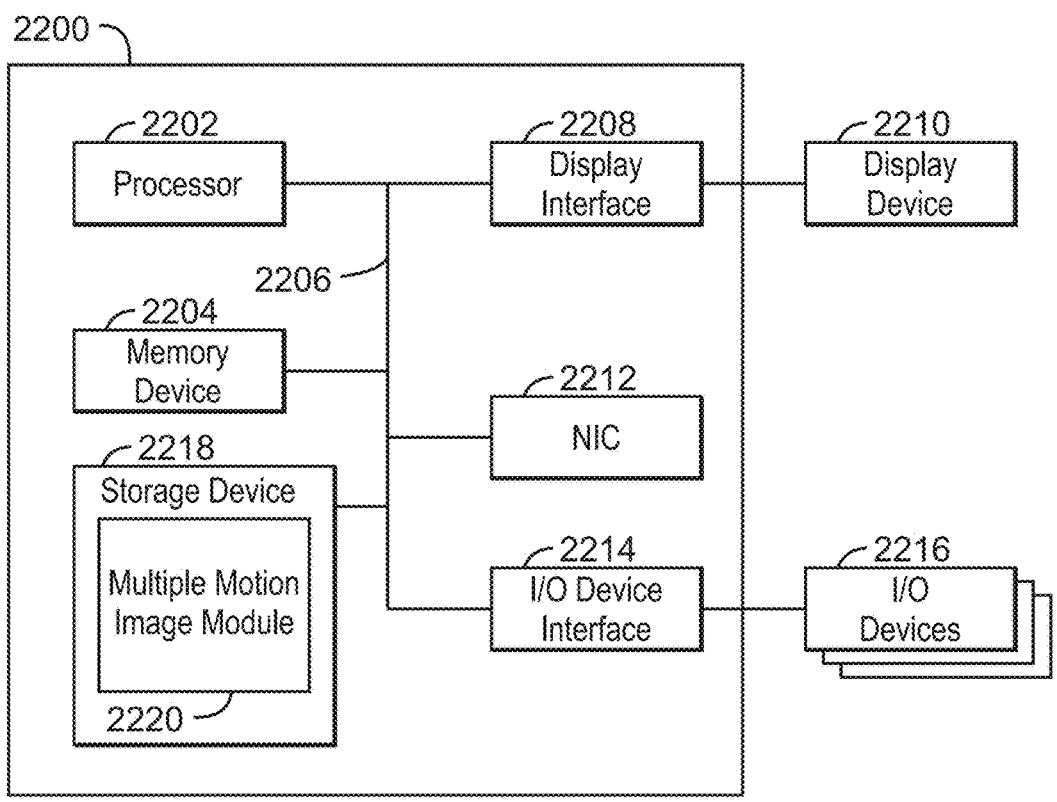
FIG. 22 is a block diagram of an example of a computing device that can generate multiple motion images of at least one clinical condition.

FIG. 22 is a block diagram of an example of a computing device that can generate multiple motion images of at least one clinical condition. The computing device 2200 may be, for example, a mobile phone, laptop computer, desktop computer, or tablet computer, among others. The computing device 2200 may include a processor 2202 that is adapted to execute stored instructions, as well as a memory device 2204 that stores instructions that are executable by the processor 2202. The processor 2202 can be a single core processor, a multi-core processor, a computing cluster, or any number of other configurations. The memory device 2204 can include random access memory, read only memory, flash memory, or any other suitable memory systems. The instructions that are executed by the processor 2202 may be used to implement a method that can generate multiple motion images of at least one clinical condition.

The processor 2202 may also be linked through the system interconnect 2206 (e.g., PCI®, PCI-Express®, HyperTransport®, NuBus, etc.) to a display interface 2208 adapted to connect the computing device 2200 to a display device 2210. The display device 2210 may include a display screen that is a built-in component of the computing device 2200. The display device 2210 may also include a computer monitor, television, or projector, among others, that is externally connected to the computing device 2200. In addition, a network interface controller (also referred to herein as a NIC) 2212 may be adapted to connect the computing device 2200 through the system interconnect 2206 to a network (not depicted). The network (not depicted) may be a cellular network, a radio network, a wide area network (WAN), a local area network (LAN), or the Internet, among others.

The processor 2202 may be connected through a system interconnect 2206 to an input/output (I/O) device interface 2214 adapted to connect the computing device 2200 to one or more I/O devices 2216. The I/O devices 2216 may include, for example, a keyboard and a pointing device, wherein the pointing device may include a touchpad or a touchscreen, among others. The I/O devices 2216 may be built-in components of the computing device 2200, or may be devices that are externally connected to the computing device 2200.

In some embodiments, the processor 2202 may also be linked through the system interconnect 2206 to a storage device 2218 that can include a hard drive, an optical drive, a USB flash drive, an array of drives, or any combinations thereof. In some embodiments, the storage device 2218 can include a multiple motion image module 2220. The multiple motion image 2220 can receive medical data relating to a clinical condition. In some examples, the motion image module 220 can also generate a first motion image responsive to the medical data, the first motion image displaying a clinical condition in a display configured to appear to a user as similar to a storm on a color weather radar map. In some embodiments, animation of the clinical condition over time is generated as a series of images of increasing time to display a moving picture of the clinical condition, wherein the map is divided into sections that represent clinically differentiated regions. The multiple motion image module 2220 can also generate a second motion image which displays the same clinical condition shown in the first motion image as a second image along a time axis, the second motion image growing along the time axis over time, so that the position of a static image along the first motion image at a single point or segment in time can be identified on the second motion image along the time axis so that the relationship and position of the static image in the first motion image to the second motion image is readily viewed.

It is to be understood that the block diagram of FIG. 22 is not intended to indicate that the computing device 2200 is to include all of the components shown in FIG. 22. Rather, the computing device 2200 can include fewer or additional components not illustrated in FIG. 22 (e.g., additional memory components, embedded controllers, additional modules, additional network interfaces, etc.). Furthermore, any of the functionalities of the multiple motion module 2220 may be partially, or entirely, implemented in hardware and/or in the processor 2202. For example, the functionality may be implemented with an application specific integrated circuit, logic implemented in an embedded controller, or in logic implemented in the processor 2202, among others.

Figure 23:
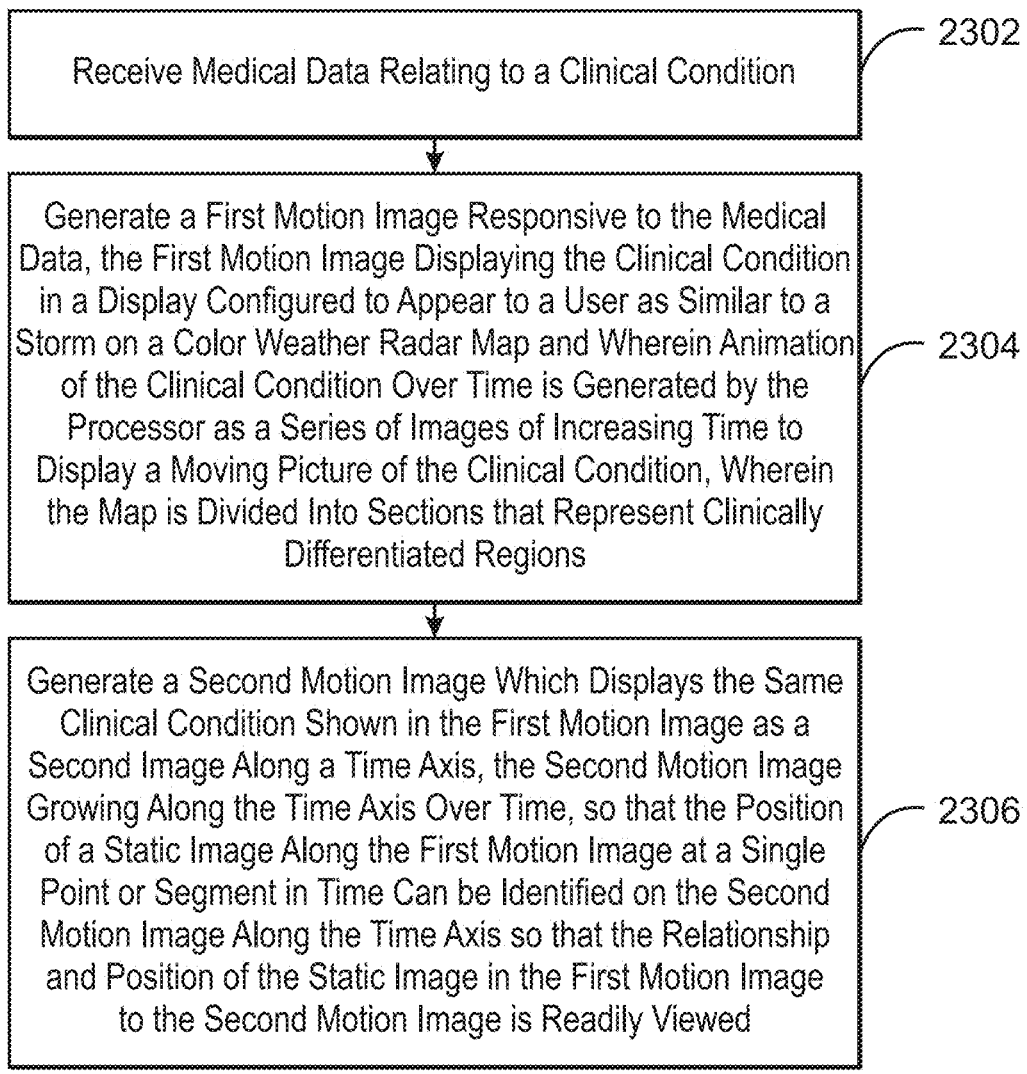
FIG. 23 is a process flow diagram of an example method for generating multiple motion images.

FIG. 23 is a process flow diagram of an example method for generating multiple motion images. The method 2300 can be implemented with a computing device, such as the computing device 2200 of FIG. 22.

At block 2302, the multiple motion image module 2220 can receive medical data relating to a clinical condition. At block 2304, the multiple motion image module 2220 can generate a first motion image responsive to the medical data, the first motion image displaying the clinical condition in a display configured to appear to a user as similar to a storm on a color weather radar map and wherein animation of the clinical condition over time is generated by the processor as a series of images of increasing time to display a moving picture of the clinical condition, wherein the map is divided into sections that represent clinically differentiated regions. At block 2306, the multiple motion image module 2220 can generate a second motion image which displays the same clinical condition shown in the first motion image as a second image along a time axis, the second motion image growing along the time axis over time, so that the position of a static image along the first motion image at a single point or segment in time can be identified on the second motion image along the time axis so that the relationship and position of the static image in the first motion image to the second motion image is readily viewed.

The process flow diagram of FIG. 23 is not intended to indicate that the operations of the method 2300 are to be executed in any particular order, or that all of the operations of the method 2300 are to be included in every case. Additionally, the method 2300 can include any suitable number of additional operations.

One of ordinary skill in the art will appreciate the technical effect described herein which provides improved and alternative motion image visualizations of a medical condition. Some embodiments described herein have the effect of generating multiple motion images. Conditional language used herein, such as, among others, "can," "may," "might," "could," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment.

While the above detailed description has shown, described, and pointed out novel features as applied to various embodiments, it will be understood that various omissions, substitutions, and changes in the form and details of the device or process illustrated can be made without departing from the spirit of the disclosure. As will be recognized, certain embodiments of the inventions described herein can be embodied within a form that does not provide all of the features and benefits set forth herein, as some features can be used or practiced separately from others. The scope of the inventions is indicated by the appended claims rather than by the foregoing description. All changes which come within the meaning and range of equivalency of the claims are to be embraced within their scope.

Example Embodiments

In some embodiments, a patient monitoring system comprises at least one processor programmed to receive medical data relating to a clinical condition. The processor can also be programmed to generate a first motion image responsive to the medical data, the first motion image displaying the clinical condition in a display configured to appear to a user as similar to a storm on a color weather radar map and wherein animation of the clinical condition over time is generated by the processor as a series of images of increasing time to display a moving picture of the clinical condition, wherein the map is divided into sections that represent clinically differentiated regions. The processor can also be programmed to generate a second motion image which displays the same clinical condition shown in the first motion image as a second image along a time axis, the second motion image growing along the time axis over time, so that the position of a static image along the first motion image at a single point or segment in time can be identified on the second motion image along the time axis so that the relationship and position of the static image in the first motion image to the second motion image is readily viewed. In some examples, the processor is also programmed to provide a time-lapsed image of the clinical condition, the first motion image and the second motion image being time linked so that the first motion image and the second motion image evolve over time simultaneously.

In some examples, treatment events are positioned along the time axis of the second motion image. Additionally, a trellis display of at least two patients can be displayed. In some examples, the trellis display is sorted by characteristics of the storm. Furthermore, in some embodiments, a histogram is generated adjacent the first motion image and static images of the condition are viewable by selecting points in time on the histogram.

In some examples, the second motion image is shown with relationship to patient treatment events. In some embodiments, specific simultaneous times of the first and second motion images are viewable by selecting said times. In some examples, the clinical condition is sepsis.

In some embodiments, a patient monitoring system comprising at least one processor can be programmed to generate an image which displays a clinical condition in a display configured to appear to a user as similar to a storm on a color weather radar display map. In some examples, a time-lapsable animation of a patient state over time is generated by the processor as a series of images of increasing time to display a moving picture of the clinical condition wherein the map is divided into sections that represent clinically differentiated regions and wherein at least one possible future state of the clinical condition is determined and presented on the display as a potential storm path. In some embodiments, the clinical condition can be sepsis.

In some examples, the potential storm path is shown on the map along with a determined level of probability. Additionally, the image can include a two dimensional user-facing map, wherein time extends along an axis away from the user facing map so that each user-facing image on the two dimensional user-facing map comprises a segment of time along the image of the condition. In some embodiments, the map may be scrolled forward or backward over time to view different two dimensional images of the condition at different segments of time of the condition. In some examples, the clinical condition is sepsis.

Additionally, in some embodiments, a second image is generated comprising a second two dimensional user-facing map, wherein time extends along one axis of the two dimensional map so that an image on the second two dimensional user-facing map can extend over the entire duration of the clinical condition.

In some embodiments, the image is a three dimensional user-facing map, wherein time extends along an axis away from the user facing map so that each user-facing image on the two dimensional user-facing map comprises a segment of time along the image of the condition. In some examples, the map may be scrolled forward or backward over time with the three dimensional image of the condition moving toward the two dimensional user-facing map when the image is scrolled forward over time.

APPENDIX TO THE SPECIFICATION define stream Albumin as "Albumin"
    profile severity
        when low
            value 3.7, 3.6, 3.5, 3.4, 3.2, 3.0, 2.8, 2.6, 2.4, 2.2, 2.1, 2.0, 1.9, 1.8, 1.7
        when fall
            min 3.7, 3.6, 3.5, 3.4, 3.2, 3.0, 2.8, 2.6, 2.4, 2.2, 2.1, 2.0, 1.9, 1.8, 1.7
            magnitude 0.4, 0.5, 0.6, 0.7, 0.8, 0.9, 1.0, 1.2, 1.4, 1.6, 1.8, 2, 2.2, 2.4, 2.6
    qualify
        fall on magnitude
        locate in metabolic;
define stream AnionGap as "Anion Gap"
    profile severity
        when high
            value 12, 12.5, 13, 13.5, 14, 14.5, 15, 15.5, 16, 17, 18, 19, 20, 21, 22
        when rise
            max 12, 12.5, 13, 13.5, 14, 14.5, 15, 15.5, 16, 17, 18, 19, 20, 21, 22
            magnitude 1, 2, 3, 3.5, 4, 4.5, 5, 5.5, 6, 6.5, 7, 7.5, 8, 8.5, 9
    qualify
        rise on magnitude
        locate in acidbase;
define stream Bands as "Bands"
    profile severity
        when high
            value start with 4 increase by 1
        when rise
            max start with 4 increase by 1
            magnitude start with 3 increase by 1
    qualify
        rise on magnitude
        locate in inflammatory;
define stream BandsAbs as "Bands Abs"
    profile severity
        when high
            value 1.2, 1.4, 1.6, 1.7, 1.8, 1.9, 2.0, 2.2, 2.4, 2.6, 2.8, 3.0, 3.2, 3.6, 4.0
        when rise
            max 1.2, 1.4, 1.6, 1.7, 1.8, 1.9, 2.0, 2.2, 2.4, 2.6, 2.8, 3.0, 3.2, 3.6, 4.0
            magnitude 0.1, 0.15, 0.18, 0.2, 0.25, 0.3, 0.35, 0.4, 0.5, 0.6, 0.8, 1.0, 1.5, 2.0, 2.5
    qualify
        rise on magnitude
        locate in inflammatory;
define stream BaseDeficit as "Arterial Base Deficit"
    profile severity
        when high
            value start with 1 increase by 0.3
        when rise
            max start with 0.3 increase by 0.3
            slopeindays start with 0.3 increase by 0.2
            magnitude start with 0.3 increase by 0.2
            percentchange start with 10 increase by 5
        when fall
            slopeindays start with −0.3 decrease by 0.2
    qualify
        rise on magnitude
        locate in acidbase;
define stream Bicarb as "Bicarbonate", "HCO3, Arterial", "TCO2, Arterial", "Carbon Dioxide"
    profile severity
        when low
            value 24, 23.5, 23.2, 23, 22, 21, 20, 19, 18, 17, 16, 15, 14, 13, 12
        when fall
            min 24, 23.5, 23.2, 23, 22, 21, 20, 19, 18, 17, 16, 15, 14, 13, 12
            magnitude start with 1.5 increase by 0.5
    qualify
        fall on magnitude
        locate in acidbase;
define stream BPSystolic as "BP Systolic", "ABPSys"
    profile severity
        when low
            value start with 100 decrease by 5
        when fall
            min start with 100 decrease by 5
            magnitude start with 20 increase by 2
    qualify
        fall on magnitude
        locate in cardiac;
define stream BPMean as "BP Mean", "ABPMean"
    profile severity
        when low
            value start with 70 decrease by 2
        when fall
            min start with 70 decrease by 2
            magnitude start with 10 increase by 2
    qualify
        fall on magnitude
        locate in cardiac;
define stream BUN as "BUN"
    profile severity
        when high
            value 23, 24, 25, 26, 27, 28, 30, 32, 34, 36, 38, 40, 42, 44, 46
        when rise
            slopeindays 1, 2, 3, 4, 5, 6, 7, 8, 9, 10, 11, 12, 13, 14, 15
            magnitude 2, 4, 6, 8, 10, 12, 14, 16, 18, 20, 22, 24, 26, 28, 30
            percentchange 2, 3, 4, 6, 8, 16, 20, 24, 28, 32, 36, 40, 44, 48, 52
        when low
            value 1|10, 2|9, 3|8, 4|7, 5|6, 6|5, 7|4, 8|3, 9|2, 1|11, 1|10
        when fall
            slopeindays −1, −2, −3, −4, −5, −6, −7, −8, −9, −10, −11, −12, −13, −14, − magnitude 2, 4, 6, 8, 10, 12, 14, 16, 18, 20, 22, 24, 26, 28, 30
percentchange 5, 8, 10, 14, 18, 22, 26, 30, 34, 38, 42, 46, 50, 54,
qualify
rise on magnitude
fall on magnitude
locate in renal;
define stream Calcium as "Calcium"
profile severity
when low
value 8.6, 8.4, 8.2, 8, 7.8, 7.6, 7.4, 7.2, 7, 6.8, 6.4, 6, 5.5, 5, 4.5
when fall
min 8.6, 8.4, 8.2, 8, 7.8, 7.6, 7.4, 7.2, 7, 6.8, 6.4, 6, 5.5, 5, 4.5
magnitude 0.4, 0.5, 0.6, 0.7, 0.8, 0.9, 1.0, 1.2, 1.4, 1.6, 1.8, 2.0, 2.2, 2.4, 2.6
qualify
fall on magnitude
locate in electrolytic;
define stream Chloride as "Chloride"
profile severity
when high
value 106, 107, 108, 109, 110, 111, 112, 113, 114, 115, 116, 117, 118, 119, 120
when rise
slopeindays 1, 1.5, 2, 3, 3.5, 4, 5, 5.5, 6, 6.5, 7, 7.5, 8, 8.5, 9
magnitude 1, 2, 3, 4, 5, 6, 7, 8, 9, 10, 11, 12, 13, 14, 15
percentchange 10, 11, 12, 13, 14, 15, 16, 17, 18, 19, 20, 21, 22, 23, 24
when low
value 100, 99, 98, 97, 96, 95, 94, 93, 92, 91, 90, 89, 88, 87, 86
when fall
slopeindays −1, −1.5, −2, −3, −3.5, −4, −5, −5.5, −6, −6.5, −7, −7.5, −8, −8.5, −9
magnitude 1, 2, 3, 4, 5, 6, 7, 8, 9, 10, 11, 12, 13, 14, 15
percentchange 10, 11, 12, 13, 14, 15, 16, 17, 18, 19, 20, 21, 22, 23, 24
qualify
rise on magnitude
fall on magnitude
locate in electrolytic;
define stream Creatinine as "Creatinine"
profile severity
when high
value 1, 1.05, 1.1, 1.15, 1.2, 1.25, 1.3, 1.35, 1.4, 1.45, 1.5, 1.55, 1.6, 1.7, 1.8
when rise
slopeindays 0.01, 0.02, 0.03, 0.06, 0.08, 0.1, 0.12, 0.14, 0.16, 0.2, 0.25, 0.3, 0.4, 0.5, 0.6
magnitude 0.02, 0.04, 0.06, 0.1, 0.15, 0.2, 0.3, 0.35, 0.4, 0.45, 0.5, 0.55, 0.6, 0.7, 0.8
percentchange 2, 3, 4, 5, 6, 8, 10, 12, 14, 16, 20, 24, 28, 32, 36
when low
value 0.6, 0.5, 0.4, 0.38, 0.36, 0.34, 0.32, 0.31, 0.3, 0.28, 0.26, 0.24, 0.22, 0.20, 0.18
when fall
slopeindays −0.01, −0.02, −0.03, −0.06, −0.08, −0.1, −0.12, −0.14, −0.16, −0.2, −0.25, −0.3, −0.4, −0.5, −0.6
magnitude 0.02, 0.04, 0.06, 0.1, 0.15, 0.2, 0.3, 0.35, 0.4, 0.45, 0.5, 0.55, 0.6, 0.7, 0.8
percentchange 2, 3, 4, 5, 6, 8, 10, 12, 14, 16, 20, 24, 28, 32, 36
qualify
rise on magnitude and percentchange
fall on magnitude and percentchange
locate in renal;
define stream eGFR as "eGFR"
profile severity
when low
value 7159, 8156, 9152, 10148, 11144, 12140, 13134, 14130, 15126
when fall
slopeindays −1, −2, −3, −4, −5, −6, −7, −8, −9, −10, −11, −12, −13, −14, −15
magnitude 1, 2, 3, 4, 5, 6, 7, 8, 9, 10, 11, 12, 13, 14, 15
percentchange 2, 4, 6, 8, 10, 12, 14, 16, 18, 20, 22, 24, 26, 28, 30
qualify
fall on magnitude
locate in renal;
define stream Fibrinogen as "Fibrinogen"
profile severity
when low
value start with 200 decrease by 7
when fall
min start with 40 decrease by 3
slopeindays start with −20 decrease by 3
magnitude start with 40 increase by 3
percentchange start with 7 increase by 1
when rise
slopeindays start with 20 increase by 3
qualify
fall on magnitude
locate in haemostatic;
define stream FIO2 as "FIO2"
profile severity
when high
value start with 24 increase by 6
when rise
slopeindays start with 4 increase by 2
magnitude start with 4 increase by 2
percentchange start with 20 increase by 5
when fall
slopeindays start with −4 decrease by 2
qualify
rise on magnitude
locate in respiratory;
define stream GlucoseAny as "Glucose", "Fingerstick Glucose"
profile severity
when high
value start with 200 increase by 20
when rise
max start with 50 increase by 10
slopeindays start with 40 increase by 10
magnitude start with 50 increase by 10
percentchange start with 205 increase by 2
when low
value start with 55 decrease by 2
when fall
slopeindays start with −40 decrease by 10
qualify
rise on magnitude
locate in metabolic;

define stream Hematocrit as "Hematocrit"
  profile severity
    when high
      value 43, 44, 45, 45.4, 45.8, 46.2, 46.6, 47, 47.4,
        47.8, 48.2, 48.6, 49, 49.5, 50
    when rise
      slopeindays 0.1, 0.2, 0.3, 0.4, 0.5, 0.6, 0.7, 0.8, 0.9,
        1.0, 1.2, 1.4, 1.6, 1.8, 2.0
      magnitude 0.2, 0.4, 0.6, 0.8, 1.0, 1.2, 1.4, 1.6, 1.8,
        2.0, 2.4, 2.8, 3.2, 3.6, 4.0
      percentchange 0.5, 0.75, 1.0, 1.6, 2.0, 2.4, 2.8, 3.2,
        3.6, 4.0, 4.8, 5.6, 6.4, 7.2, 8.0
    when low
      value 38, 37, 36, 35.5, 35, 34.5, 34, 33.5, 33, 32.5,
        32, 31.5, 31, 30.5, 30
    when fall
      slopeindays −0.1, −0.2, −0.3, −0.4, −0.5, −0.6, −0.7,
        −0.8, −0.9, −1.0, −1.2, −1.4, −1.6, −1.8, −2.0
      magnitude 0.2, 0.4, 0.6, 0.8, 1.0, 1.2, 1.4, 1.6, 1.8,
        2.0, 2.4, 2.8, 3.2, 3.6, 4.0
      percentchange 0.5, 0.75, 1.0, 1.6, 2.0, 2.4, 2.8, 3.2,
        3.6, 4.0, 4.8, 5.6, 6.4, 7.2, 8.0
  qualify
    rise on magnitude
    fall on magnitude
  locate in Hematologic;
define stream HemoglobinAny as "Hemoglobin", "Arterial
Hemoglobin", "Hgb"
  profile severity
    when low
      value start with 11 decrease by 0.5
    when fall
      min start with 0.5 decrease by 0.02
      slopeindays start with −0.5 decrease by 0.05
      magnitude start with 0.5 increase by 0.2
      percentchange start with 8 increase by 1
    when rise
      slopeindays start with 0.5 increase by 0.05
  qualify
    fall on magnitude
  locate in hematologic;
define stream IonCalcium as "Ionized Calcium"
  profile severity
    when low
      value 4.7, 4.6, 4.5, 4.4, 4.3, 4.2, 4.1, 4.0, 3.9, 3.8, 3.6,
        3.4, 3.2, 3.0, 2.8
    when fall
      min 4.7, 4.6, 4.5, 4.4, 4.3, 4.2, 4.1, 4.0, 3.9, 3.8, 3.6,
        3.4, 3.2, 3.0, 2.8
      magnitude start with 0.4 increase by 0.2
  qualify
    fall on magnitude
  locate in electrolytic;
define stream Lactate as "Lactate"
  profile severity
    when high
      value 1.8, 2.0, 2.2, 2.4, 2.6, 2.8, 3, 3.5, 4, 5, 6, 7, 8,
        9, 10
    when rise
      max 1.8, 2.0, 2.2, 2.4, 2.6, 2.8, 3, 3.5, 4, 5, 6, 7, 8,
        9, 10
      magnitude 0.2, 0.3, 0.4, 0.5, 0.6, 0.7, 1.0, 1.5, 2.0,
        2.5, 3.0, 3.5, 4.0, 4.5, 5.0
  qualify
    rise on magnitude
  locate in acidbase;
define stream LDH as "LDH"
  profile severity
    when high
      value 140, 150, 160, 170, 180, 200, 220, 240, 260,
        280, 300, 320, 340, 360, 380
    when rise
      slopeindays 5, 6, 7, 8, 9, 10, 20, 30, 40, 50, 60, 70,
        80, 90, 100
      percentchange 7, 8, 9, 10, 20, 30, 40, 50, 60, 70, 80,
        90, 100, 150, 200
    when low
      value 80, 75, 70, 65, 60, 55, 50, 45, 40, 35, 30, 25,
        20, 10, 0
    when fall
      slopeindays −4, −5, −6, −7, −8, −9, −10, −15, −20,
        −25, −30, −35, −40, −45, −50
      percentchange 5, 6, 7, 8, 9, 10, 15, 20, 30, 40, 50, 60,
        70, 80, 90
  qualify
    rise on percentchange
    fall on percentchange
  locate in misc;
define stream Lymphocytes as "Lymphocytes"
  profile severity
    when high
      value 40, 41, 42, 43, 44, 45, 46, 47, 48, 49, 50, 51,
        52, 53, 54
    when rise
      slopeindays 2, 3, 4, 5, 6, 7, 8, 9, 10, 11, 12, 13, 14,
        15, 16
      magnitude 4, 6, 8, 10, 12, 14, 16, 18, 20, 22, 24, 26,
        28, 30, 32
      percentchange 4, 6, 8, 10, 12, 14, 16, 18, 20, 22, 24,
        26, 28, 30, 32
  qualify
    rise on magnitude
  locate in inflammatory;
define stream LymphocytesAbs as "Lymphocytes Abs"
  profile severity
    when high
      value 3.8, 3.9, 4.0, 4.2, 4.4, 4.8, 5.5, 6, 6.5, 7, 7.5, 8,
        9, 10, 11
    when rise
      slopeindays 0.025, 0.05, 0.1, 0.15, 0.2, 0.25, 0.3, 0.4,
        0.6, 0.8, 1.0, 1.2, 1.4, 1.6, 1.8
      percentchange 7, 8, 9, 10, 20, 30, 40, 50, 60, 70, 80,
        90, 100, 150, 200
    when low
      value 1.1, 1.0, 0.9, 0.8, 0.75, 0.7, 0.65, 0.6, 0.55, 0.5,
        0.45, 0.4, 0.3, 0.2, 0.1
    when fall
      slopeindays −0.025, −0.05, −0.1, −0.15, −0.2, −0.25,
        −0.3, −0.4, −0.6, −0.8, −1.0, −1.2, −1.4, −1.6, −1.8
      percentchange 2, 4, 6, 8, 10, 15, 20, 25, 30, 40, 50,
        60, 70, 80, 90
  qualify
    rise on percentchange
    fall on percentchange
  locate in inflammatory;
define stream MetamyelocyteNeut as "Metamyelocytes"
  profile severity
    when high
      value 1410.00001, 1510.001
  locate in inflammatory;
define stream MinuteVolume as "Minute Volume"
  profile severity
    when high
      value start with 12 increase by 0.6

```
            when rise
                slopeindays start with 2 increase by 0.5
                magnitude start with 2 increase by 0.5
                percentchange start with 20 increase by 5
            when fall
                slopeindays start with -2 decrease by 0.5
        qualify
            rise on magnitude
        locate in respiratory;
    define stream Monocytes as "Monocytes"
        profile severity
            when high
                value 10, 11, 12, 13, 14, 15, 16, 17, 18, 19, 20, 21,
                    22, 23, 24
            when rise
                max 1, 2, 3, 4, 5, 6, 7, 8, 9, 10, 11, 12, 13, 14, 15
                slopeinhours 0.2, 0.4, 0.6, 1.0, 1.4, 1.8, 2.2, 2.6, 3.0,
                    3.4, 3.8, 4.2, 4.6, 5.0, 5.4
                percentchange 4, 5, 6, 7, 8, 9, 10, 20, 30, 40, 50, 60,
                    70, 80, 100
            when low
                value 1|4, 4|3, 7|2, 10|1, 13|0
            when fall
                /* min 1, 2, 3, 4, 5, 6, 7, 8, 9, 10, 11, 12, 13, 14, 15
                    */
                slopeinhours -0.2, -0.4, -0.6, -1.0, -1.4, -1.8, -2.2,
                    -2.6, -3.0, -3.4, -3.8, -4.2, -4.6, -5.0, -5.4
                percentchange 4, 5, 6, 7, 8, 9, 10, 20, 30, 40, 50, 60,
                    70, 80, 100
        qualify
            rise on percentchange
            fall on percentchange
        locate in inflammatory;
    define stream Neutrophils as "Neutrophils"
        profile severity
            when high
                value 70, 72, 74, 76, 78, 80, 82, 84, 86, 88, 90, 92,
                    94, 96, 98
            when rise
                slopeindays 4, 6, 8, 10, 12, 14, 16, 18, 20, 22, 24, 26,
                    28, 30, 32
                magnitude 4, 6, 8, 10, 12, 14, 16, 18, 20, 24, 28, 32,
                    36, 40, 44
                percentchange 4, 6, 8, 10, 14, 18, 24, 28, 32, 36, 40,
                    44, 48, 52, 56
            when low
                value 51, 50, 49, 48, 47, 46, 44, 42, 40, 38, 34, 30,
                    26, 22, 18
            when fall
                slopeindays -4, -6, -8, -10, -12, -14, -16, -18,
                    -20, -22, -24, -26, -28, -30, -32
                magnitude 4, 6, 8, 10, 12, 14, 16, 18, 20, 24, 28, 32,
                    36, 40, 44
                percentchange 4, 6, 8, 10, 14, 18, 24, 28, 32, 36, 40,
                    44, 48, 52, 56
        qualify
            rise on magnitude
            fall on magnitude
        locate in inflammatory;
    define stream NeutrophilsAbs as "Neutrophils Abs"
        profile severity
            when high
                value 8.5, 9, 9.5, 10, 10.5, 11, 12, 13, 14, 15, 16, 17,
                    18, 19, 21
            when rise
                max 8.5, 9, 9.5, 10, 10.5, 11, 12, 13, 14, 15, 16, 17,
                    18, 19, 21
                magnitude start with 1 increase by 1
            when low
                value start with 2 decrease by 0.1
            when fall
                min start with 3 decrease by 0.2
        qualify
            rise on magnitude
        locate in inflammatory;
    define stream NucleatedRBC as "Nucleated RBC"
        profile severity
            when high
                value 14|0.00001, 15|0.001
        locate in inflammatory;
    define stream NucleatedRBCabs as "Nucleated RBC Abs"
        profile severity
            when high
                value 14|0.00001, 15|0.001
        locate in inflammatory;
    define stream OxSat as "SpO2", "02 SAT, Arterial", "SaO2"
        profile severity
            when low
                value start with 93 decrease by 1
            when fall
                min start with 2 decrease by 0.05
                slopeindays start with -4 decrease by 2
                magnitude start with 4 increase by 2
                percentchange start with 4 increase by 1
            when rise
                slopeindays start with 4 increase by 2
        qualify
            fall on magnitude
        locate in respiratory;
    define stream PHBlood as "pH, Arterial", "PH"
        profile severity
            when low
                value start with 7.33 decrease by 0.02
            when fall
                magnitude start with 0.0020 increase by 0.0015
        qualify
            fall on magnitude
        locate in acidbase;
    define stream PaCO2 as "Arterial PaCO2"
        profile severity
            when low
                value start with 34 decrease by 1
            when fall
                min start with 4 decrease by 0.5
                slopeindays start with -4 decrease by 0.5
                magnitude start with 4 increase by 0.5
                percentchange start with 12 increase by 2
            when rise
                slopeindays start with 4 increase by 0.5
        qualify
            fall on magnitude
        locate in respiratory;
    define stream Platelets as "Platelets"
        profile severity
            when low
                value 160, 150, 140, 130, 120, 110, 100, 90, 80, 70,
                    60, 50, 40, 30,
            when fall
                min 160, 150, 140, 130, 120, 110, 100, 90, 80, 70, 60,
                    50, 40, 30,
                magnitude start with 40 increase by 12
        qualify
            fall on magnitude
        locate in haemostatic;
```

```
define stream Potassium as "Potassium"
    profile severity
        when high
            value 4.8, 4.9, 5.0, 5.1, 5.2, 5.3, 5.4, 5.5, 5.6, 5.7, 5.8,
                5.9, 6.0, 6.1, 6.2
        when rise
            slopeindays 0.02, 0.04, 0.06, 0.08, 0.10, 0.12, 0.14,
                0.18, 0.22, 0.26, 0.30, 0.34, 0.38, 0.42, 0.46
            magnitude 0.04, 0.08, 0.12, 0.16, 0.20, 0.24, 0.26,
                0.30, 0.34, 0.38, 0.42, 0.46, 0.50, 0.54, 0.58
            percentchange 1, 2, 3, 4, 5, 6, 7, 8, 9, 10, 11, 12, 13,
                14, 15
        when low
            value 3.7, 3.6, 3.5, 3.4, 3.3, 3.2, 3.1, 3.0, 2.9, 2.8, 2.7,
                2.6, 2.5, 2.4, 2.3
        when fall
            slopeindays −0.02, −0.04, −0.06, −0.08, −0.10,
                −0.12, −0.14, −0.18, −0.22, −0.26, −0.30, −0.34,
                −0.38, −0.42, −0.46
            magnitude 0.04, 0.08, 0.12, 0.16, 0.20, 0.24, 0.26,
                0.30, 0.34, 0.38, 0.42, 0.46, 0.50, 0.54, 0.58
            percentchange 1, 2, 3, 4, 5, 6, 7, 8, 9, 10, 11, 12, 13,
                14, 15
    qualify
        rise on magnitude
        fall on magnitude
    locate in electrolytic;
define stream HR as "Pulse", "Heart Rate"
    profile severity
        when high
            value start with 90 increase by 5
        when rise
            slopeindays start with 15 increase by 2
            magnitude start with 15 increase by 2
            percentchange start with 20 increase by 5
        when fall
            min start with 90 decrease by 5
            magnitude start with 15 increase by 5
    qualify
        rise on magnitude
        fall on magnitude
    locate in cardiac;
define stream Procalcitonin as "Procalcitonin"
    profile severity
        when high
            value start with 0.15 increase by 0.05
        when rise
            slopeindays start with 0.2 increase by 0.03
            magnitude start with 0.2 increase by 0.05
            percentchange start with 10 increase by 2
        when fall
            slopeindays start with −0.2 decrease by 0.03
    qualify
        rise on magnitude
    locate in inflammatory;
define stream RespiratoryRate as "Respiratory Rate"
    profile severity
        when high
            value start with 18 increase by 1
        when rise
            max start with 18 increase by 1
            magnitude start with 4 increase by 1
    qualify
        rise on magnitude
    locate in respiratory;
define stream SegsAbs as "Segs Abs"
    profile severity
        when high
            value 6.5, 6.75, 7, 7.2, 7.4, 7.6, 8, 9, 10, 11, 13, 15,
                17, 19, 21
        when rise
            slopeindays 0.25, 0.5, 0.75, 1, 2, 3, 4, 5, 6, 8, 10, 12,
                14, 16, 18
            percentchange 4, 6, 8, 10, 20, 30, 40, 50, 60, 70, 80,
                90, 100, 120, 140
        when low
            value 2, 1.9, 1.7, 1.6, 1.5, 1.4, 1.3, 1.2, 1.1, 1, 0.8,
                0.6, 0.5, 0.4, 0.3
        when fall
            slopeindays −0.1, −0.15, −0.2, −0.3, −0.4, −0.5,
                −0.75, −1.0, −1.5, −2, −2.5, −3, −3.5, −4, −4.5
            percentchange 4, 5, 6, 8, 10, 12, 15, 20, 30, 40, 50,
                60, 70, 80, 90
    qualify
        rise on percentchange
        fall on percentchange
    locate in inflammatory;
define stream Segs as "Segs"
    profile severity
        when high
            value 61, 62, 63, 64, 66, 68, 70, 74, 78, 84, 88, 92,
                94, 96, 98
        when rise
            slopeindays 1, 2, 3, 4, 5, 6, 7, 8, 9, 10, 11, 12, 13, 14,
                15
            magnitude 2, 3, 4, 6, 8, 10, 12, 14, 16, 18, 20, 22, 24,
                26, 30
            percentchange 2, 3, 4, 5, 8, 12, 16, 20, 25, 30, 40, 50,
                60, 70, 80
        when low
            value 34, 33, 32, 31, 30, 28, 26, 24, 22, 20, 18, 14,
                10, 8, 6
        when fall
            slopeindays −1, −2, −3, −4, −5, −6, −7, −8, −9, −10,
                −11, −12, −13, −14, −15
            magnitude 2, 3, 4, 6, 8, 10, 12, 14, 16, 18, 20, 22, 24,
                26, 30
            percentchange 2, 3, 4, 5, 8, 12, 16, 20, 25, 30, 40, 50,
                60, 70, 80
    qualify
        rise on magnitude
        fall on magnitude
    locate in inflammatory;
define stream Sodium as "Sodium"
    profile severity
        when high
            value 143, 144, 145, 146, 147, 148, 149, 150, 151,
                152, 153, 154, 155, 156, 157
        when rise
            slopeindays 0.4, 0.6, 0.8, 1, 1.4, 1.8, 2.2, 2.6, 3, 3.4,
                3.8, 4.2, 4.6, 5.0, 5.4
            magnitude 1, 2, 2.4, 2.8, 3.2, 3.6, 4, 4.4, 4.8, 5.2, 5.6,
                6, 6.4, 6.8, 7.2
            percentchange 0.5, 0.8, 1, 1.4, 1.6, 1.8, 2, 2.4, 2.8,
                3.2, 3.6, 4.0, 4.4, 4.8, 5.2
        when low
            value 137, 136, 135, 134, 133, 132, 131, 130, 129,
                128, 127, 126, 125, 124, 123
        when fall
            slopeindays −0.4, −0.6, −0.8, −1, −1.4, −1.8, −2.2,
                −2.6, −3, −3.4, −3.8, −4.2, −4.6, −5.0, −5.4
            magnitude 1, 2, 2.4, 2.8, 3.2, 3.6, 4, 4.4, 4.8, 5.2, 5.6,
                6, 6.4, 6.8, 7.2
``` percentchange 0.5, 0.8, 1, 1.4, 1.6, 1.8, 2, 2.4, 2.8, 3.2, 3.6, 4.0, 4.4, 4.8, 5.2
qualify
rise on magnitude
fall on magnitude
locate in electrolytic;
define stream TemperatureC as "Temperature C"
profile severity
when high
value 37.22, 37.33, 37.44, 37.56, 37.67, 37.78, 38.06, 38.33, 38.61, 38.89, 39.44, 40.00, 40.56, 41.11, 41.67
when rise
max 37.22, 37.33, 37.44, 37.56, 37.67, 37.78, 38.06, 38.33, 38.61, 38.89, 39.44, 40.00, 40.56, 41.11, 41.67
magnitude 0.22, 0.28, 0.33, 0.39, 0.44, 0.50, 0.56, 0.78, 1.00, 1.22, 1.44, 1.67, 1.78, 1.89, 2.00
when low
value start with 36.33 decrease by 0.056
when fall
min start with 36.33 decrease by 0.056
magnitude 0.22, 0.28, 0.33, 0.39, 0.44, 0.50, 0.56, 0.78, 1.00, 1.22, 1.44, 1.67, 1.78, 1.89, 2.00
qualify
rise on magnitude
fall on magnitude
locate in inflammatory;
define stream TemperatureF as "Temperature F"
profile severity
when high
value 99, 99.2, 99.4, 99.6, 99.8, 100, 100.5, 101, 101.5, 102, 103, 104, 105, 106, 107
when rise
max 99, 99.2, 99.4, 99.6, 99.8, 100, 100.5, 101, 101.5, 102, 103, 104, 105, 106, 107
magnitude 0.4, 0.5, 0.6, 0.7, 0.8, 0.9, 1.0, 1.4, 1.8, 2.2, 2.6, 3.0, 3.2, 3.4, 3.6
when low
value start with 97.4 decrease by 0.1
when fall
min start with 97.4 decrease by 0.1
magnitude 0.4, 0.5, 0.6, 0.7, 0.8, 0.9, 1.0, 1.4, 1.8, 2.2, 2.6, 3.0, 3.2, 3.4, 3.6
qualify
rise on magnitude
fall on magnitude
locate in inflammatory;
define stream WBC as "WBC"
profile severity
when high
value 12.5, 13, 13.5, 14, 15.5, 16, 17, 18, 19, 20, 21, 22, 23, 25, 27
when rise
max 12.5, 13, 13.5, 14, 15.5, 16, 17, 18, 19, 20, 21, 22, 23, 25, 27
magnitude start with 2 increase by 1
when low
value 4.2, 4.1, 4.0, 3.9, 3.8, 3.7, 3.5, 3.3, 3.1, 2.8, 2.6, 2.4, 2.0, 1.6, 1.2
when fall
min 4.2, 4.1, 4.0, 3.9, 3.8, 3.7, 3.5, 3.3, 3.1, 2.8, 2.6, 2.4, 2.0, 1.6, 1.2 qualify
rise on magnitude and max
locate in inflammatory;
—Streams without Severity
define stream AaDO2 as "AaDO2" locate in respiratory;
define stream ABP_Diastolic_NBP as "ABP Diastolic NBP" locate in hematologic;
define stream Alk_Phos as "Alk Phos" locate in metabolic;
define stream ALT_SGPT as "ALT(SGPT)" locate in hepatic;
define stream Amylase as "Amylase" locate in inflammatory;
define stream APTT as "APTT" locate in haemostatic;
define stream Arterial_Base_Excess as "Arterial Base Excess" locate in acidbase;
define stream Arterial_Glucose as "Glucose Art" locate in metabolic;
define stream Arterial_Hematocrit as "Hematocrit Art" locate in hematologic;
define stream Arterial_PaO2 as "Arterial PaO2" locate in respiratory;
define stream Arterial_Potassium as "Potassium Art" locate in electrolytic;
define stream Arterial_Sodium as "Sodium Art" locate in electrolytic;
define stream AST_SGOT as "AST(SGOT)" locate in inflammatory;
define stream Basophils as "Basophils" locate in metabolic;
define stream Bilirubin_Direct as "Bilirubin Direct" locate in hematologic;
define stream Bilirubin_Total as "Bilirubin Total" locate in electrolytic;
define stream BIPAP_IPAP as "BIPAP-IPAP" locate in respiratory;
define stream BIPAP_EPAP as "BIPAP-EPAP" locate in respiratory;
define stream BNP as "BNP" locate in cardiac;
define stream CaO2 as "CaO2" locate in respiratory;
define stream CK_MB as "CK-MB" locate in inflammatory;
define stream CK_Total as "CK Total" locate in renal;
define stream CVP as "CVP" locate in cardiac;
define stream D_Dimer as "D-Dimer" locate in haemostatic;
define stream Eosinophils as "Eosinophils" locate in inflammatory;
define stream Eosinophils_Abs as "Eosinophils Abs" locate in inflammatory;
define stream INR as "INR" locate in haemostatic;
define stream Lactic_Acid as "Lactic Acid" locate in acidbase;
define stream Lipase as "Lipase" locate in inflammatory;
define stream Lymph_Atypical_Abs as "Lymph Atypical Abs" locate in inflammatory;
define stream MCH as "MCH" locate in hematologic;
define stream MCHC as "MCHC" locate in hematologic;
define stream MCV as "MCV" locate in hematologic;
define stream MPV as "MPV" locate in hematologic;
define stream Magnesium as "Magnesium" locate in electrolytic;
define stream Metamyelocytes_Abs as "Metamyelocytes Abs" locate in inflammatory;
define stream Myelocyte_Abs as "Myelocyte Abs" locate in inflammatory;
define stream Monocytes_Abs as "Monocytes Abs" locate in inflammatory;
define stream Myelocyte as "Myelocyte" locate in inflammatory;
define stream O2_Flow as "O2 Flow" locate in respiratory;

define stream Osmolality as "Osmolality" locate in metabolic;
define stream PEEP as "PEEP" locate in respiratory;
define stream Phosphorus as "Phosphorus" locate in electrolytic;
define stream Pressure_Support as "Pressure Support" locate in respiratory;
define stream PT as "PT" locate in haemostatic;
define stream RBC as "RBC" locate in hematologic;
define stream RDW_CV as "RDW-CV" locate in hematologic;
define stream SaO2_Calculated as "SaO2 Calc" locate in respiratory;
define stream Spon_RR_Mech as "Spon RR (Mech.)" locate in respiratory;
define stream Spon_Vt_L_Mech as "Spon. Vt (L) (Mech.)" locate in respiratory;
define stream Total_Protein as "Total Protein" locate in respiratory;
define stream Troponin as "Troponin" locate in respiratory;
define stream Uric_Acid as "Uric Acid" locate in metabolic;
—Temp
Identify TempRiseOrHighMarginal as TemperatureFRiseMarginal or
TemperatureFHighMarginal Locate in inflammatory;
Identify TempRiseOrHighMild as TemperatureFRiseMild or TemperatureFHighMild Locate in inflammatory;
Identify TempRiseOrHighModerate as TemperatureFRiseModerate or TemperatureFHighModerate Locate in inflammatory;
Identify TempRiseOrHighSevere as TemperatureFRiseSevere or TemperatureFHighSevere Locate in inflammatory;
Identify TempRiseOrHighProfound as TemperatureFRiseProfound or TemperatureFHighMild Locate in inflammatory;
Identify TempFallOrLowMarginal as TemperatureFFallMarginal or TemperatureFLowMarginal Locate in inflammatory;
Identify TempFallOrLowMild as TemperatureFFallMild or TemperatureFLowMild Locate in inflammatory;
Identify TempFallOrLowMod as TemperatureFFallModerate or TemperatureFLowModerate Locate in inflammatory;
Identify TempFallOrLowSevere as TemperatureFFallSevere or TemperatureFLowSevere Locate in inflammatory;
Identify TempFallOrLowProfound as TemperatureFFallProfound or TemperatureFLowProfound Locate in inflammatory;
Identify TempBiphasicMarginal as TemperatureFRiseMarginal and TemperatureFFall within 1d Locate in inflammatory;
Identify TempBiphasicMild as TemperatureFRiseMild and TemperatureFFall within 1d Locate in inflammatory;
Identify TempBiphasicMod as TemperatureFRiseModerate and TemperatureFFall within 1d Locate in inflammatory;
Identify TempBiphasicSevere as TemperatureFRiseSevere and TemperatureFFall within 1d Locate in inflammatory;
Identify TempBiphasicProfound as TemperatureFRiseProfound and TemperatureFFall within 1d Locate in inflammatory;
—Band/BandAbs Rise or High
identify BandsRiseOrHighMarginal as BandsRiseMarginal or BandsHighMarginal locate in inflammatory;
identify BandsRiseOrHighMild as BandsRiseMild or BandsHighMild locate in inflammatory;
identify BandsRiseOrHighMod as BandsRiseModerate or BandsHighModerate locate in inflammatory;
identify BandsRiseOrHighSevere as BandsRiseSevere or BandsHighSevere locate in inflammatory;
identify BandsRiseOrHighProfound as BandsRiseProfound or BandsHighProfound locate in inflammatory;
identify BandsAbsRiseOrHighMarginal as BandsAbsRiseMarginal or BandsAbsHighMarginal locate in inflammatory;
identify BandsAbsRiseOrHighMild as BandsAbsRiseMild or BandsAbsHighMild locate in inflammatory;
identify BandsAbsRiseOrHighMod as BandsAbsRiseModerate or BandsAbsHighModerate locate in inflammatory;
identify BandsAbsRiseOrHighSevere as BandsAbsRiseSevere or BandsAbsHighSevere locate in inflammatory;
identify BandsAbsRiseOrHighProfound as BandsAbsRiseProfound or BandsAbsHighProfound locate in inflammatory;
—WBC Rise or Fall
identify WBCRiseOrHighMarginal as WBCRiseMarginal or WBCHighMarginal locate in inflammatory;
identify WBCRiseOrHighMild as WBCRiseMild or WBCHighMild locate in inflammatory;
identify WBCRiseOrHighMod as WBCRiseModerate or WBCHighModerate locate in inflammatory;
identify WBCRiseOrHighSevere as WBCRiseSevere or WBCHighSevere locate in inflammatory;
identify WBCRiseOrHighProfound as WBCRiseProfound or WBCHighProfound locate in inflammatory;
identify WBCLowOrFallMarginal as WBCFallMarginal or WBCLowMarginal locate in inflammatory;
identify WBCLowOrFallMild as WBCFallMild or WBCLowMild locate in inflammatory;
identify WBCLowOrFallMod as WBCFallModerate or WBCLowModerate locate in inflammatory;
identify WBCLowOrFallSevere as WBCFallSevere or WBCLowSevere locate in inflammatory;
identify WBCLowOrFallProfound as WBCFallProfound or WBCLowProfound locate in inflammatory;
—Neutrophils/Neutrophils Rise or High
identify NeutrophilsHighOrRiseMarginal as NeutrophilsRiseMarginal or NeutrophilsHighMarginal locate in inflammatory;
identify NeutrophilsHighOrRiseMild as NeutrophilsRiseMild or NeutrophilsHighMild locate in inflammatory;
identify NeutrophilsHighOrRiseMod as NeutrophilsRiseModerate or NeutrophilsHighModerate locate in inflammatory;
identify NeutrophilsHighOrRiseSevere as NeutrophilsRiseSevere or NeutrophilsHighSevere locate in inflammatory;
identify NeutrophilsHighOrRiseProfound as NeutrophilsRiseProfound or NeutrophilsHighProfound locate in inflammatory;
identify NeutrophilsAbsHighOrRiseMarginal as NeutrophilsAbsRiseMarginal or NeutrophilsAbsHighMarginal locate in inflammatory; identify NeutrophilsAbsHighOrRiseMild as NeutrophilsAbsRiseMild or
NeutrophilsAbsHighMild locate in inflammatory;
identify NeutrophilsAbsHighOrRiseMod as NeutrophilsAbsRiseModerate or NeutrophilsAbsHighModerate locate in inflammatory;
identify NeutrophilsAbsHighOrRiseSevere as NeutrophilsAbsRiseSevere or NeutrophilsAbsHighSevere locate in inflammatory;

identify NeutrophilsAbsHighOrRiseProfound as NeutrophilsAbsRiseProfound or NeutrophilsAbsHighProfound locate in inflammatory;
—Neutrophils/Neutrophils Low or Fall
identify NeutrophilsLowOrFallMarginal as NeutrophilsFallMarginal or NeutrophilsLowMarginal locate in inflammatory;
identify NeutrophilsLowOrFallMild as NeutrophilsFallMild or NeutrophilsLowMild locate in inflammatory;
identify NeutrophilsLowOrFallMod as NeutrophilsFallModerate or NeutrophilsLowModerate locate in inflammatory;
identify NeutrophilsLowOrFallSevere as NeutrophilsFallSevere or NeutrophilsLowSevere locate in inflammatory;
identify NeutrophilsLowOrFallProfound as NeutrophilsFallProfound or NeutrophilsLowProfound locate in inflammatory;
identify NeutrophilsAbsLowOrFallMarginal as NeutrophilsAbsFallMarginal or NeutrophilsAbsLowMarginal locate in inflammatory;
identify NeutrophilsAbsLowOrFallMild as NeutrophilsAbsFallMild or NeutrophilsAbsLowMild locate in inflammatory;
identify NeutrophilsAbsLowOrFallMod as NeutrophilsAbsFallModerate or NeutrophilsAbsLowModerate locate in inflammatory;
identify NeutrophilsAbsLowOrFallSevere as NeutrophilsAbsFallSevere or NeutrophilsAbsLowSevere locate in inflammatory;
identify NeutrophilsAbsLowOrFallProfound as NeutrophilsAbsFallProfound or NeutrophilsAbsLowProfound locate in inflammatory;
—LymphocytesAbs Low or Fall
identify LymphocytesAbsLowOrFallMarginal as LymphocytesAbsFallMarginal or LymphocytesAbsLowMarginal locate in inflammatory;
identify LymphocytesAbsLowOrFallMild as LymphocytesAbsFallMild or LymphocytesAbsLowMild locate in inflammatory;
identify LymphocytesAbsLowOrFallMod as LymphocytesAbsFallModerate or LymphocytesAbsLowModerate locate in inflammatory;
identify LymphocytesAbsLowOrFallSevere as LymphocytesAbsFallSevere or LymphocytesAbsLowSevere locate in inflammatory;
identify LymphocytesAbsLowOrFallProfound as LymphocytesAbsFallProfound or LymphocytesAbsLowProfound locate in inflammatory;
—Pathophysiologically Divergence or Decoherence (PD) of LymphocytesAbs in Relation to Bands Bands Abs indicative of Inflammation, Stress, or Lymphocyte depletion
Identify PDLymphocytesAbsBandsMarginal as BandsRiseorHighMarginal and LymphocytesAbsFallMarginal within 1d Locate in inflammatory;
Identify PDLymphocytesAbsBandsMild as BandsRiseorHighMild and LymphocytesAbsFallMild within 1d Locate in inflammatory;
Identify PDLymphocytesAbsBandsMod as BandsRiseorHighMod and LymphocytesAbsFallModerate within 1d Locate in inflammatory;
Identify PDLymphocytesAbsBandsSevere as BandsRiseorHighSevere and LymphocytesAbsFallSevere within 1d Locate in inflammatory;
Identify PDLymphocytesAbsBandsProfound as BandsRiseorHighProfound and LymphocytesAbsFallProfound within 1d Locate in inflammatory;
identify PDLymphocytesAbsBandsAbsMarginal as BandsAbsRiseorHighMarginal and LymphocytesAbsFallMarginal within 1d Locate in inflammatory;
Identify PDLymphocytesAbsBandsAbsMild as BandsAbsRiseorHighMild and LymphocytesAbsFallMild within 1d Locate in inflammatory;
Identify PDLymphocytesAbsBandsAbsMod as BandsAbsRiseorHighMod and LymphocytesAbsFallModerate within 1d Locate in inflammatory;
Identify PDLymphocytesAbsBandsAbsSevere as BandsAbsRiseorHighSevere and LymphocytesAbsFallSevere within 1d Locate in inflammatory;
Identify PDLymphocytesAbsBandsAbsProfound as BandsAbsRiseorHighProfound and LymphocytesAbsFallProfound within 1d Locate in inflammatory;
—Pathophysiologically Divergence or Decoherence (PD) of LymphocytesAbs in Relation to Neutrophils/NeutrophilsAbs indicative of Inflammation, Stress, or Lymphocyte depletion identify PDLymphocytesAbsNeutrophilsAbsMarginal as NeutrophilsAbsHighorRiseMarginal and LymphocytesAbsFallMarginal within 1d Locate in inflammatory;
Identify PDLymphocytesAbsNeutrophilsAbsMild as NeutrophilsAbsHighorRiseMild and LymphocytesAbsFallMild within 1d Locate in inflammatory;
Identify PDLymphocytesAbsNeutrophilsAbsMod as NeutrophilsAbsHighorRiseMod and LymphocytesAbsFallModerate within 1d Locate in inflammatory;
Identify PDLymphocytesAbsNeutrophilsAbsSevere as NeutrophilsAbsHighorRiseSevere and LymphocytesAbsFallSevere within 1d Locate in inflammatory;
Identify PDLymphocytesAbsNeutrophilsAbsProfound as NeutrophilsAbsHighorRiseProfound and LymphocytesAbsFallProfound within 1d Locate in inflammatory;
identify PDLymphocytesAbsWBCMarginal as WBCRiseorHighMarginal and LymphocytesAbsFallMarginal within 1d Locate in inflammatory;
Identify PDLymphocytesAbsWBCMild as WBCRiseorHighMild and LymphocytesAbsFallMild within 1d Locate in inflammatory;
Identify PDLymphocyteAbssWBCMod as WBCRiseorHighMod and LymphocytesAbsFallModerate within 1d Locate in inflammatory;
Identify PDLymphocytesAbsWBCSevere as WBCRiseorHighSevere and LymphocytesAbsFallSevere within 1d Locate in inflammatory;
Identify PDLymphocytesAbsWBCProfound as WBCRiseorHighProfound and LymphocytesAbsFallProfound within 1d Locate in inflammatory;
—Pathophysiologically Divergence or Decoherence of WBC and Bands(PD) indicative of Neutrophil Failure (in relation to WBC)
Identify PDWBCBandsMarginal as BandsRiseorHighMarginal and WBCLowOrFallMarginal within 1d Locate in inflammatory;
Identify PDWBCBandsMild as BandsRiseorHighMild and WBCLowOrFallMild within 1d Locate in inflammatory;
Identify PDWBCBandsMod as BandsRiseorHighMod and WBCLowOrFallMod within 1d Locate in inflammatory;

Identify PDWBCBandsSevere as BandsRiseorHighSevere and WBCLowOrFallSevere within 1d Locate in inflammatory;
Identify PDWBCBandsProfound as BandsRiseorHighProfound and WBCLowOrFallProfound within 1d Locate in inflammatory;
Identify PDWBCBandsMod2 as BandsRiseorHighMod and WBCRiseOrHighMarginal within 1d Locate in inflammatory;
Identify PDWBCBandsSevere2 as BandsRiseorHighSevere and WBCRiseOrHighMild within 1d Locate in inflammatory;
Identify PDWBCBandsProfound2 as BandsRiseorHighProfound and WBCLowOrFallMod within 1d Locate in inflammatory;
—Pathophysiologically Divergence or Decoherence (PD) of Neutrophils and Bands indicative of Neutrophil Failure (in relation to mature Neutrophils)
Identify PDNeutrophilsBandsMarginal as BandsRiseorHighMarginal and NeutrophilsLowOrFallMarginal within 1d Locate in inflammatory;
Identify PDNeutrophilsBandsMild as BandsRiseorHighMild and NeutrophilsLowOrFallMild within 1d Locate in inflammatory;
Identify PDNeutrophilsBandsMod as BandsRiseorHighMod and NeutrophilsLowOrFallMod within 1d Locate in inflammatory;
Identify PDNeutrophilsBandsSevere as BandsRiseorHighSevere and NeutrophilsLowOrFallSevere within 1d Locate in inflammatory;
Identify PDNeutrophilsBandsProfound as BandsRiseorHighProfound and NeutrophilsLowOrFallProfound within 1d Locate in inflammatory;
Identify PDNeutrophilsBandsMod2 as BandsRiseorHighMod and NeutrophilsLowOrFallMarginal within 1d Locate in inflammatory;
Identify PDNeutrophilsBandsSevere2 as BandsRiseorHighSevere and NeutrophilsLowOrFallMild within 1d Locate in inflammatory;
Identify PDNeutrophilsBandsProfound2 as BandsRiseorHighProfound and NeutrophilsLowOrFallMod within 1d Locate in inflammatory;
Identify PDNeutrophilsAbsBandsMarginal as BandsAbsRiseorHighMarginal and NeutrophilsAbsLowOrFallMarginal within 1d Locate in inflammatory;
Identify PDNeutrophilsAbsBandsMild as BandsAbsRiseorHighMild and NeutrophilsAbsLowOrFallMild within 1d Locate in inflammatory;
Identify PDNeutrophilsAbsBandsMod as BandsAbsRiseorHighMod and NeutrophilsAbsLowOrFallMod within 1d Locate in inflammatory;
Identify PDNeutrophilsAbsBandsSevere as BandsAbsRiseorHighSevere and NeutrophilsAbsLowOrFallSevere within 1d Locate in inflammatory;
Identify PDNeutrophilsAbsBandsProfound as BandsAbsRiseorHighProfound and NeutrophilsAbsLowOrFallProfound within 1d Locate in inflammatory;
Identify PDNeutrophilsAbsBandsMod2 as BandsAbsRiseorHighMod and NeutrophilsAbsLowOrFallMarginal within 1d Locate in inflammatory;
Identify PDNeutrophilsAbsBandsSevere2 as BandsAbsRiseorHighSevere and NeutrophilsAbsLowOrFallMild within 1d Locate in inflammatory;
Identify PDNeutrophilsAbsBandsProfound2 as BandsAbsRiseorHighProfound and NeutrophilsAbsLowOrFallMod within 1d Locate in inflammatory;
—Neutrophil Failure (Combined)
Identify NeutrophilFailureMarginal as PDNeutrophilsBandsMarginal or PDNeutrophilsAbsBandsMarginal or PDWBCBandsMarginal or PDNeutrophilsAbsBandsMod2 or PDNeutrophilsBandsMod2 locate in inflammatory;
Identify NeutrophilFailureMild as PDNeutrophilsBandsMild or PDNeutrophilsAbsBandsMild or PDWBCBandsMild or PDNeutrophilsAbsBandsSevere2 or PDNeutrophilsBandsSevere2 locate in inflammatory;
Identify NeutrophilFailureMod as PDNeutrophilsBandsMod or PDNeutrophilsAbsBandsMod or PDWBCBandsMod or PDNeutrophilsAbsBandsProfound2 or PDNeutrophilsBandsProfound2 locate in inflammatory;
Identify NeutrophilFailureSevere as PDNeutrophilsBandsSevere or PDNeutrophilsAbsBandsSevere or PDWBCBandsSevere locate in inflammatory;
Identify NeutrophilFailureProfound as PDNeutrophilsBandsProfound or PDNeutrophilsAbsBandsProfound or PDWBCBandsProfound locate in inflammatory;
—Bands OR Neutrophil Rise or High
identify NeutrophilOrBandsHighOrRiseMarginal as BandsAbsRiseOrHighMarginal or NeutrophilsAbsHighOrRiseMarginal locate in inflammatory;
identify NeutrophilOrBandsHighOrRiseMild as BandsAbsRiseOrHighMild or NeutrophilsAbsHighOrRiseMild locate in inflammatory;
identify NeutrophilOrBandsHighOrRiseMod as BandsAbsRiseOrHighMild or NeutrophilsAbsHighOrRiseMod locate in inflammatory;
identify NeutrophilOrBandsHighOrRiseSevere as BandsAbsRiseOrHighMild or NeutrophilsAbsHighOrRiseSevere locate in inflammatory;
identify NeutrophilOrBandsHighOrRiseProfound as BandsAbsRiseOrHighMild or NeutrophilsAbsHighOrRiseProfound locate in inflammatory;
—Bands AND Neutrophil Rise or High
identify NeutrophilANDBandsHighOrRiseMarginal as BandsAbsRiseOrHighMarginal and NeutrophilsAbsHighOrRiseMarginal within 1d locate in inflammatory;
identify NeutrophilANDBandsHighOrRiseMild as BandsAbsRiseOrHighMild and NeutrophilsAbsHighOrRiseMild within 1d locate in inflammatory;
identify NeutrophilANDBandsHighOrRiseMod as BandsAbsRiseOrHighMild and NeutrophilsAbsHighOrRiseMod within 1d locate in inflammatory;
identify NeutrophilANDBandsHighOrRiseSevere as BandsAbsRiseOrHighMild and NeutrophilsAbsHighOrRiseSevere within 1d locate in inflammatory;
identify NeutrophilANDBandsHighOrRiseProfound as BandsAbsRiseOrHighMild and NeutrophilsAbsHighOrRiseProfound within 1d locate in inflammatory;
—Temp and Neutrophil and Band Rise or High
identify NeutrophilAndBandAndTempMarginal as TempRiseOrHighMarginal and NeutrophilANDBandsHighOrRiseMarginal within 1d locate in inflammatory;
identify NeutrophilAndBandAndTempMild as TempRiseOrHighMild and NeutrophilANDBandsHighOrRiseMild within 1d locate in inflammatory;
identify NeutrophilAndBandAndTempMod as TempRiseOrHighModerate and NeutrophilANDBandsHighOrRiseMod within 1d locate in inflammatory;

identify NeutrophilAndBandAndTempSevere as TempRiseOrHighSevere and NeutrophilANDBandsHighOrRiseSevere within 1d locate in inflammatory;

identify NeutrophilAndBandAndTempProfound as TempRiseOrHighProfound and NeutrophilANDBandsHighOrRiseProfound within 1d locate in inflammatory;

—Temp or Neutrophil or Band Rise or High identify NeutrophilOrBandOrTempMarginal as TempRiseOrHighMarginal or NeutrophilOrBandsHighOrRiseMarginal locate in inflammatory;

identify NeutrophilOrBandOrTempMild as TempRiseOrHighMild or NeutrophilOrBandsHighOrRiseMild locate in inflammatory;

identify NeutrophilOrBandOrTempMod as TempRiseOrHighModerate or NeutrophilOrBandsHighOrRiseMod locate in inflammatory;

identify NeutrophilOrBandOrTempSevere as TempRiseOrHighSevere or NeutrophilOrBandsHighOrRiseSevere locate in inflammatory;

identify NeutrophilOrBandOrTempProfound as TempRiseOrHighProfound or NeutrophilOrBandsHighOrRiseProfound locate in inflammatory;

—Biomarker Procalcitonin Rise or High identify ProcalcitoninRiseOrHighMarginal as ProcalcitoninRiseMarginal or ProcalcitoninHighMarginal locate in inflammatory;

identify ProcalcitoninRiseOrHighMild as ProcalcitoninRiseMild or ProcalcitoninHighMild locate in inflammatory;

identify ProcalcitoninRiseOrHighMod as ProcalcitoninRiseModerate or ProcalcitoninHighModerate locate in inflammatory;

identify ProcalcitoninRiseOrHighSevere as ProcalcitoninRiseSevere or ProcalcitoninHighSevere locate in inflammatory;

identify ProcalcitoninRiseOrHighProfound as ProcalcitoninRiseProfound or ProcalcitoninHighProfound locate in inflammatory;

—Neutrophil or Band or Temp and Procalcitonin identify NeutrophilOrBandOrTempProcalcitonMarginal as NeutrophilOrBandOrTempMarginal and ProcalcitoninRiseOrHighMarginal within 2d locate in inflammatory;

identify NeutrophilOrBandOrTempProcalcitoninMild as NeutrophilOrBandOrTempMild and ProcalcitoninRiseOrHighMild within 2d locate in inflammatory;

identify NeutrophilOrBandOrTempProcalcitoninMod as NeutrophilOrBandOrTempMod and ProcalcitoninRiseOrHighMod within 2d locate in inflammatory;

identify NeutrophilOrBandOrTempProcalcitoninSevere as NeutrophilOrBandOrTempSevere and ProcalcitoninRiseOrHighSevere within 2d locate in inflammatory;

identify NeutrophilOrBandOrTempProcalcitonProfound as NeutrophilOrBandOrTempProfound and ProcalcitoninRiseOrHighProfound within 2d locate in inflammatory;

identify NeutrophilAndBandAndTempProcalcitonMarginal as NeutrophilAndBandAndTempMarginal and ProcalcitoninRiseOrHighMarginal within 2d locate in inflammatory;

identify NeutrophilAndBandAndTempProcalcitoninMild as NeutrophilAndBandAndTempMild and ProcalcitoninRiseOrHighMild within 2d locate in inflammatory;

identify NeutrophilAndBandAndTempProcalcitoninMod as NeutrophilAndBandAndTempMod and ProcalcitoninRiseOrHighMod within 2d locate in inflammatory;

identify NeutrophilAndBandAndTempProcalcitoninSevere as NeutrophilAndBandAndTempSevere and ProcalcitoninRiseOrHighSevere within 2d locate in inflammatory;

identify NeutrophilAndBandAndTempProcalcitonProfound as NeutrophilAndBandAndTempProfound and ProcalcitoninRiseOrHighProfound within 2d locate in inflammatory;

—Respiratory

Identify SaO2LowOrFallMarginal as OxSatLowMarginal or OxSatFallMarginal Locate in respiratory;

Identify SaO2LowOrFallMild as OxSatLowMild or OxSatFallMild Locate in respiratory; Identify SaO2LowOrFallMod as OxS atLowModerate or OxSatFallModerate Locate in respiratory;

Identify SaO2LowOrFallSevere as OxSatLowSevere or OxSatFallSevere Locate in respiratory;

Identify SaO2LowOrFallProfound as OxS atLowProfound or OxSatFallProfound Locate in respiratory;

Identify RRHighOrRiseMarginal as RespiratoryRateHighMarginal or RespiratoryRateRiseMarginal Locate in respiratory;

Identify RRHighOrRiseMild as RespiratoryRateHighMild or RespiratoryRateRiseMild Locate in respiratory;

Identify RRHighOrRiseMod as RespiratoryRateHighModerate or RespiratoryRateRiseModerate Locate in respiratory;

Identify RRHighOrRiseSevere as RespiratoryRateHighSevere or RespiratoryRateRiseSevere Locate in respiratory;

Identify RRHighOrRiseProfound as RespiratoryRateHighProfound or RespiratoryRateRiseProfound Locate in respiratory;

Identify PDSPO2RRMarginal as RRHighOrRiseMarginal and SaO2LowOrFallMarginal within 1d Locate in respiratory;

Identify PDSPO2RRMild as RRHighOrRiseMild and SaO2LowOrFallMild within 1d Locate in respiratory;

Identify PDSPO2RRMod as RRHighOrRiseMod and SaO2LowOrFallMod within 1d Locate in respiratory;

Identify PDSPO2RRSevere as RRHighOrRiseSevere and SaO2LowOrFallSevere within 1d Locate in respiratory;

Identify PDSPO2RRProfound as RRHighOrRiseProfound and SaO2LowOrFallProfound within 1d Locate in respiratory;

—Acid Base

Identify BicarbFallOrLowMarginal as BicarbFallMarginal or BicarbLowMarginal locate in acidbase;

Identify BicarbFallOrLowMild as BicarbFallMild or BicarbLowMild locate in acidbase;

Identify BicarbFallOrLowMod as BicarbFallModerate or BicarbLowModerate locate in acidbase;

Identify BicarbFallOrLowSevere as BicarbFallSevere or BicarbLowSevere locate in acidbase;

Identify BicarbFallOrLowProfound as BicarbFallProfound or BicarbLowProfound locate in acidbase;

identify Acidosis as AnionGapRise or AnionGapHigh or PHBloodLow locate in acidbase; identify AcidosisMarginal as AnionGapRiseMarginal or AnionGapHighMarginal or PHBloodLowMarginal locate in acidbase;

identify AcidosisMild as AnionGapRiseMild or AnionGapHighMild or PHBloodLowMild locate in acidbase;

identify AcidosisMod as AnionGapRiseModerate or AnionGapHighModerate or PHBloodLowModerate locate in acidbase;

identify AcidosisSevere as AnionGapRiseSevere or AnionGapHighSevere or PHBloodLowSevere locate in acidbase;

identify AcidosisProfound as AnionGapRiseProfound or AnionGapHighProfound or PHBloodLowProfound locate in acidbase;

Identify LactateRiseOrHighMarginal as LactateRiseMarginal or LactateHighMarginal locate in acidbase;
Identify LactateRiseOrHighMild as LactateRiseMild or LactateHighMild locate in acidbase;
Identify LactateRiseOrHighMod as LactateRiseModerate or LactateHighModerate locate in acidbase;
Identify LactateRiseOrHighSevere as LactateRiseSevere or LactateHighSevere locate in acidbase;
Identify LactateRiseOrHighProfound as LactateRiseProfound or LactateHighProfound locate in acidbase;
identify LacticAcidosisMarginal as AcidosisMarginal and LactateHighMarginal within 9h locate in acidbase;
identify LacticAcidosisMild as AcidosisMild and LactateHighMild within 9h locate in acidbase;
identify LacticAcidosisMod as AcidosisMod and LactateHighModerate within 9h locate in acidbase;
identify LacticAcidosisSevere as AcidosisSevere and LactateHighSevere within 9h locate in acidbase;
identify LacticAcidosisProfound as AcidosisProfound and LactateHighProfound within 9h locate in acidbase;
Identify AcidosisOrBicarbFallorLoworLactateMarginal as AcidosisMarginal or
BicarbFallOrLowMarginal or LactateRiseOrHighMarginal or LacticAcidosisMarginal locate in acidbase;
Identify AcidosisOrBicarbFallorLoworLactateMild as AcidosisMild or BicarbFallOrLowMild or LactateRiseOrHighMild or LacticAcidosisMild locate in acidbase;
Identify AcidosisOrBicarbFallorLoworLactateMod as AcidosisMod or BicarbFallOrLowMod or LactateRiseOrHighMod or LacticAcidosisMod locate in acidbase;
Identify AcidosisOrBicarbFallorLoworLactateSevere as AcidosisSevere or BicarbFallOrLowSevere or LactateRiseOrHighSevere or LacticAcidosisSevere locate in acidbase;
Identify AcidosisOrBicarbFallorLoworLactateProfound as AcidosisProfound or BicarbFallOrLowProfound or LactateRiseOrHighProfound or LacticAcidosisProfound locate in acidbase;
—Fall or Low Calcium or Ionized Calcium
Identify FallorLowCalciumMarginal as CalciumFallMarginal or IonCalciumFallMarginal or CalciumLowMarginal or IonCalciumLowMarginal;
Identify FallorLowCalciumMild as CalciumFallMild or IonCalciumFallMild or CalciumLowMild or IonCalciumLowMild;
Identify FallorLowCalciumMod as CalciumFallModerate or IonCalciumFallModerate or CalciumLowModerate or IonCalciumLowMarginal;
Identify FallorLowCalciumSevere as CalciumFallSevere or IonCalciumFallSevere or CalciumLowMarginal or IonCalciumLowMarginal;
Identify FallorLowCalciumProfound as CalciumFallProfound or IonCalciumFallProfound or CalciumLowProfound or IonCalciumLowProfound;
—Haemostatic
identify PlateletLowOrFallMarginal as PlateletsFallMarginal or PlateletsLowMarginal locate in haemostatic;
identify PlateletLowOrFallMild as PlateletsFallMild or PlateletsLowMild locate in haemostatic;
identify PlateletLowOrFallModerate as PlateletsFallModerate or PlateletsLowModerate locate in haemostatic;
identify PlateletLowOrFallSevere as PlateletsFallSevere or PlateletsLowSevere locate in haemostatic;
identify PlateletLowOrFallProfound as PlateletsFallProfound or PlateletsLowProfound locate in haemostatic;
—Pathophysiologic Divergence or Decoherence of Procalcitonin and Low Temp
identify PDProcalcitoninLowTempMarginal as ProcalcitoninRiseOrHighMarginal and TemperatureFLow within 1d locate in acidbase, inflammatory;
identify PDProcalcitoninLowTempMild as ProcalcitoninRiseOrHighMild and TemperatureFLow within 1d locate in acidbase, inflammatory;
identify PDProcalcitoninLowTempMod as ProcalcitoninRiseOrHighMod and TemperatureFLow within 1d locate in acidbase, inflammatory;
identify PDProcalcitoninLowTempSevere as ProcalcitoninRiseOrHighSevere and TemperatureFLow within 1d locate in acidbase, inflammatory;
identify PDProcalcitoninLowTempProfound as ProcalcitoninRiseOrHighProfound and TemperatureFLow within 1d locate in acidbase, inflammatory;
—Pathophysiologic Divergence or Decoherence Inflammation, Temperature
Identify PDNeutrophilOrBandsTempMarginal as NeutrophilOrBandOrTempMarginal and TemperatureFLowMarginal within 1d Locate in inflammatory;
Identify PDNeutrophilOrBandsTempMild as NeutrophilOrBandOrTempMild and TemperatureFLowMild within 1d Locate in inflammatory;
Identify PDNeutrophilOrBandsTempMod as NeutrophilOrBandOrTempMod and TemperatureFLowModerate within 1d Locate in inflammatory;
Identify PDNeutrophilOrBandsTempSevere as NeutrophilOrBandOrTempSevere and TemperatureFLowSevere within 1d Locate in inflammatory;
Identify PDNeutrophilOrBandsTempProfound as NeutrophilOrBandOrTempProfound and TemperatureFLowProfound within 1d Locate in inflammatory;
Identify PDNeutrophilAndBandsTempMarginal as NeutrophilAndBandAndTempMarginal and TemperatureFLowMarginal within 1d Locate in inflammatory;
Identify PDNeutrophilAndBandsTempMild as NeutrophilAndBandAndTempMild and TemperatureFLowMild within 1d Locate in inflammatory;
Identify PDNeutrophilAndBandsTempMod as NeutrophilAndBandAndTempMod and TemperatureFLowModerate within 1d Locate in inflammatory;
Identify PDNeutrophilAndBandsTempSevere as NeutrophilAndBandAndTempSevere and TemperatureFLowSevere within 1d Locate in inflammatory;
Identify PDNeutrophilAndBandsTempProfound as NeutrophilAndBandAndTempProfound and
TemperatureFLowProfound within 1d Locate in inflammatory;
—Inflammatory Augmentation
Identify InflammatoryAugmentationMild as
  NeutrophilOrBandOrTempMild or
    NeutrophilAndBandsHighOrRiseMild or
  PDLymphocytesAbsBandsMild or
    PDLymphocytesAbsNeutrophilsAbsMild or
    NeutrophilOrBandOrTempProcalcitoninMild or
  PDProcalcitoninLowTempMild
  locate in inflammatory;
Identify InflammatoryAugmentationMod as
  NeutrophilOrBandOrTempMod or
    NeutrophilAndBandsHighOrRiseMod or
  PDLymphocytesAbsBandsMod or
    PDLymphocytesAbsNeutrophilsAbsMod or
    NeutrophilOrBandOrTempProcalcitoninMod or PDProcalcitoninLowTempMod or
PDNeutrophilOrBandsTempMarginal or
PDNeutrophilAndBandsTempMarginal or
PDNeutrophilOrBandsTempMild or
PDNeutrophilAndBandsTempMild or
PDNeutrophilOrBandsTempMod or
PDNeutrophilAndBandsTempMod or
NeutrophilFailureMarginal or
NeutrophilFailureMild or
NeutrophilFailureMod
   locate in inflammatory;
Identify InflammatoryAugmentationMarginal as
   NeutrophilOrBandOrTempMarginal or
   NeutrophilAndBandsHighOrRiseMarginal or
   PDLymphocytesAbsBandsMarginal or
   PDLymphocytesAbsNeutrophilsAbsMarginal or
   NeutrophilOrBandOrTempProcalcitonMarginal or
   PDProcalcitoninLowTempMarginal
   Locate in inflammatory;
Identify InflammatoryAugmentationSevere as
   NeutrophilOrBandOrTempSevere or
   NeutrophilAndBandsHighOrRiseSevere or
   PDLymphocytesAbsBandsSevere or
   PDLymphocytesAbsNeutrophilsAbsSevere or
   NeutrophilOrBandOrTempProcalcitoninSevere or
   PDProcalcitoninLowTempSevere or
   PDNeutrophilOrBandsTempSevere or
   PDNeutrophilAndBandsTempSevere or
   NeutrophilFailureSevere
   locate in inflammatory;
Identify InflammatoryAugmentationProfound as
   NeutrophilOrBandOrTempProfound or
   NeutrophilAndBandsHighOrRiseProfound or
   PDLymphocytesAbsBandsProfound or
   PDLymphocytesAbsNeutrophilsAbsProfound or
   NeutrophilOrBandOrTempProcalcitonProfound or
   PDProcalcitoninLowTempMarginal or
   PDNeutrophilOrBandsTempProfound or
   PDNeutrophilAndBandsTempProfound or
   NeutrophilFailureProfound
   locate in inflammatory;
—Inflammation and Haemostatic
identify SeqInflammatoryAugmentationPlateletFallMild as InflammatoryAugmentationMild preceding PlateletsFallMild within 1d locate in inflammatory, haemostatic;
identify SeqInflammatoryAugmentationPlateletFallMod as InflammatoryAugmentationMod preceding PlateletsFallModerate within 1d locate in inflammatory, haemostatic;
identify SeqInflammatoryAugmentationPlateletFallSevere as InflammatoryAugmentationSevere preceding PlateletsFallSevere within 1d locate in inflammatory, haemostatic;
identify SeqInflammatoryAugmentationPlateletFallProfound as InflammatoryAugmentationProfound preceding PlateletsFallProfound within 1d locate in inflammatory, haemostatic;
identify InflammatoryAugmentationPlateletLowOrFallMarginal as InflammatoryAugmentationMarginal and PlateletsFallMarginal within 1d locate in inflammatory, haemostatic;
identify InflammatoryAugmentationPlateletLowOrFallMild as InflammatoryAugmentationMild and PlateletsFallMild within 1d locate in inflammatory, haemostatic;
identify InflammatoryAugmentationPlateletLowOrFallMod as InflammatoryAugmentationMod and PlateletsFallModerate within 1d locate in inflammatory, haemostatic;
identify InflammatoryAugmentationPlateletLowOrFallSevere as InflammatoryAugmentationSevere and PlateletsFallSevere within 1d locate in inflammatory, haemostatic;
identify InflammatoryAugmentationPlateletLowOrFallProfound as InflammatoryAugmentationProfound and PlateletsFallProfound within 1d locate in inflammatory, haemostatic;
—Inflammation and Acid Base
identify SeqInflammationAndAcidosisMarginal as InflammatoryAugmentationMarginal preceding AcidosisMarginal within 1d locate in inflammatory, acidbase;
identify SeqInflammationAndAcidosisMild as InflammatoryAugmentationMild preceding AcidosisMild within 1d locate in inflammatory, acidbase;
identify SeqInflammationAndAcidosisModerate as InflammatoryAugmentationMod preceding AcidosisMod within 1d locate in inflammatory, acidbase;
identify SeqInflammationAndAcidosisSevere as InflammatoryAugmentationSevere preceding AcidosisSevere within 1d locate in inflammatory, acidbase;
identify SeqInflammationAndAcidosisProfound as InflammatoryAugmentationProfound preceding AcidosisProfound within 1d locate in inflammatory, acidbase;
identify InflammationAndAcidosisMarginal as InflammatoryAugmentationMarginal and AcidosisMarginal within 1d locate in inflammatory, acidbase;
identify InflammationAndAcidosisMild as InflammatoryAugmentationMild and AcidosisMild within 1d locate in inflammatory, acidbase;
identify InflammationAndAcidosisMod as InflammatoryAugmentationMod and AcidosisMod within 1d locate in inflammatory, acidbase;
identify InflammationAndAcidosisSevere as InflammatoryAugmentationSevere and AcidosisSevere within 1d locate in inflammatory, acidbase;
identify InflammationAndAcidosisProfound as InflammatoryAugmentationProfound and AcidosisProfound within 1d locate in inflammatory, acidbase;
—Inflammation and Metabolic
Identify InflammationAndAlbuminFallMarginal as InflammatoryAugmentationMarginal and AlbuminFallMarginal within 2d locate in inflammatory, metabolic;
Identify InflammationAndAlbuminFallMild as InflammatoryAugmentationMild and AlbuminFallMild within 2d locate in inflammatory, metabolic;
Identify InflammationAndAlbuminFallMod as InflammatoryAugmentationMod and AlbuminFallModerate within 2d locate in inflammatory, metabolic;
Identify InflammationAndAlbuminFallSevere as InflammatoryAugmentationSevere and AlbuminFallSevere within 2d locate in inflammatory, metabolic;
Identify InflammationAndAlbuminFallProfound as InflammatoryAugmentationProfound and AlbuminFallProfound within 2d locate in inflammatory, metabolic;
Identify SeqInflammationAndAlbuminFallMarginal as InflammatoryAugmentationMarginal preceding AlbuminFallMarginal within 2d locate in inflammatory, metabolic;
Identify SeqInflammationAndAlbuminFallMild as InflammatoryAugmentationMild preceding AlbuminFallMild within 2d locate in inflammatory, metabolic;
Identify SeqInflammationAndAlbuminFallMod as InflammatoryAugmentationMod preceding AlbuminFallModerate within 2d locate in inflammatory, metabolic;
Identify SeqInflammationAndAlbuminFallSevere as InflammatoryAugmentationSevere preceding AlbuminFallSevere within 2d locate in inflammatory, metabolic;

Identify SeqInflammationAndAlbuminFallProfound as InflammatoryAugmentationProfound preceding AlbuminFallProfound within 2d locate in inflammatory, metabolic;

—Haemostatic and Procalcitonin identify SeqProcalcitoninPlateletFallMarginal as ProcalcitoninRiseOrHighMarginal preceding PlateletsFallMarginal within 1d locate in inflammatory, haemostatic;

identify SeqInflammationPlateletFallMild as ProcalcitoninRiseOrHighMild preceding PlateletsFallMild within 1d locate in inflammatory, haemostatic;

identify SeqProcalcitoninPlateletFallMod as ProcalcitoninRiseOrHighMod preceding PlateletsFallModerate within 1d locate in inflammatory, haemostatic;

identify SeqProcalcitoninPlateletFallSevere as ProcalcitoninRiseOrHighSevere preceding PlateletsFallSevere within 1d locate in inflammatory, haemostatic;

identify SeqProcalcitoninPlateletFallProfound as ProcalcitoninRiseOrHighProfound preceding PlateletsFallProfound within 1d locate in inflammatory, haemostatic;

identify ProcalcitoninPlateletLowOrFallMarginal as ProcalcitoninRiseOrHighMarginal and PlateletsFallMarginal within 1d locate in inflammatory, haemostatic;

identify ProcalcitoninPlateletLowOrFallMild as ProcalcitoninRiseOrHighMild and PlateletsFallMild within 1d locate in inflammatory, haemostatic;

identify ProcalcitoninPlateletLowOrFallMod as ProcalcitoninRiseOrHighMod and PlateletsFallModerate within 1d locate in inflammatory, haemostatic;

identify ProcalcitoninPlateletLowOrFallSevere as ProcalcitoninRiseOrHighSevere and PlateletsFallSevere within 1d locate in inflammatory, haemostatic;

identify ProcalcitoninPlateletLowOrFallProfound as ProcalcitoninRiseOrHighProfound and PlateletsFallProfound within 1d locate in inflammatory, haemostatic;

—Acid Base and Procalcitonin identify SeqProcalcitoninAcidosisMarginal as ProcalcitoninRiseOrHighMarginal preceding AcidosisMarginal within 1d locate in acidbase, inflammatory;

identify SeqProcalcitoninAcidosisMild as ProcalcitoninRiseOrHighMild preceding AcidosisMarginal within 1d locate in acidbase, inflammatory;

identify SeqProcalcitoninAcidosisMod as ProcalcitoninRiseOrHighMod preceding AcidosisMod within 1d locate in acidbase, inflammatory;

identify SeqProcalcitoninAcidosisSevere as ProcalcitoninRiseOrHighSevere preceding AcidosisSevere within 1d locate in acidbase, inflammatory;

identify SeqProcalcitoninAcidosisProfound as ProcalcitoninRiseOrHighProfound preceding AcidosisProfound within 1d locate in acidbase, inflammatory;

identify ProcalcitoninAcidosisMarginal as ProcalcitoninRiseOrHighMarginal and AcidosisMarginal within 1d locate in acidbase, inflammatory;

identify ProcalcitoninAcidosisMild as ProcalcitoninRiseOrHighMild and AcidosisMild within 1d locate in acidbase, inflammatory;

identify ProcalcitoninAcidosisMod as ProcalcitoninRiseOrHighMod and AcidosisMod within 1d locate in acidbase, inflammatory;

identify ProcalcitoninAcidosisSevere as ProcalcitoninRiseOrHighSevere and AcidosisSevere within 1d locate in acidbase, inflammatory;

identify ProcalcitoninAcidosisProfound as ProcalcitoninRiseOrHighProfound and AcidosisProfound within 1d locate in acidbase, inflammatory;

identify SeqProcalcitoninLactateMarginal as ProcalcitoninRiseOrHighMarginal preceding LactateRiseOrHighMarginal within 1d locate in acidbase, inflammatory;

identify SeqProcalcitoninLactateMild as ProcalcitoninRiseOrHighMild preceding LactateRiseOrHighMarginal within 1d locate in acidbase, inflammatory;

identify SeqProcalcitoninLactateMod as ProcalcitoninRiseOrHighMod preceding LactateRiseOrHighMod within 1d locate in acidbase, inflammatory;

identify SeqProcalcitoninLactateSevere as ProcalcitoninRiseOrHighSevere preceding LactateRiseOrHighSevere within 1d locate in acidbase, inflammatory;

identify SeqProcalcitoninLactateProfound as ProcalcitoninRiseOrHighProfound preceding LactateRiseOrHighProfound within 1d locate in acidbase, inflammatory;

identify ProcalcitoninLactateMarginal as ProcalcitoninRiseOrHighMarginal and LactateRiseOrHighMarginal within 1d locate in acidbase, inflammatory;

identify ProcalcitoninLactateMild as ProcalcitoninRiseOrHighMild and LactateRiseOrHighMild within 1d locate in acidbase, inflammatory;

identify ProcalcitoninLactateMod as ProcalcitoninRiseOrHighMod and LactateRiseOrHighMod within 1d locate in acidbase, inflammatory;

identify ProcalcitoninLactateSevere as ProcalcitoninRiseOrHighSevere and LactateRiseOrHighSevere within 1d locate in acidbase, inflammatory;

identify ProcalcitoninLactateProfound as ProcalcitoninRiseOrHighProfound and LactateRiseOrHighProfound within 1d locate in acidbase, inflammatory;

identify ProcalcitoninBicarbFallMarginal as ProcalcitoninRiseOrHighMarginal and BicarbFallMarginal within 1d locate in acidbase, inflammatory;

identify ProcalcitoninBicarbFallMild as ProcalcitoninRiseOrHighMild and BicarbFallMild within 1d locate in acidbase, inflammatory;

identify ProcalcitoninBicarbFallMod as ProcalcitoninRiseOrHighMod and BicarbFallModerate within 1d locate in acidbase, inflammatory;

identify ProcalcitoninBicarbFallSevere as ProcalcitoninRiseOrHighSevere and BicarbFallSevere within 1d locate in acidbase, inflammatory;

identify ProcalcitoninBicarbFallProfound as ProcalcitoninRiseOrHighProfound and BicarbFallProfound within 1d locate in acidbase, inflammatory;

identify SeqProcalcitoninBicarbFallMarginal as ProcalcitoninRiseOrHighMarginal preceding BicarbFallMarginal within 1d locate in acidbase, inflammatory;

identify SeqProcalcitoninFallOrLowBicarbMild as ProcalcitoninRiseOrHighMild preceding BicarbFallMild within 1d locate in acidbase, inflammatory;

identify SeqProcalcitoninBicarbFallMod as ProcalcitoninRiseOrHighMod preceding BicarbFallModerate within 1d locate in acidbase, inflammatory;

identify SeqProcalcitoninBicarbFallSevere as ProcalcitoninRiseOrHighSevere preceding BicarbFallSevere within 1d locate in acidbase, inflammatory;

identify SeqProcalcitoninBicarbFallProfound as ProcalcitoninRiseOrHighProfound preceding BicarbFallProfound within 1d locate in acidbase, inflammatory;

identify ProcalcitoninFallOrLowBicarbMarginal as ProcalcitoninRiseOrHighMarginal and BicarbFallOrLowMarginal within 1d locate in acidbase, inflammatory;

identify ProcalcitoninFallOrLowBicarbMild as ProcalcitoninRiseOrHighMild and BicarbFallOrLowMild within 1d locate in acidbase, inflammatory;

identify ProcalcitoninFallOrLowBicarbMod as ProcalcitoninRiseOrHighMod and BicarbFallOrLowMod within 1d locate in acidbase, inflammatory;
identify ProcalcitoninFallOrLowBicarbSevere as ProcalcitoninRiseOrHighSevere and BicarbFallOrLowSevere within 1d locate in acidbase, inflammatory;
identify ProcalcitoninFallOrLowBicarbProfound as ProcalcitoninRiseOrHighProfound and BicarbFallOrLowProfound within 1d locate in acidbase, inflammatory;
—Cardiac
Identify HRHighOrRiseMarginal as HRHighMarginal or HRRiseMarginal Locate in cardiac;
Identify HRHighOrRiseMild as HRHighMild or HRRiseMild Locate in cardiac;
Identify HRHighOrRiseMod as HRHighModerate or HRRiseModerate Locate in cardiac;
Identify HRHighOrRiseSevere as HRHighSevere or HRRiseSevere Locate in cardiac;
Identify HRHighOrRiseProfound as HRHighProfound or HRRiseProfound Locate in cardiac;
Identify BpSystolicLowOrFallMarginal as BpSystolicLowMarginal or BpSystolicFallMarginal Locate in Cardiac;
Identify BpSystolicLowOrFallMild as BpSystolicLowMild or BpSystolicFallMild Locate in Cardiac;
Identify BpSystolicLowOrFallMod as BpSystolicLowModerate or BpSystolicFallModerate Locate in Cardiac;
Identify BpSystolicLowOrFallSevere as BpSystolicLowSevere or BpSystolicFallSevere Locate in Cardiac;
Identify BpSystolicLowOrFallProfound as BpSystolicLowProfound or BpSystolicFallProfound Locate in Cardiac;
Identify PDHRandBpSystolicMarginal as HRHighOrRiseMarginal and BpSystolicLowOrFallMarginal within 1d Locate in cardiac;
Identify PDHRandBpSystolicMild as HRHighOrRiseMild and BpSystolicLowOrFallMild within 1d Locate in cardiac;
Identify PDHRandBpSystolicMod as HRHighOrRiseMod and BpSystolicLowOrFallMod within 1d Locate in cardiac;
Identify PDHRandBpSystolicSevere as HRHighOrRiseSevere and BpSystolicLowOrFallSevere within 1d Locate in cardiac;
Identify PDHRandBpSystolicProfound as HRHighOrRiseProfound and BpSystolicLowOrFallProfound within 1d Locate in cardiac;
—Cardiac/Respiratory
Identify SPO2HRMild as HRHighOrRiseMarginal and SaO2LowOrFallMarginal within 1d Locate in respiratory;
Identify SPO2HRMild_duplicated as HRHighOrRiseMild and SaO2LowOrFallMild within 1d Locate in respiratory;
Identify SPO2HRMod as HRHighOrRiseMod and SaO2LowOrFallMod within 1d Locate in respiratory;
Identify SPO2HRSevere as HRHighOrRiseSevere and SaO2LowOrFallSevere within 1d Locate in respiratory;
Identify SPO2HRProfound as HRHighOrRiseProfound and SaO2LowOrFallProfound within 1d Locate in respiratory;
—Temp/Cardiac/Respiratory/Inflammation CONY Convergence or Coherence
Identify CONVHighHRRRMarginal as HRHighMarginal and RespiratoryRateHighMarginal within 1d Locate in respiratory, cardiac;
Identify CONVHighHRRRMild as HRHighMild and RespiratoryRateHighMild within 1d Locate in respiratory, cardiac;
Identify CONVHighHRRRMod as HRHighModerate and RespiratoryRateHighModerate within 1d Locate in respiratory, cardiac;
Identify CONVHighHRRRSevere as HRHighSevere and RespiratoryRateHighSevere within 1d Locate in respiratory, cardiac;
Identify CONVHighHRRRProfound as HRHighProfound and RespiratoryRateHighProfound within 1d Locate in respiratory, cardiac;
Identify CONVHighHRtempRRMarginal as CONVHighHRRRMarginal and TemperatureFHighMarginal within 1d Locate in respiratory, cardiac, inflammatory;
Identify CONVHighHRtempRRMild as CONVHighHRRRMild and TemperatureFHighMild within 1d Locate in respiratory, cardiac, inflammatory;
Identify CONVHighHRtempRRMod as CONVHighHRRRMod and TemperatureFHighModerate and RespiratoryRateHighModerate within 1d Locate in respiratory, cardiac, inflammatory;
Identify CONVHighHRtempRRSevere as CONVHighHRRRSevere and TemperatureFHighSevere and RespiratoryRateHighSevere within 1d Locate in respiratory, cardiac, inflammatory;
Identify CONVHighHRtempRRProfound as CONVHighHRRRProfound and TemperatureFHighProfound and RespiratoryRateHighProfound within 1d Locate in respiratory, cardiac, inflammatory;
Identify CONVHighHRtempRRInflammationMarginal as CONVHighHRtempRRMarginal and InflammatoryAugmentationMarginal within 1d Locate in respiratory, cardiac, inflammatory;
Identify CONVHighHRtempRRInflammationMild as CONVHighHRtempRRMild and InflammatoryAugmentationMild within 1d Locate in respiratory, cardiac, inflammatory;
Identify CONVHighHRtempRRInflammationMod as CONVHighHRtempRRMod and InflammatoryAugmentationMod within 1d Locate in respiratory, cardiac, inflammatory;
Identify CONVHighHRtempRRInflammationSevere as CONVHighHRtempRRSevere and InflammatoryAugmentationSevere within 1d Locate in respiratory, cardiac, inflammatory;
Identify CONVHighHRtempRRInflammationProfound as CONVHighHRtempRRProfound and InflammatoryAugmentationProfound within 1d Locate in respiratory, cardiac, inflammatory;
Identify CONVHighHRtempRRInflammationCumMarginal as CONVHighHRtempRRMarginal and NeutrophilAndBandAndTempMarginal within 1d Locate in respiratory, cardiac, inflammatory;
Identify CONVHighHRtempRRInflammationCumMild as CONVHighHRtempRRMild and NeutrophilAndBandAndTempMild within 1d Locate in respiratory, cardiac, inflammatory;
Identify CONVHighHRtempRRInflammationCumMod as CONVHighHRtempRRMod and NeutrophilAndBandAndTempMod within 1d Locate in respiratory, cardiac, inflammatory;
Identify CONVHighHRtempRRInflammationCumSevere as CONVHighHRtempRRSevere and NeutrophilAndBandAndTempSevere within 1d Locate in respiratory, cardiac, inflammatory;

Identify CONVHighHRtempRRInflammationCumProfound as CONVHighHRtempRRProfound and NeutrophilAndBandAndTempProfound within 1d Locate in respiratory, cardiac, inflammatory;
Identify PDHHighHRRRBpLowOrFallSystolicMarginal as CONVHighHRRRMarginal and BpSystolicLowOrFallMarginal within 1d Locate in respiratory, cardiac;
Identify PDHHighHRRRBpLowOrFallSystolicMild as CONVHighHRRRMild and BpSystolicLowOrFallMild within 1d Locate in respiratory, cardiac;
Identify PDHHighHRRRBpLowOrFallSystolicModerate as CONVHighHRRRMod and BpSystolicLowOrFallMod within 1d Locate in respiratory, cardiac;
Identify PDHHighHRRRBpLowOrFallSystolicSevere as CONVHighHRRRSevere and BpSystolicLowOrFallSevere within 1d Locate in respiratory, cardiac;
Identify PDHHighHRRRBpLowOrFallSystolicProfound as CONVHighHRRRProfound and BpSystolicLowOrFallProfound within 1d Locate in respiratory, cardiac;
Identify PDHighHRtempRRInflammationlowBPMarginal as CONVHighHRtempRRInflammationMarginal and BpSystolicLowOrFallMarginal within 1d Locate in respiratory, cardiac, inflammatory; Identify PDHighHRtempRRInflammationlowBPMild as CONVHighHRtempRRInflammationMild and BpSystolicLowOrFallMild within 1d Locate in
respiratory, cardiac, inflammatory;
Identify PDHighHRtempRRInflammationlowBPMod as CONVHighHRtempRRInflammationMod and BpSystolicLowOrFallMod within 1d Locate in respiratory, cardiac, inflammatory;
Identify PDHighHRtempRRInflammationlowBPSevere as CONVHighHRtempRRInflammationSevere and BpSystolicLowOrFallSevere within 1d Locate in respiratory, cardiac, inflammatory;
Identify PDHighHRtempRRInflammationlowBPProfound as CONVHighHRtempRRInflammationProfound and BpSystolicLowOrFallProfound within 1d Locate in respiratory, cardiac, inflammatory;
—Pathophysiologic Divergence or Decoherence of Acidosis, SPO2
Identify PDAcidosisSaO2Marginal as AcidosisMarginal and SaO2LowOrFallMarginal within 1d Locate in respiratory, acidbase;
Identify PDAcidosisSaO2Mild as AcidosisMild and SaO2LowOrFallMild within 1d Locate in respiratory, acidbase; Identify PDAcidosisSaO2Mod as AcidosisMod and SaO2LowOrFallMod within 1d Locate in
respiratory, acidbase;
Identify PDAcidosisSaO2Severe as AcidosisSevere and SaO2LowOrFallSevere within 1d Locate in respiratory, acidbase;
Identify PDAcidosisSaO2Profound as AcidosisProfound and SaO2LowOrFallProfound within 1d Locate in respiratory, acidbase;
Identify PDLactateSaO2Marginal as LactateRiseOrHighMarginal and SaO2LowOrFallMarginal within 1d Locate in respiratory, acidbase;
Identify PDLactateSaO2Mild as LactateRiseOrHighMild and SaO2LowOrFallMild within 1d Locate in respiratory, acidbase;
Identify PDLactateSaO2Mod as LactateRiseOrHighMod and SaO2LowOrFallMod within 1d Locate in respiratory, acidbase;
Identify PDLactateSaO2Severe as LactateRiseOrHighSevere and SaO2LowOrFallSevere within 1d Locate in respiratory, acidbase;
Identify PDLactateSaO2Profound as LactateRiseOrHighProfound and SaO2LowOrFallProfound within 1d Locate in respiratory, acidbase;
Identify CONVAcidosisRRMarginal as AcidosisMarginal and RespiratoryRateHighMarginal within 1d Locate in respiratory, cardiac;
Identify CONVAcidosisRRMild as AcidosisMild and RespiratoryRateHighMild within 1d Locate in respiratory, cardiac;
Identify CONVAcidosisRRMod as AcidosisMod and RespiratoryRateHighModerate within 1d Locate in respiratory, cardiac;
Identify CONVAcidosisRRSevere as AcidosisSevere and RespiratoryRateHighSevere within 1d Locate in respiratory, cardiac;
Identify CONVAcidosisRRProfound as AcidosisProfound and RespiratoryRateHighProfound within 1d Locate in respiratory, cardiac;
Identify PDAcidosisOrLactateSaO2Marginal as PDAcidosisSaO2Marginal or PDLactateSaO2Marginal locate in respiratory, acidbase;
Identify PDAcidosisOrLactateSaO2Mild as PDAcidosisSaO2Mild or PDLactateSaO2Mild locate in respiratory, acidbase;
Identify PDAcidosisOrLactateSaO2Mod as PDAcidosisSaO2Mod or PDLactateSaO2Mod locate in respiratory, acidbase;
Identify PDAcidosisOrLactateSaO2Severe as PDAcidosisSaO2Severe or PDLactateSaO2Severe locate in respiratory, acidbase;
Identify PDAcidosisOrLactateSaO2Profound as PDAcidosisSaO2Profound or PDLactateSaO2Profound locate in respiratory, acidbase;
—Pathophysiologic Divergence or Decoherence of Acidosis, BP
Identify PDAcidosisLowOrFallBP as AcidosisMarginal and BpSystolicLowOrFallMarginal within 1d Locate in acidbase, cardiac;
Identify PDAcidosisLowOrFallBP_Duplicated as AcidosisMild and BpSystolicLowOrFallMild within 1d Locate in acidbase, cardiac;
Identify PDAcidosisLowOrFallBP_Duplicated2 as AcidosisMod and BpSystolicLowOrFallMod within 1d Locate in acidbase, cardiac;
Identify PDAcidosisLowOrFallBP_Duplicated3 as AcidosisSevere and BpSystolicLowOrFallSevere within 1d Locate in acidbase, cardiac;
Identify PDAcidosisLowOrFallBP_Duplicated4 as AcidosisProfound and BpSystolicLowOrFallProfound within 1d Locate in acidbase, cardiac;
Identify PDAcidosisSPO2InflammationMarginal as PDAcidosisSaO2Marginal and InflammatoryAugmentationMarginal within 1d Locate in acidbase, respiratory, inflammatory;
Identify PDAcidosisSPO2InflammationMild as PDAcidosisSaO2Mild and InflammatoryAugmentationMild within 1d Locate in acidbase, respiratory, inflammatory;
Identify PDAcidosisSPO2InflammationMod as PDAcidosisSaO2Mod and InflammatoryAugmentationMod within 1d Locate in acidbase, respiratory, inflammatory;
Identify PDAcidosisSPO2InflammationSevere as PDAcidosisSaO2Severe and InflammatoryAugmentationSevere within 1d Locate in acidbase, respiratory, inflammatory;

Identify PDAcidosisSPO2InflammationProfound as PDAcidosisSaO2Profound and InflammatoryAugmentationProfound within 1d Locate in acidbase, respiratory, inflammatory;
Identify PDAcidosisSPO2InflammationCumMarginal as PDAcidosisSaO2Marginal and NeutrophilAndBandAndTempMarginal within 1d Locate in acidbase, respiratory, inflammatory;
Identify PDAcidosisSPO2InflammationCumMild as PDAcidosisSaO2Mild and NeutrophilAndBandAndTempMild within 1d Locate in acidbase, respiratory, inflammatory;
Identify PDAcidosisSPO2InflammationCumMod as PDAcidosisSaO2Mod and NeutrophilAndBandAndTempMod within 1d Locate in acidbase, respiratory, inflammatory;
Identify PDAcidosisSPO2InflammationCumSevere as PDAcidosisSaO2Severe and NeutrophilAndBandAndTempSevere within 1d Locate in acidbase, respiratory, inflammatory;
Identify PDAcidosisSPO2InflammationCumProfound as PDAcidosisSaO2Profound and NeutrophilAndBandAndTempProfound within 1d Locate in acidbase, respiratory, inflammatory;
Identify PDLactateSPO2InflammationMarginal as PDLactateSaO2Marginal and InflammatoryAugmentationMarginal within 1d Locate in acidbase, respiratory, inflammatory;
Identify PDLactateSPO2InflammationMild as PDLactateSaO2Mild and InflammatoryAugmentationMild within 1d Locate in acidbase, respiratory, inflammatory;
Identify PDLactateSPO2InflammationMod as PDLactateSaO2Mod and InflammatoryAugmentationMod within 1d Locate in acidbase, respiratory, inflammatory;
Identify PDLactateSPO2InflammationSevere as PDLactateSaO2Severe and InflammatoryAugmentationSevere within 1d Locate in acidbase, respiratory, inflammatory;
Identify PDLactateSPO2InflammationProfound as PDLactateSaO2Profound and InflammatoryAugmentationProfound within 1d Locate in acidbase, respiratory, inflammatory;
Identify PDLactateSPO2InflammationCumMarginal as PDLactateSaO2Marginal and NeutrophilAndBandAndTempMarginal within 1d Locate in acidbase, respiratory, inflammatory;
Identify PDLactateSPO2InflammationCumMild as PDLactateSaO2Mild and NeutrophilAndBandAndTempMild within 1d Locate in acidbase, respiratory, inflammatory;
Identify PDLactateSPO2InflammationCumMod as PDLactateSaO2Mod and NeutrophilAndBandAndTempMod within 1d Locate in acidbase, respiratory, inflammatory;
Identify PDLactateSPO2InflammationCumSevere as PDLactateSaO2Severe and NeutrophilAndBandAndTempSevere within 1d Locate in acidbase, respiratory, inflammatory;
Identify PDLactateSPO2InflammationCumProfound as PDLactateSaO2Profound and NeutrophilAndBandAndTempProfound within 1d Locate in acidbase, respiratory, inflammatory;
Identify HRHighorRRHighMarginal as HRHighMarginal or RespiratoryRateHighMarginal Locate in respiratory, cardiac;
Identify HRHighorRRHighMild as HRHighMild or RespiratoryRateHighMild Locate in respiratory, cardiac;
Identify HRHighorRRHighMod as HRHighModerate or RespiratoryRateHighModerate Locate in respiratory, cardiac;
Identify HRHighorRRHighSevere as HRHighSevere or RespiratoryRateHighSevere Locate in respiratory, cardiac;
Identify HRHighorRRHighProfound as HRHighProfound or RespiratoryRateHighProfound Locate in respiratory, cardiac;
—Renal Failure
identify CreatinineRiseOrHighMarginal as CreatinineRiseMarginal or CreatinineHighMarginal locate in renal;
identify CreatinineRiseOrHighMild as CreatinineRiseMild or CreatinineHighMild locate in renal;
identify CreatinineRiseOrHighMod as CreatinineRiseModerate or CreatinineHighModerate locate in renal;
identify CreatinineRiseOrHighSevere as CreatinineRiseSevere or CreatinineHighSevere locate in renal;
identify CreatinineRiseOrHighProfound as CreatinineRiseProfound or CreatinineHighProfound locate in renal;
—SIRS
Identify SIRSMarginal as InflammatoryAugmentationMarginal and HRHighorRRHighMarginal within 1d locate in inflammatory;
Identify SIRSMild as InflammatoryAugmentationMild and HRHighorRRHighMild within 1d locate in inflammatory;
Identify SIRSMod as InflammatoryAugmentationMod and HRHighorRRHighMod within 1d locate in inflammatory;
Identify SIRSSevere as InflammatoryAugmentationSevere and HRHighorRRHighSevere within 1d locate in inflammatory;
Identify SIRSProfound as InflammatoryAugmentationProfound and HRHighorRRHighProfound within 1d locate in inflammatory;
—InflammatoryAugmentation and Increase or High Acid
Identify InflammatoryAugmentationandAcidMarginal as InflammatoryAugmentationMarginal and AcidosisOrBicarbFallorLoworLactateMarginal within 1d locate in inflammatory, acidbase;
Identify InflammatoryAugmentationandAcidMild as SIRSMild and InflammatoryAugmentationMild within 1d locate in inflammatory, acidbase;
Identify InflammatoryAugmentationandAcidMod as SIRSMod and InflammatoryAugmentationMod within 1d locate in inflammatory, acidbase;
Identify InflammatoryAugmentationandAcidSevere as SIRSSevere and InflammatoryAugmentationSevere within 1d locate in inflammatory, acidbase;
Identify InflammatoryAugmentationandAcidProfound as SIRSProfound and InflammatoryAugmentationProfound within 1d locate in inflammatory, acidbase;
—InflammatoryAugmentation and Low or Fall Platelets
Identify InflammatoryAugmentationandPlateletsLoworFallMarginal as InflammatoryAugmentationMarginal and PlateletLowOrFallMarginal within 1d locate in inflammatory, acidbase;
Identify InflammatoryAugmentationandPlateletsLoworFallMild as InflammatoryAugmentationMild and PlateletLowOrFallMild within 1d locate in inflammatory, acidbase;
Identify InflammatoryAugmentationandPlateletsLoworFallMod as InflammatoryAugmentationMod and PlateletLowOrFallModerate within 1d locate in inflammatory, acidbase;

Identify InflammatoryAugmentationandPlateletsLoworFallSevere as InflammatoryAugmentationSevere and PlateletLowOrFallSevere within 1d locate in inflammatory, acidbase;

Identify InflammatoryAugmentationandPlateletsLoworFallProfound as InflammatoryAugmentationProfound and PlateletLowOrFallSevere within 1d locate in inflammatory, acidbase;

—InflammatoryAugmentation and Low or Fall Calcium

Identify InflammatoryAugmentationandCalciumMarginal as InflammatoryAugmentationMarginal and FallorLowCalciumMarginal within 1d locate in inflammatory, acidbase;

Identify InflammatoryAugmentationandCalciumMild as InflammatoryAugmentationMild and FallorLowCalciumMild within 1d locate in inflammatory, acidbase;

Identify InflammatoryAugmentationandCalciumMod as InflammatoryAugmentationMod and FallorLowCalciumMod within 1d locate in inflammatory, acidbase;

Identify InflammatoryAugmentationandCalciumSevere as InflammatoryAugmentationSevere and FallorLowCalciumSevere within 1d locate in inflammatory, acidbase;

Identify InflammatoryAugmentationandCalciumProfound as InflammatoryAugmentationProfound and FallorLowCalciumProfound within 1d locate in inflammatory, acidbase;

—InflammatoryAugmentation and High or Rise Creatinine

Identify InflammatoryAugmentationandCreatinineMarginal as InflammatoryAugmentationMarginal and CreatinineRiseOrHighMarginal within 1d locate in inflammatory, Renal;

Identify InflammatoryAugmentationandCreatinineFailureMild as InflammatoryAugmentationMild and CreatinineRiseOrHighMild within 1d locate in inflammatory, Renal;

Identify InflammatoryAugmentationandCreatinineMod as InflammatoryAugmentationMod and CreatinineRiseOrHighMod within 1d locate in inflammatory, Renal;

Identify InflammatoryAugmentationandCreatinineSevere as InflammatoryAugmentationSevere and CreatinineRiseOrHighSevere within 1d locate in inflammatory, Renal;

Identify InflammatoryAugmentationandCreatinineProfound as InflammatoryAugmentationProfound and CreatinineRiseOrHighProfound within 1d locate in inflammatory, Renal;

—InflammatoryAugmentation and Fall or Low Albumin

Identify InflammatoryAugmentationandAlbuminMarginal as InflammatoryAugmentationMarginal and AlbuminFallMarginal within 1d locate in inflammatory, Renal;

Identify InflammatoryAugmentationandAlbuminFailureMild as InflammatoryAugmentationMild and AlbuminFallMild within 1d locate in inflammatory, Renal;

Identify InflammatoryAugmentationandAlbuminMod as InflammatoryAugmentationMod and AlbuminFallModerate within 1d locate in inflammatory, Renal;

Identify InflammatoryAugmentationandAlbuminSevere as InflammatoryAugmentationSevere and AlbuminFallSevere within 1d locate in inflammatory, Renal;

Identify InflammatoryAugmentationandAlbuminProfound as InflammatoryAugmentationProfound and AlbuminFallProfound within 1d locate in inflammatory, Renal;

—SIRS and Acid

Identify SIRSandAcidMarginal as SIRSMarginal and AcidosisOrBicarbFallorLoworLactateMarginal within 1d locate in inflammatory, acidbase;

Identify SIRSandAcidMild as SIRSMild and AcidosisOrBicarbFallorLoworLactateMild within 1d locate in inflammatory, acidbase;

Identify SIRSandAcidMod as SIRSMod and AcidosisOrBicarbFallorLoworLactateMod within 1d locate in inflammatory, acidbase;

Identify SIRSandAcidSevere as SIRSSevere and AcidosisOrBicarbFallorLoworLactateSevere within 1d locate in inflammatory, acidbase;

Identify SIRSandAcidProfound as SIRSProfound and AcidosisOrBicarbFallorLoworLactateProfound within 1d locate in inflammatory, acidbase;

—SIRS and Low or Fall Platelets

Identify SIRSandPlateletsLoworFallMarginal as SIRSMarginal and PlateletLowOrFallMarginal within 1d locate in inflammatory, acidbase;

Identify SIRSandPlateletsLoworFallMild as SIRSMild and PlateletLowOrFallMild within 1d locate in inflammatory, acidbase;

Identify SIRSandPlateletsLoworFallMod as SIRSMod and PlateletLowOrFallModerate within 1d locate in inflammatory, acidbase;

Identify SIRSandPlateletsLoworFallSevere as SIRSSevere and PlateletLowOrFallSevere within 1d locate in inflammatory, acidbase;

Identify SIRSandPlateletsLoworFallProfound as SIRSProfound and PlateletLowOrFallProfound within 1d locate in inflammatory, acidbase;

—SIRS and Low or Fall Calcium

Identify SIRSandAcidMarginal_Duplicated as SIRSMarginal and FallorLowCalciumMarginal within 1d locate in inflammatory, acidbase;

Identify SIRSandAcidMild_Duplicated as SIRSMild and FallorLowCalciumMild within 1d locate in inflammatory, acidbase;

Identify SIRSandAcidMod_Duplicated as SIRSMod and FallorLowCalciumMod within 1d locate in inflammatory, acidbase;

Identify SIRSandAcidSevere_Duplicated as SIRSSevere and FallorLowCalciumSevere within 1d locate in inflammatory, acidbase;

Identify SIRSandAcidProfound_Duplicated as SIRSProfound and FallorLowCalciumProfound within 1d locate in inflammatory, acidbase;

—SIRS and High or Rise Creatinine

Identify SIRSandCreatinineMarginal as SIRSMarginal and CreatinineRiseOrHighMarginal within 1d locate in inflammatory, Renal;

Identify SIRSandCreatinineMild as SIRSMild and CreatinineRiseOrHighMild within 1d locate in inflammatory, Renal;

Identify SIRSandCreatinineMod as SIRSMod and CreatinineRiseOrHighMod within 1d locate in inflammatory, Renal;

Identify SIRSandCreatinineSevere as SIRSSevere and CreatinineRiseOrHighSevere within 1d locate in inflammatory, Renal;

Identify SIRSandCreatinineProfound as SIRSProfound and CreatinineRiseOrHighProfound within 1d locate in inflammatory, Renal;

—SIRS and Fall or Low Albumin

Identify SIRSandAlbuminMarginal as SIRSMarginal and AlbuminFallMarginal within 1d locate in inflammatory, Renal;

Identify SIRSandAlbuminFailureMild as SIRSMild and AlbuminFallMild within 1d locate in inflammatory, Renal;

Identify SIRSandAlbuminMod as SIRSMod and AlbuminFallModerate within 1d locate in inflammatory, Renal;
Identify SIRSandAlbuminSevere as SIRSSevere and AlbuminFallSevere within 1d locate in inflammatory, Renal;
Identify SIRSandAlbuminProfound as SIRSProfound and AlbuminFallProfound within 1d locate in inflammatory, Renal;
—SIRS
Identify SIRSandPDAcidosisOrLactateSaO2Marginal as SIRSMarginal and PDAcidosisOrLactateSaO2Marginal within 1d locate in inflammatory, Respiratory;
Identify SIRSandPDAcidosisOrLactateSaO2Mild as SIRSMild and PDAcidosisOrLactateSaO2Mild within 1d locate in inflammatory, Respiratory;
Identify SIRSandPDAcidosisOrLactateSaO2Mod as SIRSMod and PDAcidosisOrLactateSaO2Mod within 1d locate in inflammatory, Respiratory;
Identify SIRSandPDAcidosisOrLactateSaO2Severe as SIRSSevere and PDAcidosisOrLactateSaO2Severe within 1d locate in inflammatory, Respiratory;
Identify SIRSandPDAcidosisOrLactateSaO2Profound as SIRSProfound and PDAcidosisOrLactateSaO2Profound within 1d locate in inflammatory, Respiratory;
Identify SIRSandPDSPO2RRMarginal as SIRSMarginal and PDSPO2RRMarginal within 1d locate in inflammatory, Respiratory;
Identify SIRSandPDSPO2RRMild as SIRSMild and PDSPO2RRMild within 1d locate in inflammatory, Respiratory;
Identify SIRSandPDSPO2RRMod as SIRSMod and PDSPO2RRMod within 1d locate in inflammatory, Respiratory;
Identify SIRSandPDSPO2RRSevere as SIRSSevere and PDSPO2RRSevere within 1d locate in inflammatory, Respiratory;
Identify SIRSandPDSPO2RRProfound as SIRSProfound and PDSPO2RRProfound within 1d locate in inflammatory, Respiratory;
—Identify SIRS and Respiratory Failure
Identify SIRSandRespFailureMarginal as SIRSandPDAcidosisOrLactateSaO2Marginal or SIRSandPDSPO2RRMarginal locate in inflammatory, Respiratory;
Identify SIRSandRespFailureMild as SIRSandPDAcidosisOrLactateSaO2Mild or SIRSandPDSPO2RRMild locate in inflammatory, Respiratory;
Identify SIRSandRespFailureMod as SIRSandPDAcidosisOrLactateSaO2Mod or SIRSandPDSPO2RRMod locate in inflammatory, Respiratory;
Identify SIRSandRespFailureSevere as SIRSandPDAcidosisOrLactateSaO2Severe or SIRSandPDSPO2RRSevere locate in inflammatory, Respiratory;
Identify SIRSandRespFailureProfound as SIRSandPDAcidosisOrLactateSaO2Profound or SIRSandPDSPO2RRProfound locate in inflammatory, Respiratory;
—PAID Parenteral Antibiotic Indicating Disorder
Identify Sepsis as
  SIRSMarginal or
  SIRSMild
    locate in inflammatory
    indicate PAID;
Identify SepsisModerate as
  SIRSMod or
  InflammatoryAugmentationMod or
  InflammatoryAugmentationandPlateletsLoworFallMild or
  InflammatoryAugmentationandCalciumMod or
  SIRSandAlbuminMod or
  SIRSandCreatinineMild
    locate in inflammatory
    indicate PAID;
Identify SepsisSevere as
  SIRSSevere or
  InflammatoryAugmentationSevere or
  SIRSandRespFailureMild or
  InflammatoryAugmentationandAcidMod or
  SIRSandCreatinineMod or
  InflammatoryAugmentationandPlateletsLoworFallMod or
  NeutrophilFailureMod or
  SIRSandAcidMod
    locate in inflammatory
    indicate PAID, Sepsis;
Identify SepsisProfound as
  SIRSSevere or
  InflammatoryAugmentationProfound or
  SIRSandRespFailureMod or
  InflammatoryAugmentationandAcidSevere or
  SIRSandCreatinineSevere or
  InflammatoryAugmentationandPlateletsLoworFallSevere or
  NeutrophilFailureSevere or
  SIRSandAcidMod
    locate in inflammatory
    indicate PAID, Sepsis;
Identify SepsisPromptResuscitationRequired as
  SIRSandRespFailureSevere or
  InflammatoryAugmentationandAcidProfound or
  SIRSandAcidSevere
    locate in inflammatory
    indicate PAID, Sepsis;

What is claimed is:

1. A real-time patient monitoring system comprising:
a real-time patient monitor communicatively coupled to a plurality of measurement devices, the patient monitor having a display device, a memory to store instructions, and one or more processors communicatively coupled to the memory and the display; and
a storage device in communication with the patient monitor configured to store historical physiologic and laboratory data values about a plurality of physiological systems of a patient;
wherein the instructions, when executed by one of the one or more processors, cause the patient monitoring system to
  receive in real-time a plurality of time series, each of the time series being biologic particle density values of a biologic particle type associated with a patient,
  generate a plurality of perturbations by identifying changes in the biological particle density values of the plurality of time series,
  determine, for each perturbation, a plurality of properties of the perturbation, wherein the properties include at least one of a slope, a magnitude, a percent change, a change duration, a minimum, a maximum, and a change relative to a normal range for the biologic particle density of the biologic particle type,
  assign a severity value to each determined property of each perturbation, wherein the severity values correspond to the severity of the determined property with respect to at least one clinical condition, generate in real time a plurality of sequential severity profiles over time for each clinical condition, each severity profile being responsive to severity values of the properties of the perturbations associated with the clinical condition;

generate as an early warning a first dynamic image based on the plurality of sequential severity profiles, the first dynamic image having a first time series of a plurality of first images, each first image of the plurality of first images having a cell corresponding to a status of a clinical condition of the patient at a point-in-time wherein a color distribution of the cell corresponds to at least one of the plurality of sequential severity profiles, and present in real-time, on a map presented at the display device, one of the plurality of first images of the first dynamic image, the map comprising a plurality of map regions, each map region of the plurality of map regions corresponding to a physiological system of a plurality of physiological systems of the patient.

2. The patient monitoring system of claim 1, wherein the instructions, when executed, further cause the patient monitoring system to generate a second dynamic image comprising a second time series of a plurality of second images, each second image generated based on the plurality of sequential severity profiles and visually depicting a status of the clinical condition at a point-in-time;

present, along a time axis presented at the display device, one or more second images of the plurality of second images of the second dynamic, and indicate which one of the plurality of second images displayed on the time axis corresponds to one of the first images of the plurality of first images of the first dynamic image that is currently displayed on the map.

3. The patient monitoring system of claim 2, wherein an indication of a patient treatment event is positioned along the time axis.

4. The patient monitoring system of claim 1, wherein:

the first dynamic image is one of a plurality of dynamic images generated for a plurality of patients, each dynamic image visually depicting a status of one of at least one clinical condition at one of the plurality of patients; and each of the plurality of dynamic images are presented simultaneously in a trellis display.

5. The patient monitoring system as in claim 4 in which the plurality of dynamic images are sorted at the trellis display by severity of the clinical condition.

6. The patient monitoring system as in claim 1 wherein a histogram is generated and presented adjacent the first dynamic image and individual first images of the first dynamic image are presented on the map in response to receipt of user input selecting individual points-in-time on the histogram.

7. The patient monitoring system as in claim 3 in which the second dynamic image comprises an indication of a relationship between the patient treatment event and one of the plurality of second images of the second dynamic image.

8. The patient monitoring system as in claim 2 in which one of the first images of the first dynamic image and one of the second images of the second dynamic image are each associated with a point-in-time, and the first image and the second image associated with the point-in-time are each presented in response to receipt of user input selecting the point-in-time.

9. The patient monitoring system of claim 1 wherein the clinical condition is sepsis.

10. The patient monitoring system of claim 1, wherein:

the instructions, when executed, further cause the patient monitoring system to animate the first dynamic image by presenting in sequence at least two first images of the plurality of first images.

11. The patient monitoring system of claim 1, wherein:

the instructions, when executed, cause the patient monitoring system to generate a severity profile of the one or more sequential severity profiles by executing a script associated with a clinical sub-condition, the script configured to generate the severity profile by aggregating at least two sequential severity profiles generated for at least two perturbations associated with the clinical sub-condition.

12. The patient monitoring system of claim 1, wherein:

the instructions, when executed, cause the patient monitoring system to generate a severity profile of the one or more sequential severity profiles by generating a first severity profile associated with a first clinical sub-condition, generating a second severity profile associated with a second clinical sub-condition, and aggregating the first severity profile and the second severity profile to obtain the severity profile.

13. A real-time patient monitoring system comprising:

a real-time patient monitor communicatively coupled to a plurality of measurement devices, the patient monitor having a display device, a memory to store instructions, and one or more processors communicatively coupled to the memory and the display; and a storage device in communication with the patient monitor configured to store historical physiologic and laboratory data values about a plurality of physiological systems of a patient;

wherein the instructions, when executed by the one or more processors, cause the patient monitoring system to receive in real-time a plurality of time series, each of the time series being biologic particle density values of a biologic particle type associated with a patient, generate a plurality of perturbations by identifying changes in the biological particle density values of the plurality of time series, determine, for each perturbation, a plurality of properties of the perturbation, wherein the properties include at least one of a slope, a magnitude, a percent change, a change duration, a minimum, a maximum, and a change relative to a normal range for the biologic particle density, assign a severity value to each determined property of each perturbation, wherein the severity values correspond to the severity of the determined property with respect to at least one clinical condition, generate in real-time a plurality of sequential severity profiles over time for each clinical condition, each severity profile being responsive to severity values of the properties of the perturbations associated with the physiological system, generate as an early warning, based on the plurality of sequential severity profiles, a dynamic image comprising a time series of a plurality of images, each image of the plurality of images comprising a cell corresponding to a status of a clinical condition at a point-in-time of a plurality of points-in-time wherein a color distribution of the cell corresponds to at least one of the plurality of sequential severity profiles, determine, based on the data, a potential future status of the clinical condition and generate, based on the data, a visual indication of the potential future status of the clinical condition, the visual indication comprising a change to the color distribution of the cell, animate in real-time the dynamic image on a map presented at the display device by presenting in sequence at least two images of the plurality of images of the dynamic image, and present in real-time, on the map, the visual indication of the potential future status of the clinical condition.

14. The patient monitoring system of claim 13, wherein the clinical condition is sepsis.

15. The patient monitoring system as in claim 13, wherein the instructions, when executed, further cause the patient monitoring system to determine a probability of the potential future status of the clinical condition and present the probability on the map with the visual indication of the potential future status of the clinical condition.

16. The patient monitoring system of claim 13, wherein:
each image of the plurality of images corresponds to a point-in-time of a plurality of points-in-time;
the map comprises a two-dimensional map and a time axis at which one of the plurality of points-in-time is selectable; and
the instructions, when executed, further cause the patient monitoring system to present, at the display device in response to receipt of user input selecting one of the plurality of points-in-time, one of the plurality of images that corresponds to the selected point-in-time.

17. The patient monitoring system of claim 15, wherein the clinical condition is sepsis.

18. The patient monitoring system of claim 13, wherein:
the instructions, when executed, further cause the patient monitoring system to
present, at the display device on a two-dimensional map comprising a time axis, a second dynamic image visually depicting the clinical condition during a time period comprising one or more of the plurality of points-in-time, the second dynamic image comprising a second time series of a plurality of second images, each second image of the plurality of second images corresponding to one of the plurality of points-in-time and presented along the time axis at a corresponding point-in-time.

19. The patient monitoring system of claim 13, wherein the visual indication of the future status of the clinical condition further comprises a change to a size or a shape of the cell.

20. A real-time patient monitoring system comprising:
a real-time patient monitor communicatively coupled to a plurality of measurement devices, the patient monitor having a display device, a memory to store instructions, and one or more processors communicatively coupled to the memory and the display; and
a storage device in communication with the patient monitor configured to store historical physiologic and laboratory data values about a plurality of physiological systems of a patient;
wherein the instructions, when executed by the one or more processors, cause the patient monitoring system to
receive in real-time a plurality of time series, each time series being biologic particle density values of a biologic particle type associated with the patient;
generate a plurality of perturbations by identifying changes in the biological particle density values of the plurality of time series;
determine, for each perturbation, a plurality of properties of the perturbation, wherein the properties include at least one of a slope, a magnitude, a percent change, a change duration, a minimum, a maximum, and a change relative to a normal range for the biologic particle density of the biologic particle type;
assign a severity value to each determined property of each perturbation, wherein the severity values correspond to the severity of the determined property with respect to at least one physiological system;
generate in real-time a plurality of sequential severity profiles over time for each physiological system, each severity profile responsive to severity values of the properties of the perturbations associated with the physiological system;
display, on the display device, a two-dimensional map having a horizontal time axis and one or more columns extending across the horizontal time axis, wherein each column corresponds to a given time period, the two-dimensional map further having a plurality of rows, each row corresponding to one of the physiological systems;
generate an image for each of the plurality of sequential severity profiles, each image having one or more cells arranged perpendicular to the horizontal time axis and having a width equal to the width of the one or more columns, wherein the number of the one or more cells and the color of each of the one or more cells are based on one or more of the determined perturbations, the determined properties of each perturbation, the assigned severity values of each property, or the determined severity profile of each physiological system; and
display in real-time, across the one or more columns, a sequence of the generated images for the sequential severity profiles associated with the physiological systems corresponding to the time period of each column such that the sequence of generated images visually depict a severity-centric progression of the physiological systems over time.

* * * * *